US012667355B2

(12) United States Patent
Choi

(10) Patent No.: US 12,667,355 B2
(45) Date of Patent: Jun. 30, 2026

(54) SHAFT ATTACHMENT AND DETACHMENT APPARATUS

(71) Applicant: LIVSMED INC., Seongnam-si (KR)

(72) Inventor: Woo Jung Choi, Siheung-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 19/016,186

(22) Filed: Jan. 10, 2025

(65) Prior Publication Data

US 2025/0228560 A1     Jul. 17, 2025

(30) Foreign Application Priority Data

Jan. 11, 2024     (KR) ........................ 10-2024-0005000

(51) Int. Cl.
*A61B 17/072* (2006.01)
*A61B 17/00* (2006.01)

(52) U.S. Cl.
CPC .................. *A61B 17/07207* (2013.01); *A61B 2017/0046* (2013.01); *A61B 2017/00477* (2013.01); *A61B 2017/00862* (2013.01)

(58) Field of Classification Search
CPC .............................................. A61B 17/07207
See application file for complete search history.

(56) References Cited

U.S. PATENT DOCUMENTS

| | | | | |
|---|---|---|---|---|
| 10,492,813 | B2 * | 12/2019 | Sholev | ............. A61B 17/00234 |
| 2016/0324520 | A1 * | 11/2016 | Marczyk | ............. A61B 17/072 |
| 2022/0369903 | A1 | 11/2022 | Schneider et al. | |

FOREIGN PATENT DOCUMENTS

| | | |
|---|---|---|
| JP | H07-275183 A | 10/1995 |
| JP | 2017-070637 A | 4/2017 |
| JP | 2017-129229 A | 7/2017 |
| JP | 2019-503784 A | 2/2019 |

* cited by examiner

*Primary Examiner* — Nathaniel C Chukwurah
(74) *Attorney, Agent, or Firm* — Bridgeway IP Law Group, PLLC; Sang Ho Lee; Hyun Woo Shin

(57)     ABSTRACT

A shaft attachment and detachment apparatus for attaching and detaching a shaft having grooves formed on one end portion to and from a device body includes a sleeve surrounding at least a portion of an outer surface of the shaft and movable in an axial direction of the shaft, a connector base into which one end portion of the shaft is inserted and which is coupled to the device body, and a latch member coupled to the connector base and including one or more latches, wherein the one or more latches are coupled to the grooves, which are formed in the shaft, to couple the shaft to the connector base, and the coupled state of the one or more latches and the grooves is changeable depending on a position of the sleeve disposed on the shaft.

34 Claims, 44 Drawing Sheets

SHAFT ATTACHMENT AND DETACHMENT APPARATUS

CROSS-REFERENCE TO RELATED APPLICATION

This application is based on and claims priority under 35 USC § 119 to Korean Patent Application No. 10-2024-0005000, filed on Jan. 11, 2024, in the Korean Intellectual Property Office, the disclosure of which is incorporated by reference herein in its entirety.

BACKGROUND

1. Field

The present disclosure relates to a shaft attachment and detachment apparatus, and more particularly, to an apparatus for attaching and detaching a shaft for use in various surgical devices.

2. Description of the Related Art

Medically, surgery refers to the treatment of diseases by cutting, slitting, or manipulating the skin, mucous membranes, or other tissues using medical devices. In particular, open surgery in which the skin of the surgical site is incised and opened to treat, shape, remove organs or the like therein and the like cause problems such as bleeding, side effects, patient pain, scarring. Accordingly, recently, surgery performed by inserting only a medical device, for example, laparoscopic surgical instrument, microsurgical microscope, and the like by forming a predetermined hole in the skin or surgery using a robot has been spotlighted as an alternative.

A surgical instrument is a tool equipped with an end tool provided on one end of a shaft that passes through a hole drilled in the skin, and is manipulated by a medical doctor by hand using a predetermined driving part or by a robot arm to perform surgery at the surgical site. The end tool provided on the surgical instrument performs a rotational motion, a gripping motion, a cutting motion, or the like through a predetermined structure.

The surgical instrument including such an end tool includes a shaft-shaped structure. The user attaches the instrument to a handle and uses the instrument. Alternatively, the user may remove the used instrument from the handle, replace it with another instrument, and then use the replacement instrument. As such, there is often a need for easy attachment and detachment of a specific object to another object in the operating room environment. For example, a device is required for attaching and detaching one instrument to and from another in various cases, such as attaching and detaching a disposable instrument to and from a handle of a stapler, attaching and detaching different sizes of drill bits to and from a power drill, attaching and detaching a disposable sterile handle to and from an infrared light, or attaching and detaching various peripherals to and from a surgical bed siding.

However, tools used in a typical operating room environment use the following coupling mechanisms.

The mechanisms include a method of tightening an inserted accessory using a collet structure, a method of inserting an accessory into a hole and then manipulating a fixing screw or the like to tighten the accessory, and a method in which a protrusion such as a pin protrudes when an accessory is inserted into a hole, and fixes the accessory by being caught in a groove of a device.

These coupling methods are often implemented in a cumbersome manner, for example, while these coupling methods may be convenient to use, these coupling methods often require the use of both hands to remove the accessory or may result in the accessory not being firmly fixed.

The background art described above is technical information retained by the present inventors in order to derive the present disclosure or obtained by the present inventors in the process of deriving the present disclosure, and thus is not necessarily known art disclosed to the general public before the filing of the present application.

SUMMARY

The present disclosure is directed to providing an apparatus for attaching and detaching a shaft, specifically, a shaft attachment and detachment apparatus allowing a shaft to be easily attached and detached with one-hand operation.

Additional aspects will be set forth in part in the description which follows and, in part, will be apparent from the description, or may be learned by practice of the presented embodiments of the disclosure.

According to an aspect of the present disclosure, there is provided a shaft attachment and detachment apparatus for attaching and detaching a shaft having grooves formed on one end portion to and from a device body, the shaft attachment and detachment apparatus including a sleeve surrounding at least a portion of an outer surface of the shaft and movable in an axial direction of the shaft, a connector base into which one end portion of the shaft is inserted and which is coupled to the device body, and a latch member coupled to the connector base and including one or more latches, wherein the latches are coupled to the grooves, which are formed in the shaft, to couple the shaft to the connector base, and the coupled state of the latches and the grooves is changeable depending on a position of the sleeve disposed on the shaft.

In an embodiment of the present disclosure, the coupling of the latch and the groove may be maintained while the sleeve covers the latches coupled to the grooves, and the coupling of the latches and the grooves may be released while the sleeve does not cover the latches coupled to the grooves.

In an embodiment of the present disclosure, the shaft attachment and detachment apparatus may further include an elastic member housing disposed between the sleeve and an outer circumferential surface of the shaft and fixedly coupled to the shaft, wherein, the elastic member housing may include an elastic member disposed between the sleeve and the elastic member housing, the elastic member may provide an elastic force in a direction of pushing the sleeve toward the groove of the shaft, and the sleeve may cover the latches as the latches are disposed in a separation space formed between the sleeve and the shaft.

In an embodiment of the present disclosure, by moving the sleeve toward a distal end, which is in a direction away from the connector base, the latches may be exposed to the outside of the sleeve, and the coupling of the latches and the grooves may be released.

In an embodiment of the present disclosure, in a state in which the sleeve covers the latches, uncoupling of the latches from the grooves may be limited even when an external force is applied to the shaft.

In an embodiment of the present disclosure, the latch member may include a body fixedly coupled to the connector base, legs each formed to extend from the body, and the latch formed on an end portion of each of the legs, wherein the latch may include an inner side protrusion with at least one region inserted into the groove of the shaft.

In an embodiment of the present disclosure, the body of the latch member may include a through hole through which the shaft may be inserted, and the leg may be formed to extend from the body toward the groove along an outer circumferential surface of the shaft.

In an embodiment of the present disclosure, each of the latches may include an outer side protrusion formed on an opposite side of the inner side protrusion, and, when the shaft is inserted into the connector base, the latches may spread in a direction away from a central axis of the shaft while interfering with the outer circumferential surface of the shaft, and the outer side protrusion may come in contact with the sleeve.

In an embodiment of the present disclosure, the sleeve may interfere with the outer side protrusion and thus may be slidably moved in a direction opposite to an insertion direction of the shaft.

In an embodiment of the present disclosure, when the shaft is further inserted toward the connector base, at least one region of the inner side protrusion may be inserted into the groove to couple the latch to the groove.

In an embodiment of the present disclosure, the inner side protrusion may include a first inclined surface formed to have a greater height on a distal end side, which is in a direction away from the connector base, than on a proximal end side, which is in a direction close to the connector base.

In an embodiment of the present disclosure, the groove of the shaft may include a groove-inclined surface formed such that a width of the groove becomes smaller toward an inner surface from an outer surface of the shaft.

In an embodiment of the present disclosure, the shaft may have a key groove extending in a longitudinal direction at an end portion thereof, the connector base may have at least one protrusion formed on an inner surface thereof, protruding toward a central axis of the shaft, and as the protrusion is fitted into the key groove, an axial rotation of the shaft may be prevented.

In an embodiment of the present disclosure, each of the latches may include an outer side protrusion formed on an opposite side of the inner side protrusion, wherein the outer side protrusion may include a third inclined surface formed to have a higher height on a proximal end side, which is in a direction close to the connector base, than on a distal end side, which is in a direction away from the connector base, and the sleeve may include a fourth inclined surface, which corresponds to the third inclined surface, on one end portion thereof facing the latch.

In an embodiment of the present disclosure, the third inclined surface and the fourth inclined surface may be in contact with each other, and the fourth inclined surface may press the third inclined surface toward the center of the shaft.

In an embodiment of the present disclosure, the sleeve may include a locking protrusion extending from the fourth inclined surface and may be formed to be parallel to the shaft.

According to an aspect of the present disclosure, there is provided a device attachment and detachment module provided in a device body to attach and detach a shaft to and from the device body, the device attachment and detachment module including a connector base into which one end portion of the shaft is inserted and which is coupled to the device body, and a latch member coupled to the connector base and including one or more latches, wherein the latches may be coupled to the shaft to couple the shaft to the connector base, and the coupled state of the latches and the shaft may changeable by a sleeve disposed on the shaft.

In an embodiment of the present disclosure, the third inclined surface and the fourth inclined surface may be in contact with each other, and the fourth inclined surface may press the third inclined surface toward the center of the shaft.

In an embodiment of the present disclosure, the sleeve may include a locking protrusion extending from the fourth inclined surface and may be formed to be parallel to the shaft.

According to an aspect of the present disclosure, there is provided a device attachment and detachment module provided in a device body to attach and detach a shaft to and from the device body, the device attachment and detachment module including a connector base into which one end portion of the shaft is inserted and which is coupled to the device body, and a latch member coupled to the connector base and including one or more latches, wherein the latches may be coupled to the shaft to couple the shaft to the connector base, and the coupled state of the latches and the shaft may changeable through a sleeve disposed on the shaft.

In an embodiment of the present disclosure, the latch member may include a body fixedly coupled to the connector base, legs each formed to extend from the body, and the latch formed on an end portion of each of the legs, wherein the latch may include an inner side protrusion with at least one region inserted into the groove formed on one end portion of the shaft.

In an embodiment of the present disclosure, each of the latches may include an outer side protrusion formed on an opposite side of the inner side protrusion, and, when the shaft is inserted into the connector base, the latches may spread in a direction away from a central axis of the shaft while interfering with the outer circumferential surface of the shaft, and the outer side protrusion may come in contact with the sleeve.

In an embodiment of the present disclosure, the sleeve may interfere with the outer side protrusion and thus may be slidably moved in a direction opposite to an insertion direction of the shaft.

In an embodiment of the present disclosure, when the shaft is further inserted toward the connector base, at least one region of the inner side protrusion may be inserted into the groove to couple the latch to the groove.

In an embodiment of the present disclosure, each of the latches may include an outer side protrusion formed on an opposite side of the inner side protrusion, wherein the outer side protrusion may include a third inclined surface formed to have a higher height on a proximal end side, which is in a direction close to the connector base, than on a distal end side, which is in a direction away from the connector base, and the sleeve may include a fourth inclined surface, which corresponds to the third inclined surface, on one end portion thereof facing the latch.

In an embodiment of the present disclosure, the third inclined surface and the fourth inclined surface may be in contact with each other, and the fourth inclined surface may press the third inclined surface toward the center of the shaft.

According to an aspect of the present disclosure, there is provided a shaft attachment and detachment module provided on a shaft having grooves formed on one end portion to attach and detach the shaft to and from a device body, the shaft attachment and detachment module including a sleeve surrounding at least a portion of an outer surface of the shaft and movable in an axial direction of the shaft, and an elastic member housing disposed between the sleeve and an outer circumferential surface of the shaft and fixedly coupled to the shaft, wherein, the elastic member housing may include an elastic member disposed between the sleeve and the elastic member housing, the shaft may be coupled to the device body by latches included in the device body, and the coupled state of the latches and the shaft may be changeable depending on a position of the sleeve disposed on the shaft.

In an embodiment of the present disclosure, the latches may be respectively coupled to the grooves formed on one end portion of the shaft, the coupling of the latches and the grooves may be maintained while the sleeve covers the latches coupled to the grooves, and the coupling of the latches and the grooves may be released while the sleeve does not cover the latches coupled to the grooves.

In an embodiment of the present disclosure, the elastic member may provide an elastic force in a direction of pushing the sleeve toward the groove of the shaft, and the sleeve may cover the latches as the latches are disposed in a separation space formed between the sleeve and the shaft.

In an embodiment of the present disclosure, by moving the sleeve toward a distal end, which is in a direction away from the device body, the latches may be exposed to the outside of the sleeve, and the coupling of the latches and the grooves may be released.

In an embodiment of the present disclosure, in a state in which the sleeve covers the latches, uncoupling of the latches from the grooves may be limited even when an external force may be applied to the shaft.

According to an aspect of the present disclosure, there is provided a shaft attachment and detachment apparatus including a connector base into which one end portion of a shaft is inserted and which is coupled to a device body, and a cover coupled to the connector base and including an inner side surface therein, a reaction force member disposed between the connector base and the cover and formed to be in contact with the inner side surface of the cover, and a pusher member disposed to pass through the cover and pressable against the reaction force member, wherein, when the shaft inserted into the connector base may be withdrawn from the connector base, the reaction force member presses a side surface of the shaft to couple the shaft to the device body.

in an embodiment of the present disclosure, the reaction force member may include an elastic member coupled to the connector base, and a friction member coupled to an end portion of the elastic member.

in an embodiment of the present disclosure, the cover may form an inner inclined surface so that a space inside the cover formed by the inner side surface becomes narrower as a distance from the connector base increases, wherein the inner inclined surface may guide at least a portion of the reaction force member to move toward a central axis of the shaft.

In an embodiment of the present disclosure, the pusher member may include a pressing part formed on an end portion opposite to one end portion in contact with the reaction force member, and as the pressing part is pressed, the pusher member may press the reaction force member, and the reaction force member may be compressed or moved backward toward the connector base.

In an embodiment of the present disclosure, when the reaction force member is pressed or moved backward toward the connector base, the reaction force member may be spaced apart from the inner side surface of the cover, and the coupled state for fixing the shaft may be released.

In an embodiment of the present disclosure, the shaft may include a main region, and an end portion region adjacent to the connector base than the main region, wherein the end portion region may have a width less than a width of the main region.

In an embodiment of the present disclosure, in a state in which the shaft is inserted into and coupled to the connector base, the reaction force member may partially come into contact with the main region.

In an embodiment of the present disclosure, in a state in which the shaft is partially withdrawn from the connector base, the reaction force member may be spaced apart from the end portion region of the shaft.

In an embodiment of the present disclosure, the reaction force member may be provided in a plural number, and the plurality of reaction force members may be symmetrically disposed with respect to the shaft.

According to an aspect of the present disclosure, there is provided a medical device including a shaft attachment and detachment apparatus, the medical device including a connection member including a shaft-shaped coupling part having grooves formed on one end portion thereof, a sleeve surrounding at least a portion of an outer surface of the coupling part and movable in an axial direction of the coupling part, a connector base into which one end portion of the coupling part may be inserted and which may be coupled to the device body, and a latch member coupled to the connector base and including one or more latches, wherein the latches may be respectively coupled to the grooves, which are formed in the coupling part, to couple the connection member to the connector base, the coupled state of the latches and the grooves may be changeable depending on a position of the sleeve disposed on the coupling part.

In an embodiment of the present disclosure, the coupling of the latch and the groove may be maintained while the sleeve covers the latches coupled to the grooves, and the coupling of the latches and the grooves may be released while the sleeve does not cover the latches coupled to the grooves.

In an embodiment of the present disclosure, the medical device may further include an elastic member housing disposed between the sleeve and an outer circumferential surface of the coupling part and fixedly coupled to the coupling part, wherein the elastic member housing may include an elastic member disposed between the sleeve and the elastic member housing, the elastic member may provide an elastic force in a direction of pushing the sleeve toward the groove of the coupling part, and the sleeve may cover the latches as the latches are disposed in a separation space formed between the sleeve and the coupling part.

In an embodiment of the present disclosure, by moving the sleeve toward a distal end, which is in a direction away from the connector base, the latches may be exposed to the outside of the sleeve, and the coupling of the latches and the grooves may be released.

In an embodiment of the present disclosure, in a state in which the sleeve covers the latches, uncoupling of the latches from the grooves may be limited even when an external force is applied to the coupling part.

In an embodiment of the present disclosure, the latch member may include a body fixedly coupled to the connector base, legs each formed to extend from the body, and the latch formed on an end portion of each of the legs, wherein the latch may include an inner side protrusion with at least one region inserted into the groove of the coupling part.

In an embodiment of the present disclosure, the body of the latch member may include a through hole through which the coupling part may be inserted, and the leg may be formed to extend from the body toward the groove along an outer circumferential surface of the coupling part.

In an embodiment of the present disclosure, each of the latches may include an outer side protrusion formed on an opposite side of the inner side protrusion, and, when the coupling part is inserted into the connector base, the latches may spread in a direction away from a central axis of the coupling part while interfering with the outer circumferential surface of the coupling part, and the outer side protrusion may come in contact with the sleeve.

In an embodiment of the present disclosure, the sleeve may interfere with the outer side protrusion and thus may be slidably moved in a direction opposite to an insertion direction of the coupling part.

In an embodiment of the present disclosure, when the coupling part is further inserted toward the connector base, at least one region of the inner side protrusion may be inserted into the groove to couple the latch to the groove.

In an embodiment of the present disclosure, the inner side protrusion may include a first inclined surface formed to have a greater height on a proximal end side, which is in a direction close to the connector base, than on a distal end side, which is in a direction away from the connector base.

In an embodiment of the present disclosure, the groove of the coupling part may include a groove-inclined surface formed such that a width of the groove becomes smaller toward an inner surface from an outer surface of the coupling part.

In an embodiment of the present disclosure, the coupling part may have a key groove extending in a longitudinal direction at an end portion thereof, the connector base may have at least one protrusion formed on an inner surface thereof, protruding toward a central axis of the coupling part, and as the protrusion is fitted into the key groove, an axial rotation of the coupling part may be prevented.

In an embodiment of the present disclosure, each of the latches may include an outer side protrusion formed on an opposite side of the inner side protrusion, wherein the outer side protrusion may include a third inclined surface formed to have a higher height on a proximal end side, which is in a direction close to the connector base, than on a distal end side, which is in a direction away from the connector base, and the sleeve may include a fourth inclined surface, which corresponds to the third inclined surface, on one end portion thereof facing the latch.

In an embodiment of the present disclosure, the third inclined surface and the fourth inclined surface may be in contact with each other, and the fourth inclined surface may press the third inclined surface toward the center of the coupling part.

In an embodiment of the present disclosure, the sleeve may include a locking protrusion extending from the fourth inclined surface and may be formed to be parallel to the coupling part.

In an embodiment of the present disclosure, the connection member may be a replaceable consumable component, and the device body may be a multi-use component.

According to an aspect of the present disclosure, there is provided a medical device including a shaft attachment and detachment apparatus, the medical device including a connection member including a shaft-shaped coupling part, a connector base into which one end portion of the coupling part is inserted and which is coupled to the device body, a cover coupled to the connector base and including an inner side surface therein, a reaction force member disposed between the connector base and the cover and formed to be in contact with the inner side surface of the cover, and a pusher member disposed to pass through the cover and pressable against the reaction force member, wherein, when the coupling part inserted into the connector base is withdrawn from the connector base, the reaction force member may press a side surface of the coupling part to couple the coupling part to the device body.

in an embodiment of the present disclosure, the reaction force member may include an elastic member fixedly coupled to the connector base, and a friction member coupled to an end portion of the elastic member.

in an embodiment of the present disclosure, the cover may form an inner inclined surface so that a space inside the cover formed by the inner side surface becomes narrower as a distance from the connector base increases, wherein the inner inclined surface may guide at least a portion of the reaction force member to move toward a central axis of the coupling part.

In an embodiment of the present disclosure, the pusher member may include a pressing part formed on an end portion opposite to one end portion in contact with the reaction force member, and as the pressing part is pressed, the pusher member may press the reaction force member, and the reaction force member may be compressed or moved backward toward the connector base.

In an embodiment of the present disclosure, when the reaction force member is pressed or moved backward toward the connector base, the reaction force member may be spaced apart from the inner side surface of the cover, and the coupled state for fixing the coupling part may be released.

In an embodiment of the present disclosure, the coupling part may include a main region, and an end portion region adjacent to the connector base than the main region, wherein the end portion region may have a width less than a width of the main region.

In an embodiment of the present disclosure, in a state in which the coupling part is inserted into and coupled to the connector base, the reaction force member may partially come into contact with the main region.

In an embodiment of the present disclosure, in a state in which the coupling part is partially withdrawn from the connector base, the reaction force member may be spaced apart from the end portion region of the coupling part.

In an embodiment of the present disclosure, the reaction force member may be provided in a plural number, and the plurality of reaction force members may be symmetrically disposed with respect to the coupling part.

According to an aspect of the present disclosure, there is provided a surgical instrument including an end tool including one or more jaws and formed to be rotatable, a manipulation part configure to control a rotation of the end tool, a shaft configured to connect the manipulation part to the end tool by being coupled to the manipulation part at one end portion thereof, in which grooves are formed, and coupled to the end tool at another end portion thereof, and a sleeve surrounding at least a portion of an outer surface of the shaft and movable in an axial direction of the shaft, a connector base into which one end portion of the shaft may be inserted and which may be coupled to the manipulation part, and a latch member coupled to the connector base and including one or more latches, wherein the latches may be coupled to the grooves, which are formed in the shaft, to couple the shaft to the connector base, and the coupled state of the latches and the grooves may be changeable depending on a position of the sleeve disposed on the shaft.

In an embodiment of the present disclosure, the coupling of the latch and the groove may be maintained while the sleeve covers the latches coupled to the grooves, and the coupling of the latches and the grooves may be released while the sleeve does not cover the latches coupled to the grooves.

In an embodiment of the present disclosure, the end tool may include a staple and a blade, and the manipulation part may control a stapling motion and a cutting motion of the end tool, and the stapling motion and the cutting motion may be simultaneously performed.

In an embodiment of the present disclosure, the shaft attachment and detachment apparatus may further include an elastic member housing disposed between the sleeve and an outer circumferential surface of the shaft and coupled to the shaft, wherein, the elastic member housing may include an elastic member disposed between the sleeve and the elastic member housing, the elastic member may provide an elastic force in a direction of pushing the sleeve toward the groove of the shaft, and the sleeve may cover the latches as the latches are disposed in a separation space formed between the sleeve and the shaft.

In an embodiment of the present disclosure, by moving the sleeve toward a distal end, which is in a direction away from the connector base, the latches may be exposed to the outside of the sleeve, and the coupling of the latches and the grooves may be released.

In an embodiment of the present disclosure, in a state in which the sleeve covers the latches, uncoupling of the latches from the grooves may be limited even when an external force is applied to the shaft.

In an embodiment of the present disclosure, the latch member may include a body fixedly coupled to the connector base, legs each formed to extend from the body, and the latch formed on an end portion of each of the legs, wherein the latch may include an inner side protrusion with at least one region inserted into the groove of the shaft.

In an embodiment of the present disclosure, the body of the latch member may include a through hole through which the shaft may be inserted, and the leg may be formed to extend from the body toward the groove along an outer circumferential surface of the shaft.

In an embodiment of the present disclosure, each of the latches may include an outer side protrusion formed on an opposite side of the inner side protrusion, and, when the shaft is inserted into the connector base, the latches may spread in a direction away from a central axis of the shaft while interfering with the outer circumferential surface of the shaft, and the outer side protrusion may come in contact with the sleeve.

In an embodiment of the present disclosure, the sleeve may interfere with the outer side protrusion and thus may be slidably moved in a direction opposite to an insertion direction of the shaft.

In an embodiment of the present disclosure, when the shaft is further inserted toward the connector base, at least one region of the inner side protrusion may be inserted into the groove to couple the latch to the groove.

In an embodiment of the present disclosure, the inner side protrusion may include a first inclined surface formed to have a greater height on a proximal end side, which is in a direction close to the connector base, than on a distal end side, which is in a direction away from the connector base.

In an embodiment of the present disclosure, the groove of the shaft may include a groove-inclined surface formed such that a width of the groove becomes smaller toward an inner surface from an outer surface of the shaft.

In an embodiment of the present disclosure, the shaft may have a key groove extending in a longitudinal direction at an end portion thereof, the connector base may have at least one protrusion formed on an inner surface thereof, protruding toward a central axis of the shaft, and as the protrusion is fitted into the key groove, an axial rotation of the shaft may be prevented.

In an embodiment of the present disclosure, each of the latches may include an outer side protrusion formed on an opposite side of the inner side protrusion, wherein the outer side protrusion may include a third inclined surface formed to have a higher height on a proximal end side, which is in a direction close to the connector base, than on a distal end side, which is in a direction away from the connector base, and the sleeve may include a fourth inclined surface, which corresponds to the third inclined surface, on one end portion thereof facing the latch.

In an embodiment of the present disclosure, the third inclined surface and the fourth inclined surface may be in contact with each other, and the fourth inclined surface may press the third inclined surface toward the center of the shaft.

In an embodiment of the present disclosure, the sleeve may include a locking protrusion extending from the fourth inclined surface and may be formed to be parallel to the shaft.

According to an aspect of the present disclosure, there is provided a surgical instrument including an end tool including one or more jaws and formed to be rotatable, a manipulation part configure to control a rotation of the end tool, a shaft configured to connect the manipulation part to the end tool by being coupled to the manipulation part at one end portion thereof, in which grooves are formed, and coupled to the end tool at another end portion thereof, a connector base into which one end portion of the shaft may be inserted and which may be coupled to the manipulation part, a cover coupled to the connector base and including an inner side surface therein, a reaction force member disposed between the connector base and the cover and formed to be in contact with the inner side surface of the cover, and a pusher member disposed to pass through the cover and pressable against the reaction force member, wherein, when the shaft inserted into the connector base may be withdrawn from the connector base, the reaction force member presses a side surface of the shaft to fix the shaft.

In an embodiment of the present disclosure, the end tool may include a staple and a blade, and the manipulation part may control a stapling motion and a cutting motion of the end tool, and the stapling motion and the cutting motion may be simultaneously performed.

in an embodiment of the present disclosure, the reaction force member may include an elastic member fixedly coupled to the connector base, and a friction member coupled to an end portion of the elastic member.

in an embodiment of the present disclosure, the cover may form an inner inclined surface so that a space inside the cover formed by the inner side surface becomes narrower as a distance from the connector base increases, wherein the inner inclined surface may guide at least a portion of the reaction force member to move toward a central axis of the shaft.

In an embodiment of the present disclosure, the pusher member may include a pressing part formed on an end portion opposite to one end portion in contact with the reaction force member, and as the pressing part is pressed, the pusher member may press the reaction force member, and the reaction force member may be compressed or moved backward toward the connector base.

In an embodiment of the present disclosure, when the reaction force member is pressed or moved backward toward the connector base, the reaction force member may be spaced apart from the inner side surface of the cover, and the coupled state for fixing the shaft may be released.

In an embodiment of the present disclosure, the shaft may include a main region, and an end portion region adjacent to the connector base than the main region, wherein the end portion region may have a width less than a width of the main region.

In an embodiment of the present disclosure, in a state in which the shaft is inserted into and coupled to the connector base, the reaction force member may partially come into contact with the main region.

In an embodiment of the present disclosure, in a state in which the shaft is partially withdrawn from the connector base, the reaction force member may be spaced apart from the end portion region of the shaft.

In an embodiment of the present disclosure, the reaction force member may be provided in a plural number, and the plurality of reaction force members may be symmetrically disposed with respect to the shaft.

Other aspects, features, and advantages other than those described above will become apparent from the following drawings, claims, and detailed description of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 3 and 4 are side cross-sectional views illustrating the shaft attachment and detachment apparatus of FIG. 1;

DETAILED DESCRIPTION

Figure 1:
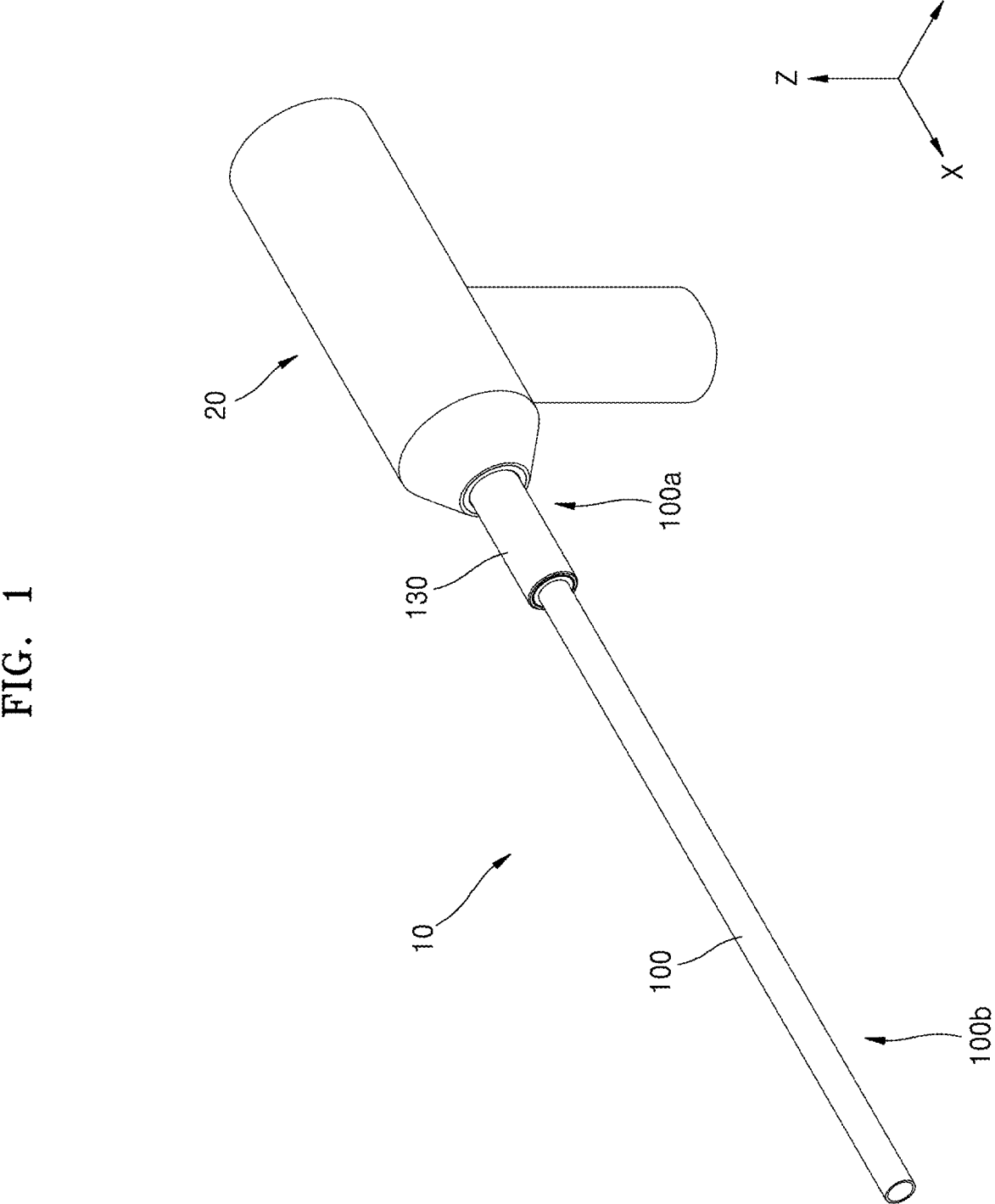
FIG. 1 is a perspective view illustrating a shaft attachment and detachment apparatus according to a first embodiment of the present disclosure and a device to which the shaft attachment and detachment apparatus is applied.
Figure 2:
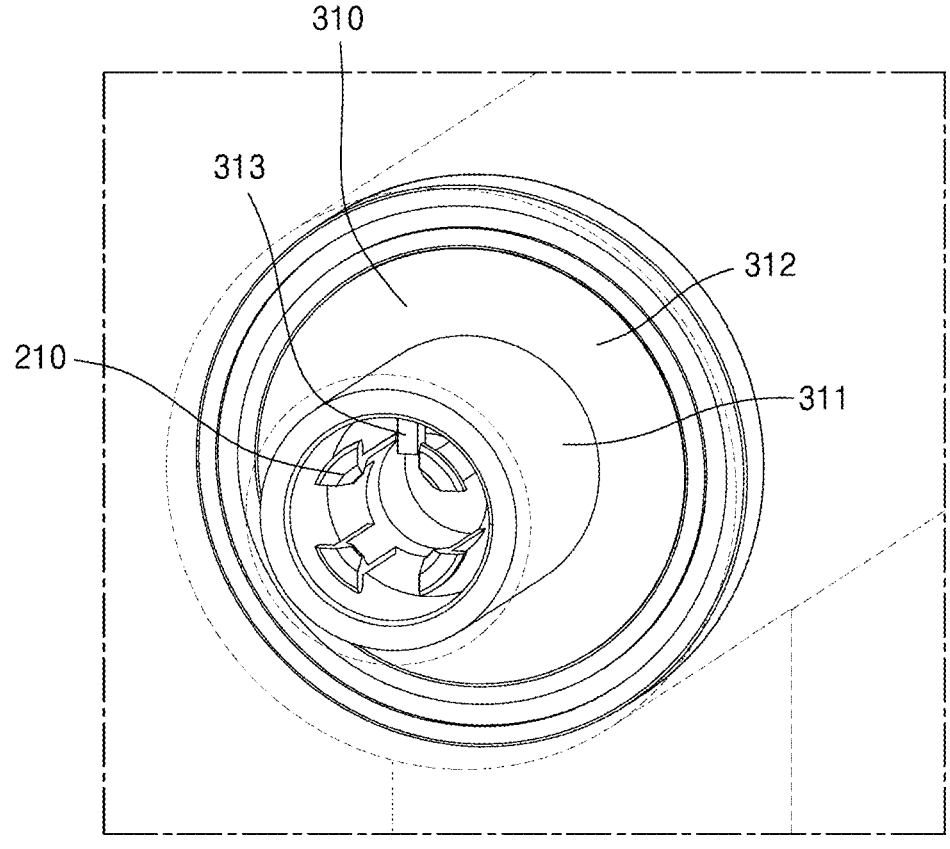
FIG. 2 is a perspective view illustrating a state in which a shaft is removed from the device of FIG. 1.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described later, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, following embodiments will be described in detail with reference to the accompanying drawings, and when the following embodiments are described with reference to the drawings, the same or corresponding components are given the same reference numerals, and repetitive descriptions thereof will be omitted.

As the present embodiments allow for various modifications, particular embodiments will be illustrated in the drawings and further described in the detailed description. The effects and features of the present embodiments and the accompanying methods thereof will become apparent from the following description of the contents, taken in conjunction with the accompanying drawings. However, the present embodiments are not limited to the embodiments disclosed below, but may be implemented in various forms.

In describing the present disclosure, a detailed description of known related arts will be omitted when it is determined that the gist of the present disclosure may be unnecessarily obscured.

In the following embodiments, singular forms are intended to include plural forms as well, unless the context clearly indicates otherwise. Although terms such as "first," "second," and the like may be used to describe various components, such components should not be limited to the above terms The terms are only used to distinguish one component from another.

In the following embodiments, terms such as "include" or "have" means that the features or components described in the specification are present, and the possibility that one or more other features or components will be added is not excluded in advance.

In the following embodiments, when a unit, region, or component is referred to as being formed on another unit, region, or component, it can be directly formed on the other unit, region, or component. That is, for example, intervening units, regions, or components may be present.

In the following embodiments, terms such as "connecting" or "coupling" two members do not necessarily mean a direct and/or fixed connection or coupling of the two members, unless the context clearly indicates otherwise, and do not preclude another members from being interposed between the two members.

Sizes of components in the drawings may be exaggerated or reduced for convenience of description. For example, since the size and thickness of each component shown in the drawings are arbitrarily illustrated for convenience of description, the following embodiments are not necessarily limited thereto.

First Embodiment

Figure 3:
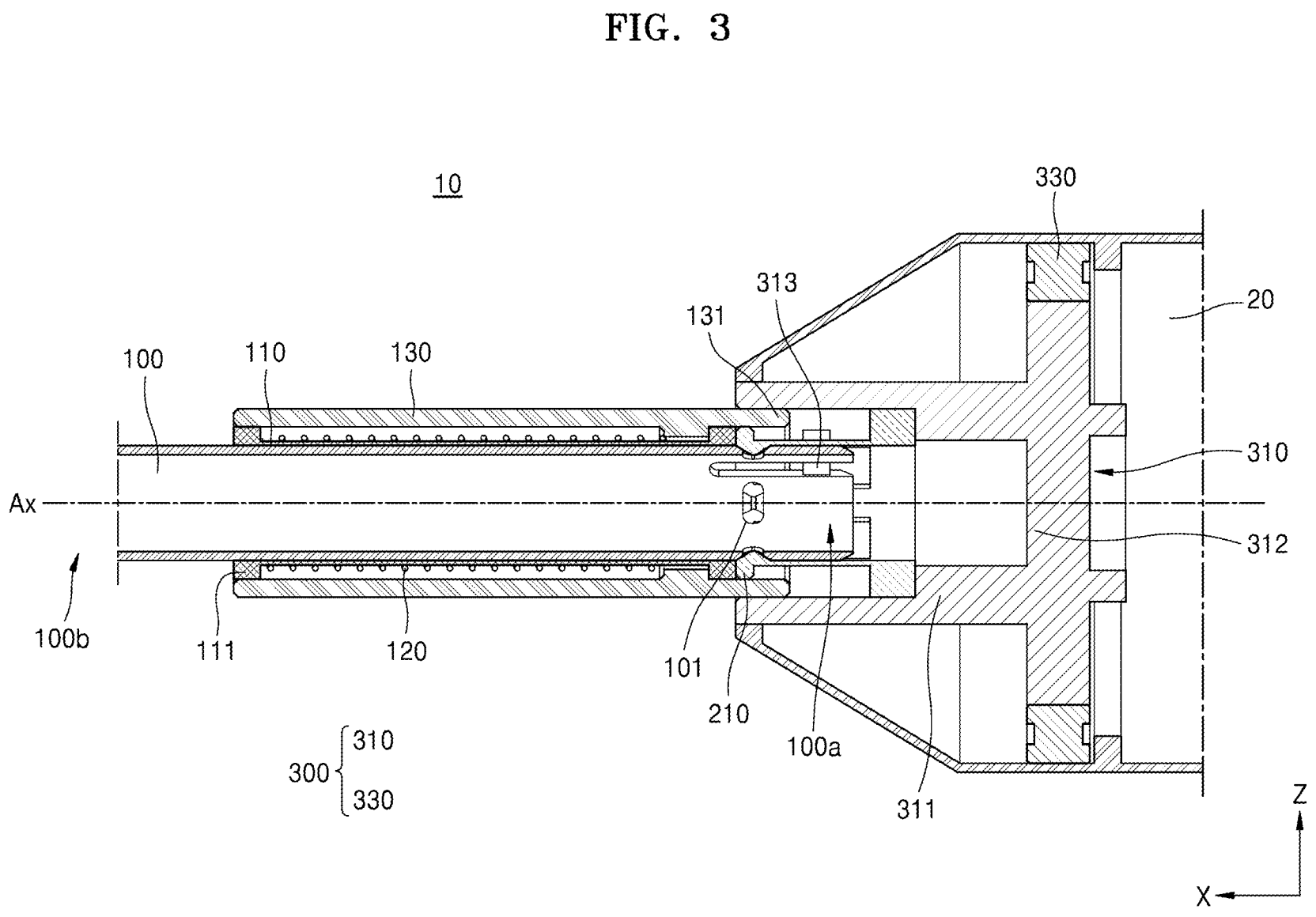
Figure 4:
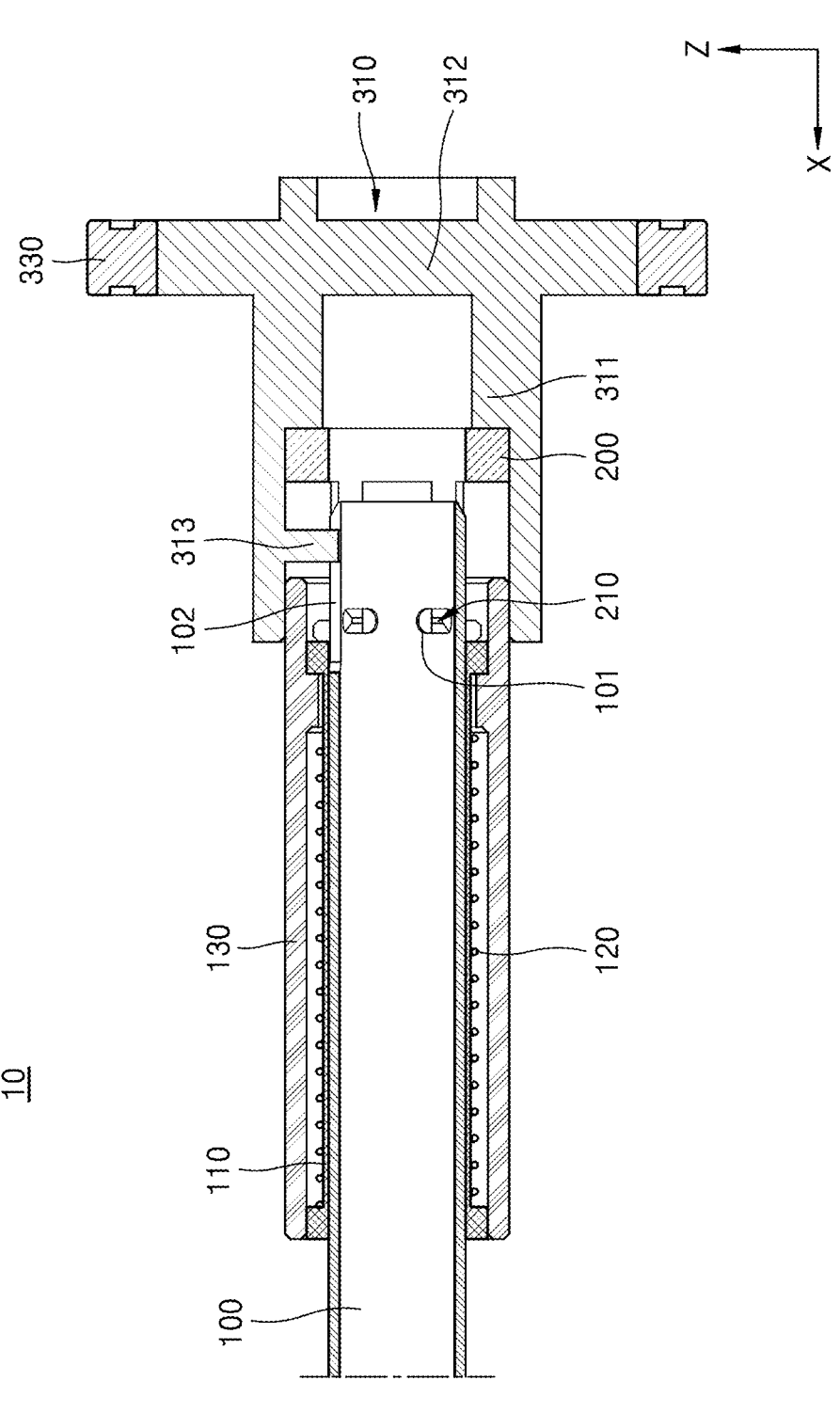
Figure 5:
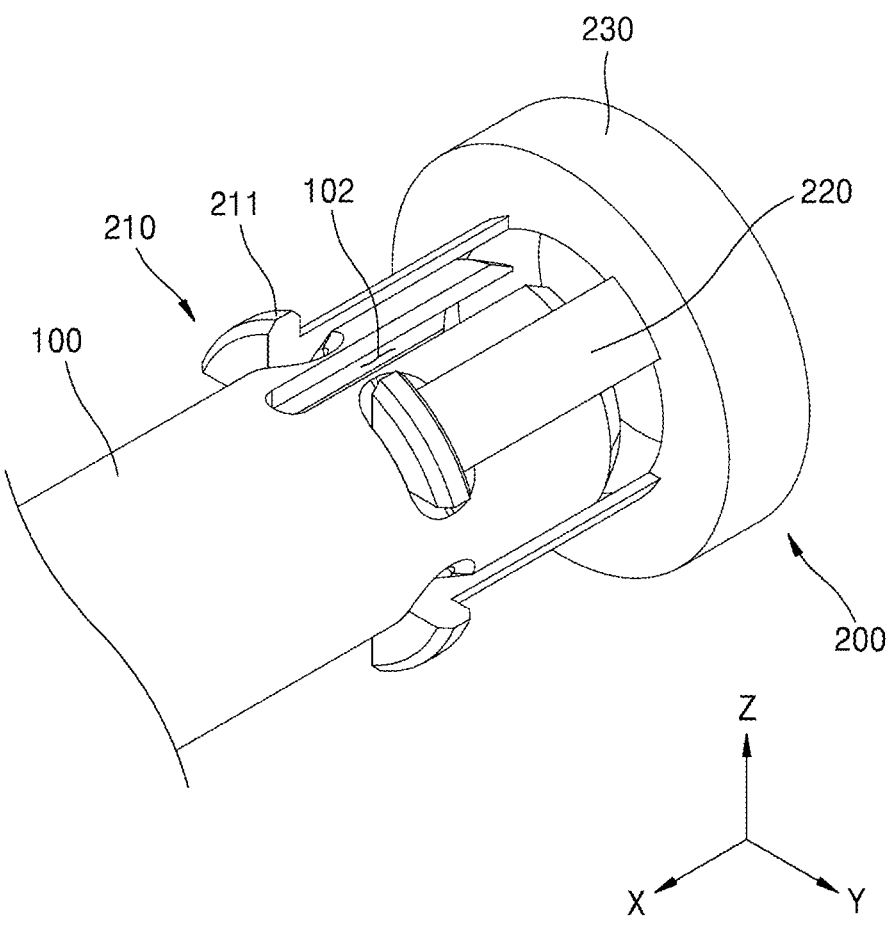
FIG. 5 is a perspective view illustrating a state in which the shaft and a latch member of the shaft attachment and detachment apparatus of FIG. 1 are coupled to each other.
Figure 6:
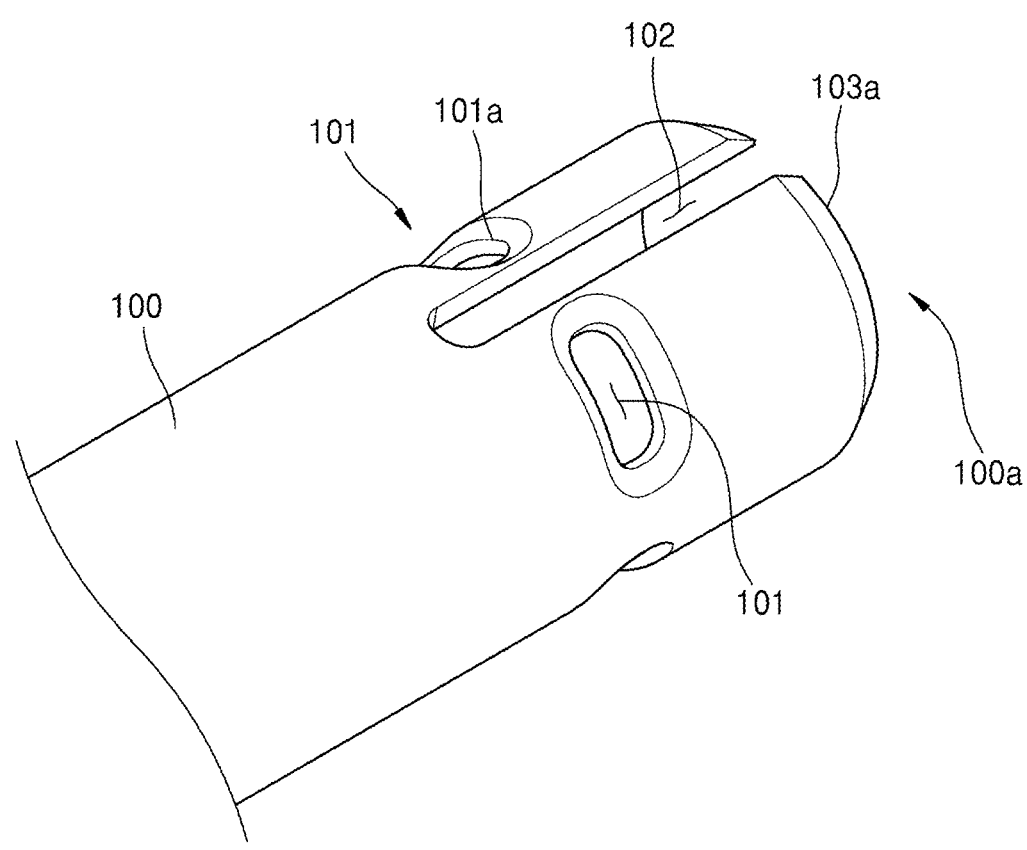
FIG. 6 is a perspective view illustrating the shaft of the shaft attachment and detachment apparatus of FIG. 1.

FIG. 1 is a perspective view illustrating a shaft attachment and detachment apparatus according to a first embodiment of the present disclosure and a device to which the shaft attachment and detachment apparatus is applied, and FIGS. 3 and 4 are side cross-sectional views illustrating the shaft attachment and detachment apparatus of FIG. 1. FIG. 5 is a perspective view illustrating a state in which a shaft and a latch member of the shaft attachment and detachment apparatus of FIG. 1 are coupled to each other. FIG. 6 is a perspective view illustrating the shaft of the shaft attachment and detachment apparatus of FIG. 1, and FIGS. 7 to 9 are views illustrating the latch member of the shaft attachment and detachment apparatus of FIG. 1.

Referring to FIGS. 1 to 9, a shaft attachment and detachment apparatus 10 according to the first embodiment of the present disclosure may include a shaft 100, a sleeve 130, a connector 300, and a latch member 200.

Here, the connector 300 is a connection part that is fixedly coupled to the device body 20 to which the shaft 100 is attached for use, enabling the shaft 100 to be coupled to the device body 20, and may include a connector base 310 and a bearing 330.

In describing the present disclosure, the device may be a medical device. Specifically, the medical device may include a connection member including a shaft-shaped coupling part. In addition, grooves may be formed on one end portion of the coupling part.

The connection member may have one end portion at which the coupling part is formed and the other end portion to which an end tool is coupled. Alternatively, the connection member itself may be formed as a shaft-shaped coupling part. The connection member may be fixedly coupled to the device body through the coupling part. Specifically, the connector base to be described later may be provided in the device body, and the coupling part may be inserted and fixed to the connector base to attach the connection member to the device body.

Here, the case in which the device is a medical device, specifically, a handle-type surgical device is described by way of example, but the concept of the present disclosure is not necessarily limited thereto, and it is of course possible that the present disclosure is applicable to any part of a device for attaching or detaching an instrument including a shaft-shaped structure to or from the device by simple linear movement.

The connector base 310 may include an insertion part 311 through which a portion of the shaft 100 is inserted, and a support part 312 coupled to the device body 20 by coming into contact with the bearing 330. The bearing 330 is formed in the size and shape corresponding to the shape of an inside of the device body 20, and the support part 312 may be entirely or partially in contact with the bearing 330. Alternatively, the support part 312 of the connector base 310 may be directly fixedly coupled inside the device body 20. In addition, the support part 312 may form a hollow to communicate with the insertion part 311 and the shaft 100. That is, the hollow formed in the support part 312 and a hollow formed in the insertion part 311 may be connected to each other to form a hole passing therethrough.

The insertion part 311 is formed to extend from the support part 312, and may be at least partially fixed to the device body 20 for support. That is, one end portion of the insertion part 311 may be fixed to the support part 312, and the other end portion thereof may be fixed to the device body 20.

In addition, the insertion part 311 is formed in a cylindrical shape with an empty inside, and may internally accommodate at least a portion of the shaft 100. In addition, the latch member 200, which will be described later, may be fixedly coupled to an inner circumferential surface of the insertion part 311. In addition, a protrusion 313, which protrudes from the inner circumferential surface toward the center of the insertion part 311, may be formed in the insertion part 311. That is, it may be said that the protrusion 313 is formed with a length sufficient to pass through a key groove 102 of the shaft 100, which will be described later, and serves as a kind of key to guide the position of the shaft 100 or restrict the rotation of the shaft 100. This will be described in detail later.

In describing the present disclosure, a portion close to the device body 20, that is, a portion close to the connector base 310 will be described as a proximal end 100a, and a portion farther from the device body 20, that is, a portion farther from the part into which the shaft 100 is inserted, will be described as a distal end 100b.

For example, the description will continue with reference to FIG. 1 by defining a portion of the shaft 100, which is close to the connector base 310, as the proximal end 100a of the shaft 100, and defining a portion of the shaft 100, which is farther from the connector base 310, i.e., close to the other end opposite the one end portion where the shaft 100 is inserted, as the distal end 100b of the shaft 100. In other words, the proximal end 100a of the shaft 100 may be described as a portion close to the latch member 200, and the distal end 100b of the shaft 100 may be described as a portion farther from the latch member 200.

Figure 7:
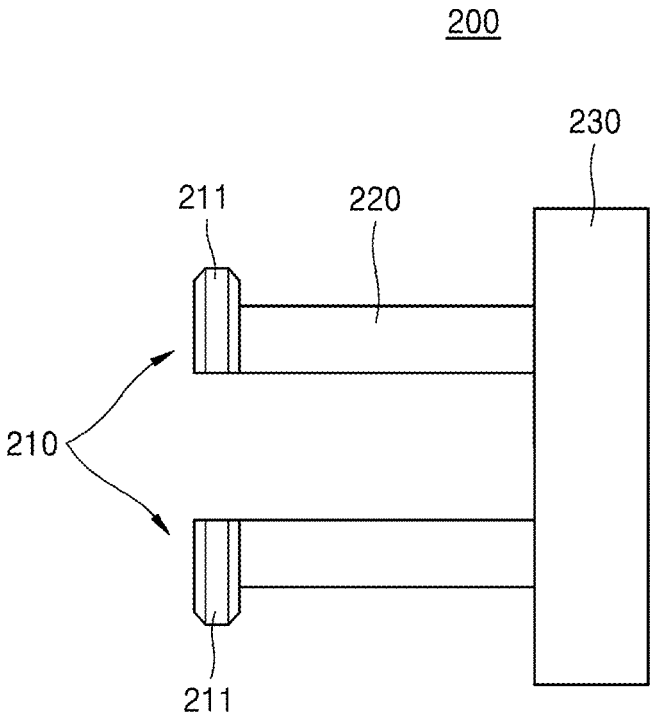
FIGS. 7 to 9 are views illustrating the latch member of the shaft attachment and detachment apparatus of FIG. 1.
Figure 8:
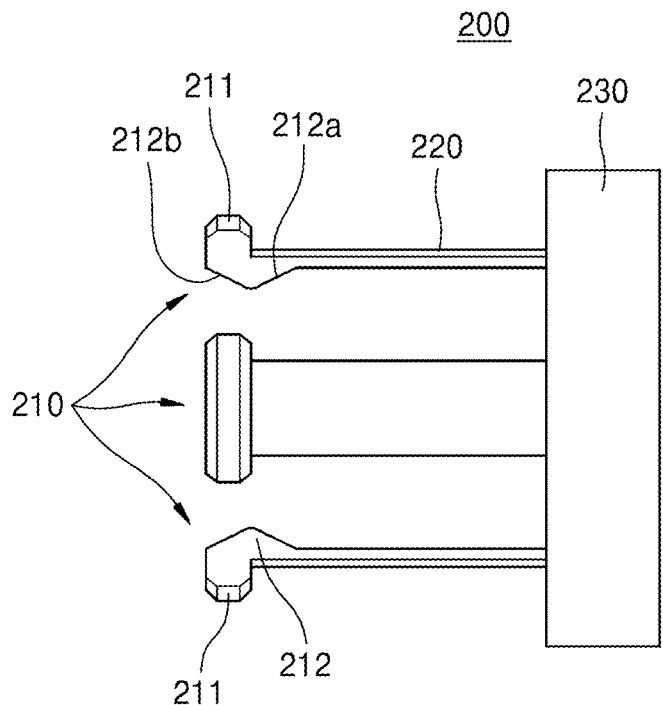
Figure 9:
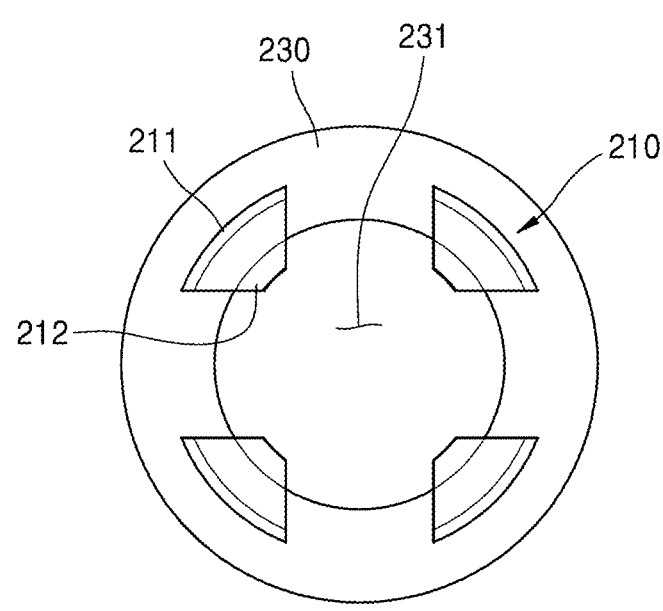

Referring to FIGS. 5 to 9, a groove 101 may be formed in one end portion of the shaft 100, which is inserted into the device body 20. Specifically, in the shaft 100, a plurality of grooves 101 may be formed at positions respectively corresponding to latches 210 of the latch member 200. For example, as shown in FIG. 7, the plurality of grooves 101 may be formed to be spaced apart from each other at regular intervals along an outer circumferential surface of the shaft 100. The groove 101 of the shaft 100 may be formed to accommodate the latch 210 of the latch member 200, which will be described later, so that the latch 210 is inserted into the groove 101. Each of the grooves 101 may be formed to have a width capable of accommodating at least a portion of the latch 210, and may be formed to have a predetermined depth from an outer surface to an inner surface of the shaft 100. In addition, the groove 101 may be formed in the shape of a hole passing through the outer surface and the inner surface of the shaft 100.

Here, the groove 101 of the shaft 100 may include a groove-inclined surface 101a formed such that a width of the groove decreases toward an inner surface from an outer surface of the shaft 100. That is, it may be said that the width of the groove 101 adjacent to the outer surface of the shaft 100 may be greater than the width of the groove 101 adjacent to the inner surface of the shaft 100. The groove-inclined surface 101a may be entirely or partially formed on a circumference of the groove 101. In particular, the groove 101 of the shaft 100 may include a portion formed such that a width thereof decreases toward the distal end 100b from the proximal end 100a. In other words, the groove 101 may be formed such that a depth on the distal end 100b side is greater than that at the proximal end 100a side when viewed in cross section.

By forming the inclined surface in the groove 101 as described above, when the latch 210 to be described later is coupled to the groove 101, the latch 210 may be gently moved along the inclined surface to be inserted into the groove 101.

Meanwhile, the key groove 102 may be formed on one end portion of the shaft 100, which is inserted into the device body 20. The key groove 102 may be formed in the shape of an elongated slit extending toward the distal end 100b of the shaft 100 from the end portion of the shaft 100. In addition, the key groove 102 may be formed to be located between the grooves 101 of the shaft 100 described above.

Here, the key groove 102 may be a portion into which the above-described protrusion of the connector base 310 is fitted. That is, the protrusion 313 protruding from the inner circumferential surface of the insertion part 311 of the connector base 310 toward the center may be fitted into the key groove 102 of the shaft 100.

Here, the protrusion 313 and the key groove 102 may guide the position of the shaft 100 when the shaft 100 is inserted into the connector base 310. In other words, when the shaft 100 is attempted to be inserted into the insertion part 311 of the connector base 310, the shaft 100 may not be inserted into the insertion part 311 if the key groove 102 is not aligned with the protrusion 313. In addition, the shaft 100 may be restricted from rotating around an axis thereof when the protrusion 313 is fitted into the key groove 102. Accordingly, when the latch member 200 is coupled to the shaft 100, the shaft 100 may be stably fixed to the device body 20 by restricting the rotation of the shaft 100 even if there is a gap between the latch 210 and the groove 101.

Meanwhile, the shaft 100 may include an elastic member housing 110. The elastic member housing 110 may be disposed between the outer circumferential surface of the shaft 100 and the sleeve 130 and may be fixedly coupled to the shaft 100. Specifically, the elastic member housing 110 may be disposed close to one end portion of the shaft 100 inserted into the device body 20. Specifically, the elastic member housing 110 may be disposed close to the grooves 101 of the shaft 100 to be described later.

In addition, the elastic member housing 110 may include an elastic member 120 disposed between the sleeve 130 and the elastic member housing 110. Here, the elastic member 120 may be a spring. Specifically, the elastic member housing 110 may be formed in the shape of a hollow elongated tube, similar to the shaft 100, and may be fixedly coupled to the shaft 100 by fitting onto the outer circumferential surface of the shaft 100. In addition, the elastic member 120 may be wound around so as to encircle the outer surface of the elastic member housing 110. That is, it may be said that the elastic member 120 is provided to pass through the elastic member housing 110. In other words, it may be said that an inner surface of the elastic member housing 110 is in contact with the outer surface of the shaft 100 and the outer surface of the elastic member housing 110 is in contact with the elastic member 120.

In addition, the elastic member housing 110 may include a support 111 to which the elastic member 120 is fixedly coupled and which supports the elastic member 120. The support 111 is formed along a circumference of the outer circumferential surface of the elastic member housing 110, and may be formed in a shape protruding in a direction away from a central axis of the shaft 100. Here, the support 111 may be located between both end portions of the elastic member housing 110. Alternatively, the support 111 may be formed at the end portion of the elastic member housing 110 on the distal end 100b side.

Here, one end portion of the elastic member 120 may be fixedly coupled to the support 111 of the elastic member housing 110, and the other end portion of the elastic member 120 may be in contact with the sleeve 130 to be described later. Specifically, the other end portion of the elastic member 120 may be in contact with, but not be fixedly coupled to, a locking part 132 of the sleeve 130. Here, the locking part 132 is a part formed to protrude from an inner surface of the sleeve 130 toward the elastic member housing 110, and may support the other end portion of the elastic member 120.

Alternatively, one end portion of the elastic member 120 may be in contact with, but not fixedly coupled to, the support 111, and the other end portion of the elastic member 120 may be fixedly coupled to the locking part 132 of the sleeve 130. Alternatively, one end portion and the other end portion of the elastic member 120 may be fixedly coupled to the support 111 and the locking part 132, respectively.

In addition, a step 112 protruding similar to the support 111 may be formed on an end portion of the elastic member housing 110 on the proximal end 100a side. In other words, the step 112 is formed along a circumference of an outer circumferential surface of the elastic member housing 110, and may be formed in a shape protruding in a direction away from the central axis of the shaft 100.

Meanwhile, the shaft 100 of the shaft attachment and detachment apparatus 10 according to the first embodiment of the present disclosure may include the sleeve 130. The sleeve 130 may be movable in an axial direction of the shaft 100 while surrounding at least a portion of the outer surface of the shaft 100. Specifically, the sleeve 130 may be formed in the shape of an elongated tube surrounding the outer surface of the elastic member housing 110. The sleeve 130 may surround the elastic member housing 110, and may not be fixedly coupled to the elastic member housing 110 in an axial direction. That is, the sleeve 130 may be movable toward the distal end 100b or the proximal end 100a of the shaft 100. In other words, since the sleeve 130 is not fixedly coupled to the elastic member housing 110 in the axial direction, the sleeve 130 may move in a longitudinal direction of the elastic member housing 110 along the outer surface of the elastic member housing 110.

The sleeve 130 may include the locking part 132 formed to protrude from the inner surface of the sleeve 130 toward the elastic member housing 110. The locking part 132 is formed on the inner surface of the sleeve 130 on the proximal end 100a side and may be formed along a circumference of an inner circumferential surface of the sleeve 130. That is, the locking part 132 may be formed in a band shape. Alternatively, the locking part 132 may be partially formed on the circumference of the inner circumferential surface of the sleeve 130.

As described above, the locking part 132 may support the other end portion of the elastic member 120. In addition, the locking part 132 may be a part that comes into contact with the step 112 of the elastic member housing 110 and interferes with the step 112. In other words, when the sleeve 130 moves toward the proximal end 100a of the shaft 100, the locking part 132 may interfere with the step 112 of the elastic member housing 110 to restrict the sleeve 130 from moving further to the proximal end 100a.

In addition, a certain region of an end portion of the sleeve 130 may form a portion that overlaps the grooves 101 of the shaft 100. An end portion 131 of the sleeve may be a portion formed to further extend toward the proximal end 100a of the shaft 100 from the portion where the locking part 132 of the sleeve 130 is formed. In other words, it may be said that the locking part 132 of the sleeve 130 may be formed to be spaced apart from the end portion of the sleeve 130 by a certain degree. In addition, a separation space may be formed between the end portion 131 of the sleeve and the shaft 100, and the latches 210 to be described later may be disposed in the separation space.

Here, defining a state in which an external force is not applied to the sleeve 130, i.e., a state before the sleeve 130 is moved, as an initial state, and the position of the sleeve 130 at this point as an initial position, a certain region of the end portion 131 of the sleeve may be in a state of overlapping the groove 101 of the shaft 100 in the initial position.

Meanwhile, the latch member 200 of the shaft attachment and detachment apparatus 10 according to the first embodiment of the present disclosure may include a body 230, legs 220, and the latches 210.

Here, the body 230 may be a part fixedly coupled to the connector base 310. Specifically, the body 230 may be formed in a shape corresponding to the inner circumferential surface of the insertion part 311 of the connector base 310 described above and fixedly coupled to the insertion part 311. Specifically, the body 230 may be formed in a cylindrical shape or a ring shape with a perforated center That is, the body 230 includes a through hole 231 at a center portion thereof, and the shaft 100 may be inserted through the body 230.

The leg 220 may be a part formed in a shape protruding from the body 230 toward of the shaft 100. Specifically, the leg 220 may be a part formed to extend toward the groove 101 along the outer circumferential surface of the shaft 100.

The legs 220 are disposed around the through hole 231 of the body 230 so as to be adjacent to or in contact with the outer circumferential surface of the shaft 100 when the shaft 100 is coupled to the latch member 200. In addition, a plurality of legs 220 may be disposed to be spaced apart from each other and symmetrically about a central axis Ax of the shaft 100. In addition, the latch 210 may be formed on an end portion of the leg 220.

The latch 210 may include an inner side protrusion 212 inserted into at least one region of the groove 101 of the shaft 100, and an outer side protrusion 211 formed on the opposite side of the inner side protrusion 212. That is, it may be said that the inner side protrusion 212 is a portion that is formed in the latch 210 and protrudes toward the central axis AX of the shaft 100, and the outer side protrusion 211 is a portion that is formed in the latch 210 and protrudes outward from the central axis AX of the shaft 100.

The inner side protrusion 212 may include a first inclined surface 212a formed such that a height on the distal end 100b, which is in a direction away from the connector base 310 is higher than that on the proximal end 100a, which is in a direction close to the connector base 310. In addition, the inner side protrusion 212 may further include a second inclined surface 212b, which is formed to be higher on the proximal end 100a side than on the distal end 100b side. In other words, it may be said that the most protruding portion of the inner side protrusion 212 of the latches 210 is the portion where the first inclined surface 212a and the second inclined surface 212b meet or are adjacent to each other.

Hereinafter, an operation mechanism of the shaft attachment and detachment apparatus 10 will be described.

Figure 10:
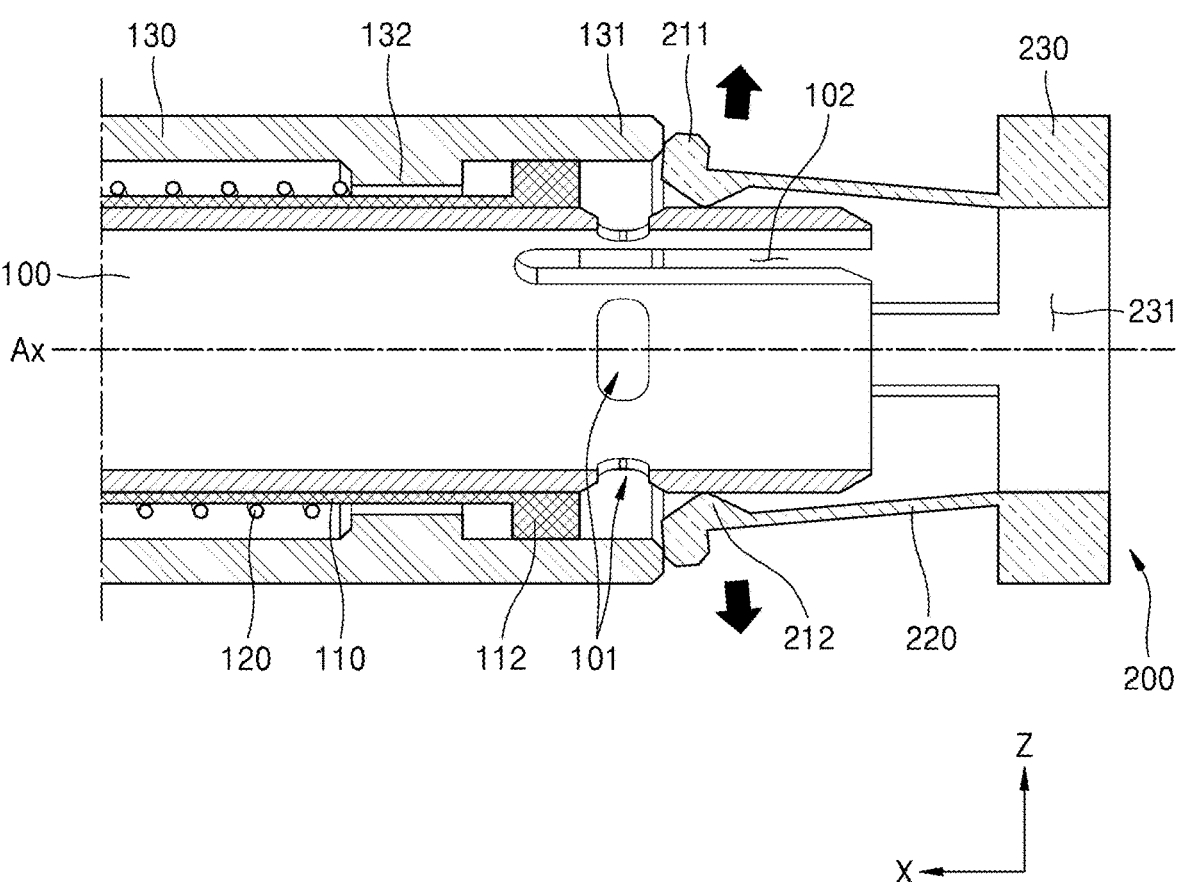
FIGS. 10 and 11 are views for describing an operation mechanism of the shaft attachment and detachment apparatus of FIG. 1.
Figure 11:
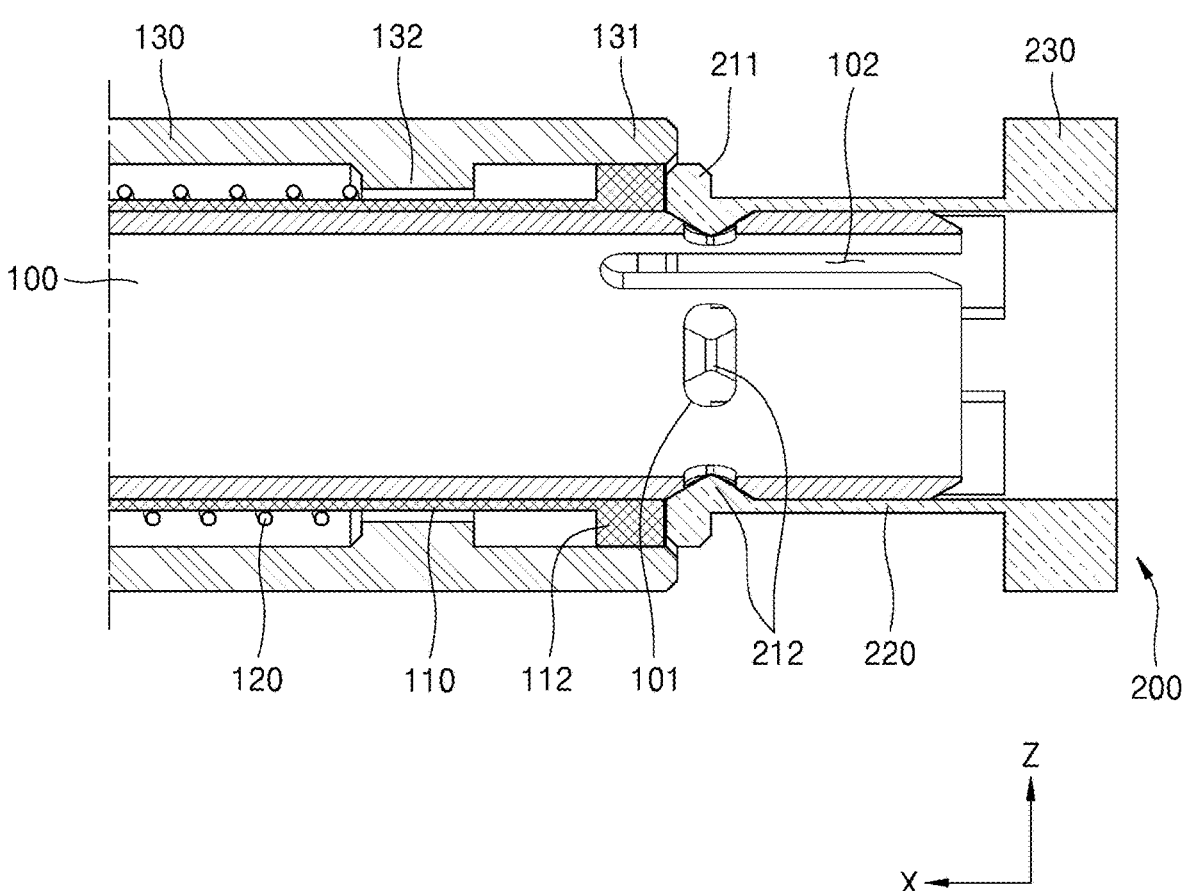

FIGS. 10 and 11 are views for describing the operation mechanism of the shaft attachment and detachment apparatus of FIG. 1.

Referring to FIG. 10, when the shaft 100 is inserted toward the connector base 310 of the device body 20, the shaft 100 may come into direct contact with the latch member 200. Specifically, the end portion of the shaft 100 comes into contact with the latches 210, and the inner side protrusions 212 of the latches 210 may interfere with the shaft 100. At this time, the legs 220 respectively connected to the latches 210 may have elasticity and thus may be spread in a direction away from the central axis AX of the shaft 100. That is, as shown in the drawings, the outer circumferential surface of the shaft 100 and the inner side protrusions 212 of the latches 210 interfere with each other, causing the latches 210 to elastically deform in arrow directions At this time, the outer side protrusions 211 of the latches 210 may come into contact with the end portion of the sleeve 130, and the end portion 131 of the sleeve 130 may interfere with the outer side protrusions 211.

Here, as the shaft 100 is inserted toward the connector base 310, the end portion 131 of the sleeve 130 may apply a force to the outer side protrusions 211 of the latch 210. In other words, it may be said that the outer side protrusions 211 apply a force to the end portion 131 of the sleeve 130. Accordingly, the sleeve 130 may slidably move toward the distal end 100*b* of the shaft 100 in a direction opposite to an insertion direction of the shaft 100. That is, the sleeve 130 may axially move away from the groove 101 of the shaft 100 from the initial position thereof.

Accordingly, as shown in FIG. 11, when the shaft 100 is further inserted toward the connector base 310, the sleeve 130 covering the groove 101 in the initial state may no longer cover the groove 101.

In addition, when the inner side protrusions 212 of the latches 210 reach the position of the grooves 101 of the shaft 100, the inner side protrusions 212 may be inserted into the grooves 101 by the force of the elastically deformed legs 220 attempting to return to the original state thereof. As at least one region of the inner side protrusion 212 is inserted into the groove 101 of the shaft 100 as described above, the latch 210 may be coupled to the groove 101. In addition, as the latch 210 is coupled to the groove 101, the outer side protrusion 211 may no longer interfere with the end portion 131 of the sleeve. That is, an external force may not be applied to the sleeve 130.

Meanwhile, when the sleeve 130 slidably moves toward the distal end 100*b* along the outer surface of the elastic member housing 110, the locking part 132 of the sleeve 130 may press the elastic member 120. That is, it may be said that the elastic member 120 disposed between the support 111 of the elastic member housing 110 and the locking part 132 of the sleeve 130 is compressed as the locking part 132 of the sleeve 130 moves toward the distal end 100*b*, and thus a separation distance between the support 111 and the locking part 132 is reduced.

Here, the compressed elastic member 120 may provide an elastic force to the locking part 132 in a direction of pushing the sleeve 130 toward the proximal end 100*a*. Thus, when the external force that the sleeve 130 receives from the latches 210 in the direction of the distal end 100*b* is removed, the sleeve 130 may move back toward the proximal end 100*a* by the force that the sleeve 130 receives from the elastic member 120 in the direction of the proximal end 100*a*.

In addition, when the sleeve 130 moves toward the proximal end 100*a* and returns to the initial position, the end portion 131 of the sleeve may cover the latch 210. That is, the latch 210 may be in a state located between the end portion 131 of the sleeve and the groove 101.

Depending on the relationship between the forces acting on the elastic member 120 of the elastic member housing 110 and the sleeve 130 as described above, the sleeve 130 may move along the axial direction of the shaft 100, and the coupled state of the latches 210 and the grooves 101 is changeable depending on the position of the sleeve 130 disposed in the shaft 100. For example, the axially moving sleeve 130 may restrict the uncoupling of the latches 210 from the grooves 101 by restricting the latches 210 from being separated from the grooves 101 of the shaft 100.

Specifically, in a state in which the end portion 131 of the sleeve covers the latches 210, the latches 210 may be restricted from spreading away from the central axis AX of the shaft 100.

The latches 210 coupled to the grooves 101 are in a state coupled to the shaft 100 with a certain degree of coupling force, but when the end portion 131 of the sleeve does not cover the latches 210, the latches 210 may be separated from the grooves 101 when an external force is applied to the shaft 100. However, since the end portion 131 of the sleeve covers the latches 210 as described above, the latches 210 will not spread, and thus the state in which the latches 210 are coupled to and the grooves 101 may be maintained.

Meanwhile, the coupling between the latch 210 and the groove 101 may be released by applying an external force to the sleeve 130. That is, by moving the sleeve 130 toward the distal end 100*b*, i.e., in a direction away from the connector base 310, the latches 210 may be exposed to the outside of the sleeve 130 and may be uncoupled from the grooves 101. In other words, by pulling the sleeve 130 toward the distal end 100*b*, i.e., in a direction away from the connector base 310, the sleeve 130 does not cover the latches 210, and the latches 210 may be separated from the grooves 101.

As described above, while the sleeve 130 does not cover the latches 210 coupled to the grooves 101, the latches 210 may be uncoupled from the grooves 101.

When the sleeve 130 is pulled toward the distal end 100*b* of the shaft 100 by applying an external force to the sleeve 130, the sleeve 130 may slidably move toward the distal end 100*b* along the outer surface of the elastic member housing 110, and the locking part 132 of the sleeve 130 may press the elastic member 120. That is, it may be said that the elastic member 120 disposed between the support 111 of the elastic member housing 110 and the locking part 132 of the sleeve 130 is compressed as the locking part 132 of the sleeve 130 moves toward the distal end 100*b*, and thus, a separation distance between the support 111 and the locking part 132 is reduced.

At this time, when the sleeve 130 is continuously pulled, the latches 210 may spread, allowing the shaft 100 to be withdrawn. Specifically, the pulling force may be transmitted to the shaft 100 by a compressive force transmitted to the elastic member 120 when pulling the sleeve 130. Alternatively, the sleeve 130 may slidably move to the distal end 100*b* side by a certain degree and then interfere with a step of the elastic member housing 110 to directly transmit the force to the elastic member housing 110 and the shaft 100. In other words, by pulling the sleeve 130, the force may be transmitted to the shaft 100, and the latches 210 may be spread and uncoupled from the grooves 101 by the force with which the shaft 100 is withdrawn.

As a result, it is possible to achieve a structure in which the shaft 100 is automatically attached to the device body 20 by a user simply grasping the shaft 100 and pushing the shaft 100 toward the connector base 310, and even when an external force is applied to the shaft 100 during use, the shaft 100 does not detach from the device body 20, and the coupling between the shaft 100 and the device body 20 may be released only by intentionally grasping and pulling the sleeve 130. In addition, the attachment and detachment of the shaft 100 may be facilitated as the user simply needs to grasp the sleeve 130 with one hand and pull the sleeve 130.

Modified Example of First Embodiment

Hereinafter, a latch member 600 and a sleeve 140 of a shaft attachment and detachment apparatus according to a modified example of the first embodiment of the present disclosure will be described. Here, the shaft attachment and detachment apparatus according to the modified example of the first embodiment of the present disclosure is different from the shaft attachment and detachment apparatus 10 according to the first embodiment of the present disclosure described above in that the shape of the latch member 600 and the sleeve 140 is different.

Figure 12:
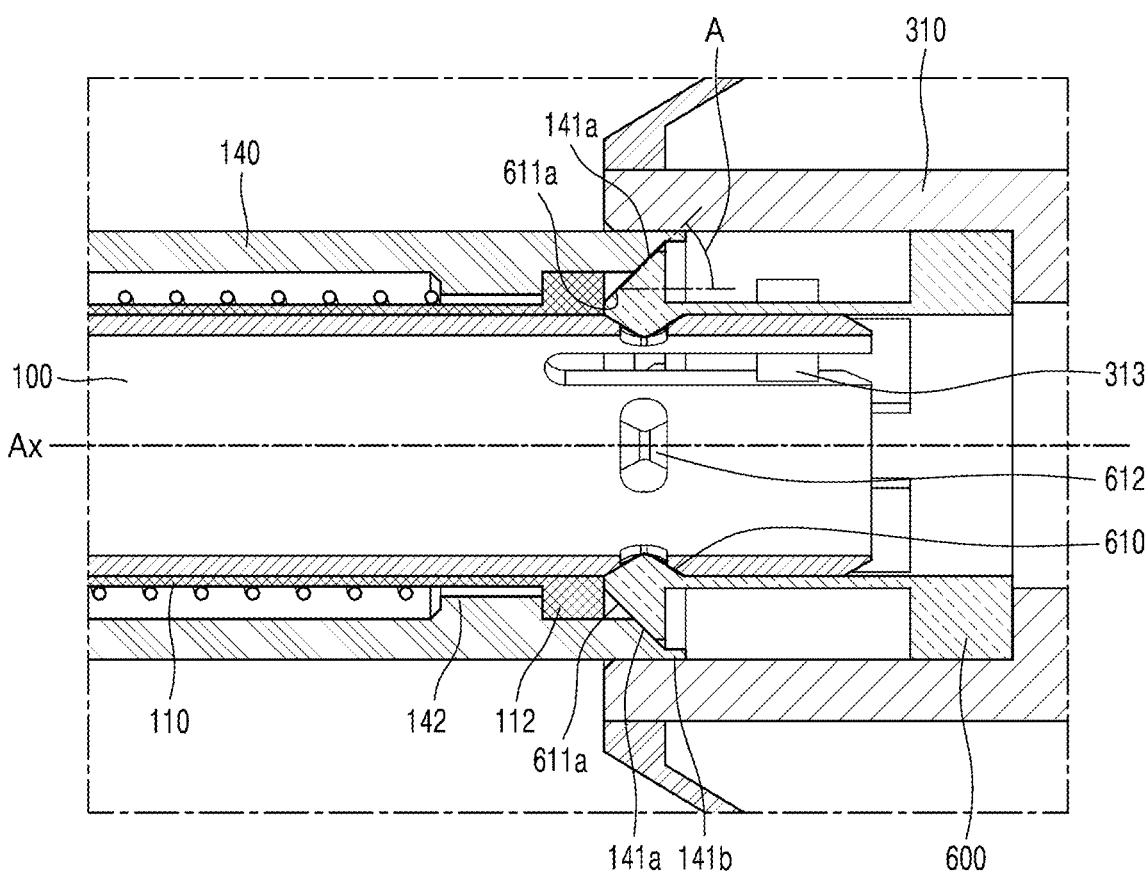
FIG. 12 is a side cross-sectional view illustrating a shaft attachment and detachment apparatus according to a modified example of the first embodiment of the present disclosure.
Figure 12:
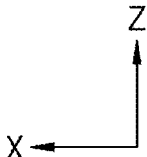
Figure 13:
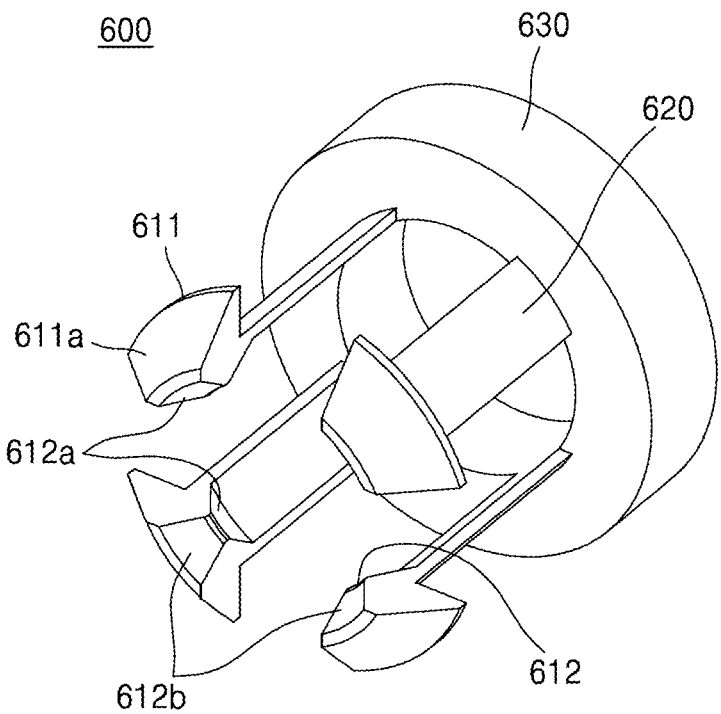
FIGS. 13 and 14 are views illustrating a latch member of the shaft attachment and detachment apparatus of FIG. 12.
Figure 14:
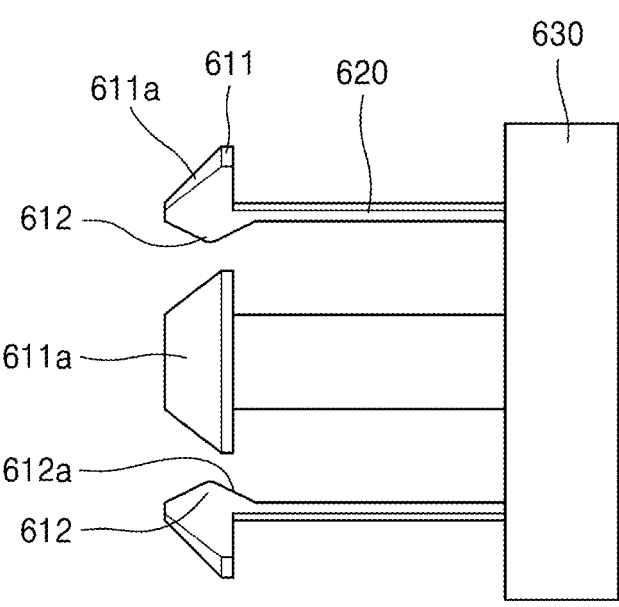

FIG. 12 is a side cross-sectional view illustrating the shaft attachment and detachment apparatus according to the modified example of the first embodiment of the present disclosure, and FIGS. 13 and 14 are views illustrating the latch member 600 of the shaft attachment and detachment apparatus of FIG. 12.

Referring to FIGS. 12 to 14, the latch member 600 of the shaft attachment and detachment apparatus according to the modified example of the first embodiment of the present disclosure may include a body 630, legs 620, and latches 610. The body 630 and the legs 620 are substantially the same as the body 230 and the legs 220 of the first embodiment of the present disclosure, and thus detailed descriptions thereof will be omitted herein.

Each of the latches 610 may include an inner side protrusion 612 inserted into at least one region of the groove 101 of the shaft 100, and an outer side protrusion 611 formed on the opposite side of the inner side protrusion 612. That is, it may be said that the inner side protrusion 612 is a portion that is formed in the latch 610 and protrudes toward the central axis AX of the shaft 100, and the outer side protrusion 611 is a portion that is formed in the latch 610 and protrudes outward from the central axis AX of the shaft 100.

Here, the inner side protrusion 612 may include a first inclined surface 612a formed such that a height on the distal end 100b, which is in a direction away from the connector base 310 is higher than that on the proximal end 100a, which is in a direction close to the connector base 310. In addition, the inner side protrusion 612 may further include a second inclined surface 612b, which is formed to be higher on the proximal end 100a side than on the distal end 100b side. In other words, it may be said that the most protruding portion of the inner side protrusion 612 of the latches 610 is the portion where the first inclined surface 212a and the second inclined surface 612b meet or are adjacent to each other.

Meanwhile, the outer side protrusion 611 may include a third inclined surface 611a formed such that a height on the proximal end 100a side, which is in a direction away from the connector base 310, is higher than that on the distal end 100b side, which is in a direction close to the connector base 310.

Meanwhile, the sleeve 140 may include a fourth inclined surface 141a, which corresponds to the third inclined surface 611a, at one end portion thereof facing the latch 610.

When the shaft 100 is inserted toward the connector base 310 of the device body (not shown), the shaft 100 may come into direct contact with the latch member 600. Specifically, the end portion of the shaft 100 comes into contact with the latches 610, and the inner side protrusions 612 of the latches 610 may interfere with the shaft 100. At this time, the legs 620 respectively connected to the latches 610 may have elasticity and thus may be spread in a direction away from the central axis AX of the shaft 100. At this time, the outer side protrusions 611 of the latches 610 may come into contact with the end portion of the sleeve 140, and the end portion 141 of the sleeve 140 may interfere with the outer side protrusions 611.

Here, when the outer side protrusion 611 of the latch 610 comes into contact with the end portion of the sleeve 140, the third inclined surface 611a is in contact with the fourth inclined surface 141a, and the fourth inclined surface 141a may press the third inclined surface 611a toward the center of the shaft 100.

As described above, since the elastic member 120 of the elastic member housing 110 applies a force pushing the sleeve 140 toward the proximal end 100a, the fourth inclined surface 141a formed at the end portion of the sleeve 140 presses the third inclined surface 611a of the outer side protrusion 611.

In addition, by covering the latches 610 by the end portion of the sleeve 140 while the latches 610 are coupled to the grooves 101 of the shaft 100, it is possible to restrict the latches 610 from spreading. At this time, as the fourth inclined surface 141a of the sleeve 140 presses the third inclined surface 611a while being in contact with the third inclined surface 611a of the outer side protrusion 611, it is possible to effectively restrict the latches 610 from spreading. Here, as an inclination angle A of the third inclined surface 611a decreases, less force is required to prevent the latches 610 from spreading. That is, the elastic member 120 applies a force pushing the sleeve 140 toward the proximal end 100a, causing the fourth inclined surface 141a of the sleeve 140 to press the third inclined surface 611a, and at this time, less force can be applied to press the third inclined surface 611a.

In addition, unlike the shaft attachment and detachment apparatus 10 according to the first embodiment of the present disclosure, in the shaft attachment and detachment apparatus according to the modified example of the first embodiment of the present disclosure, the end portion 141 of the sleeve is in contact with the latch 610 by a pressurized force, so that clearance between the end portion 141 of the sleeve and the latches 610 may be automatically absorbed, thereby facilitating tolerance management during manufacturing and assembly.

Meanwhile, the sleeve 140 may include a locking protrusion 141b formed to extend from the fourth inclined surface 141a and be parallel to the shaft 100. Specifically, it may be said that the fourth inclined surface 141a is formed to begin at a portion adjacent to an inner surface of the sleeve 140, extend to a portion close to an outer surface of the sleeve 140, and change in angle at an end portion of the sleeve 140 at which where the fourth inclined surface 141a ends, thereby forming the locking protrusion 141b.

That is, it may be said that the locking protrusion 141b may be formed to extend in a longitudinal direction of the sleeve 140 without substantially forming an inclination angle, unlike the fourth inclined surface 141a forming an inclination angle corresponding to the third inclined surface 611a.

The sleeve 140 including the locking protrusion 141b may restrict further spreading of the latches 610 by interfering with the locking protrusion 141b, even after some of the latches 610 have spread, overcoming the force applied by the fourth inclined surface 141a.

Meanwhile, the shaft attachment and detachment apparatus 10 described above may be divided into a device attachment and detachment module provided in the device body 20 and a shaft attachment and detachment module provided in the shaft 100. Here, the device attachment and detachment module is a module provided in the device body 20 to attach and detach the shaft 100 to/from the device body 20, and for example, the device attachment and detachment module may include the connector base 310 and the latch member 200. In addition, the shaft attachment and detachment module is a module provided in the shaft 100 to attach and detach the shaft 100 to/from the device body 20, and for example, the shaft attachment and detachment module may include the sleeve 130 and the elastic member housing 110.

Second Embodiment

Hereinafter, a shaft attachment and detachment apparatus 1010 according to a second embodiment of the present disclosure will be described.

Figure 15:
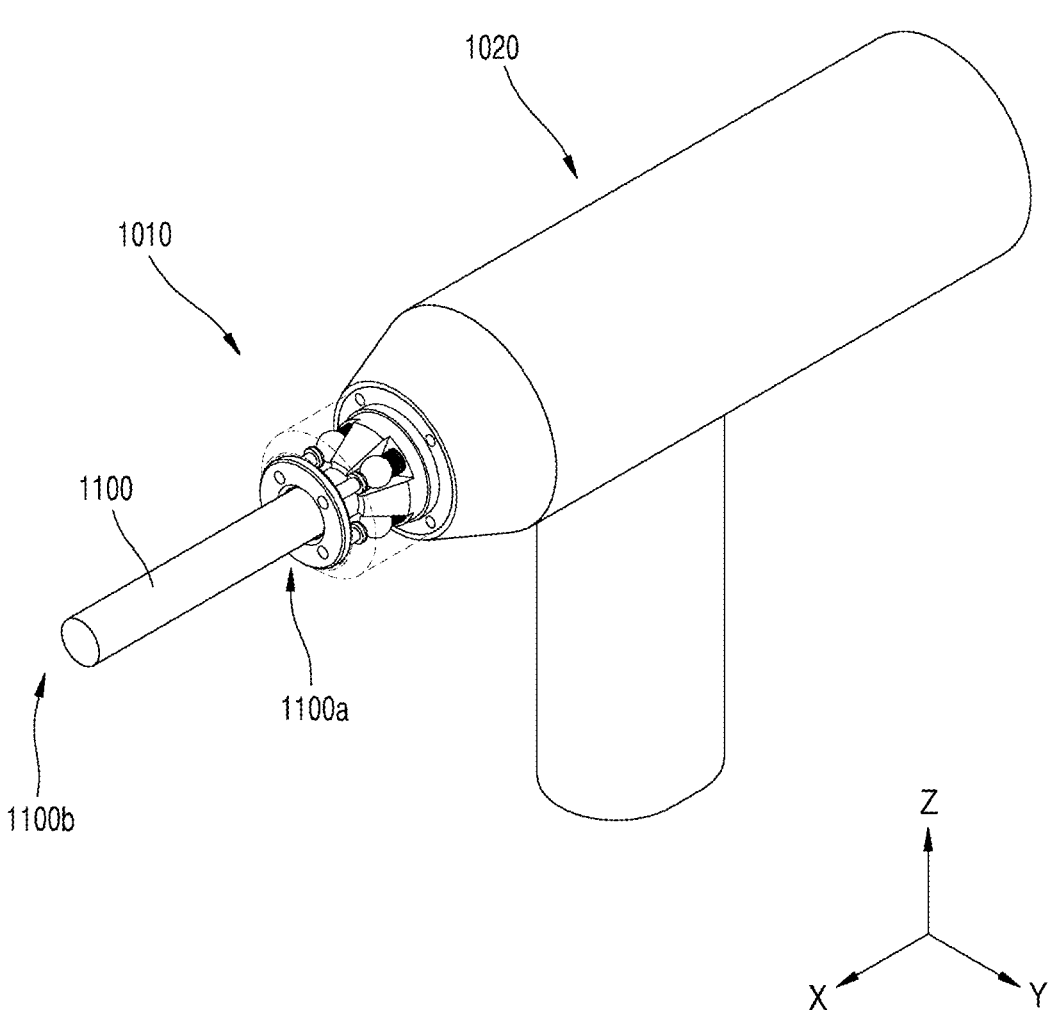
FIG. 15 is a perspective view illustrating a shaft attachment and detachment apparatus according to a second embodiment of the present disclosure and a device to which the shaft attachment and detachment apparatus is applied.
Figure 16:
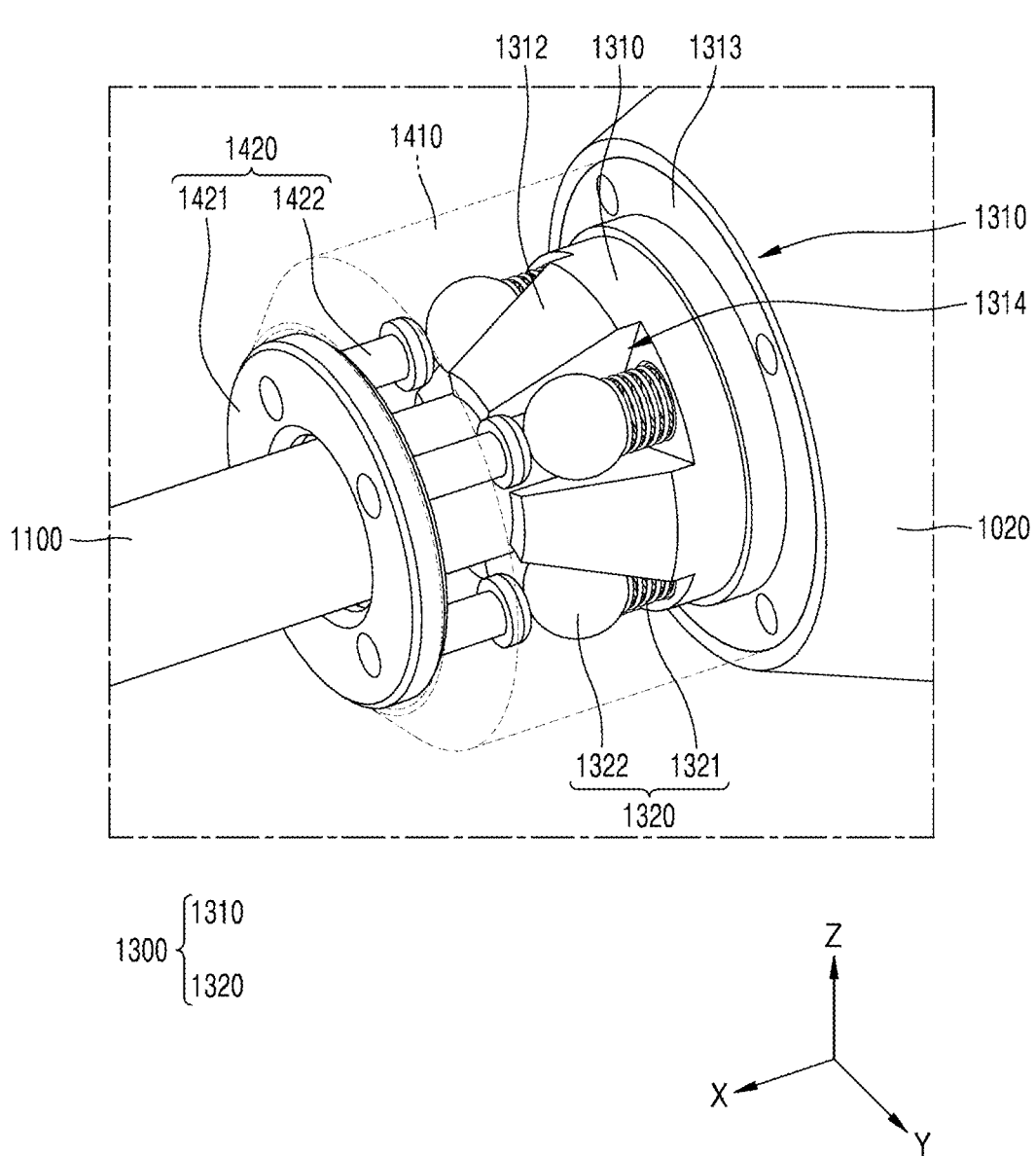
FIG. 16 is an enlarged perspective view illustrating the shaft attachment and detachment apparatus of FIG. 15.
Figure 17:
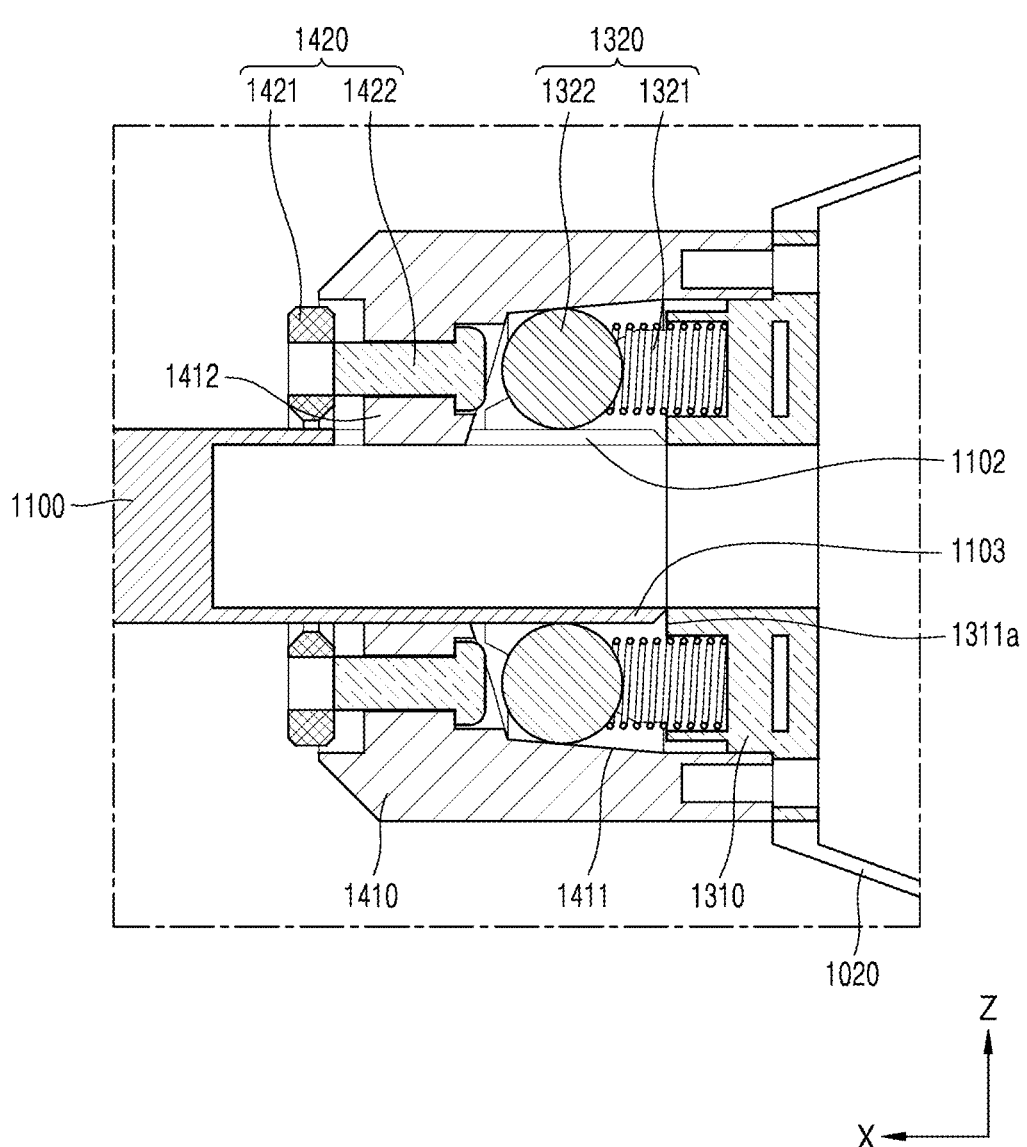
FIG. 17 is a side cross-sectional view illustrating the shaft attachment and detachment apparatus of FIG. 15.
Figure 18:
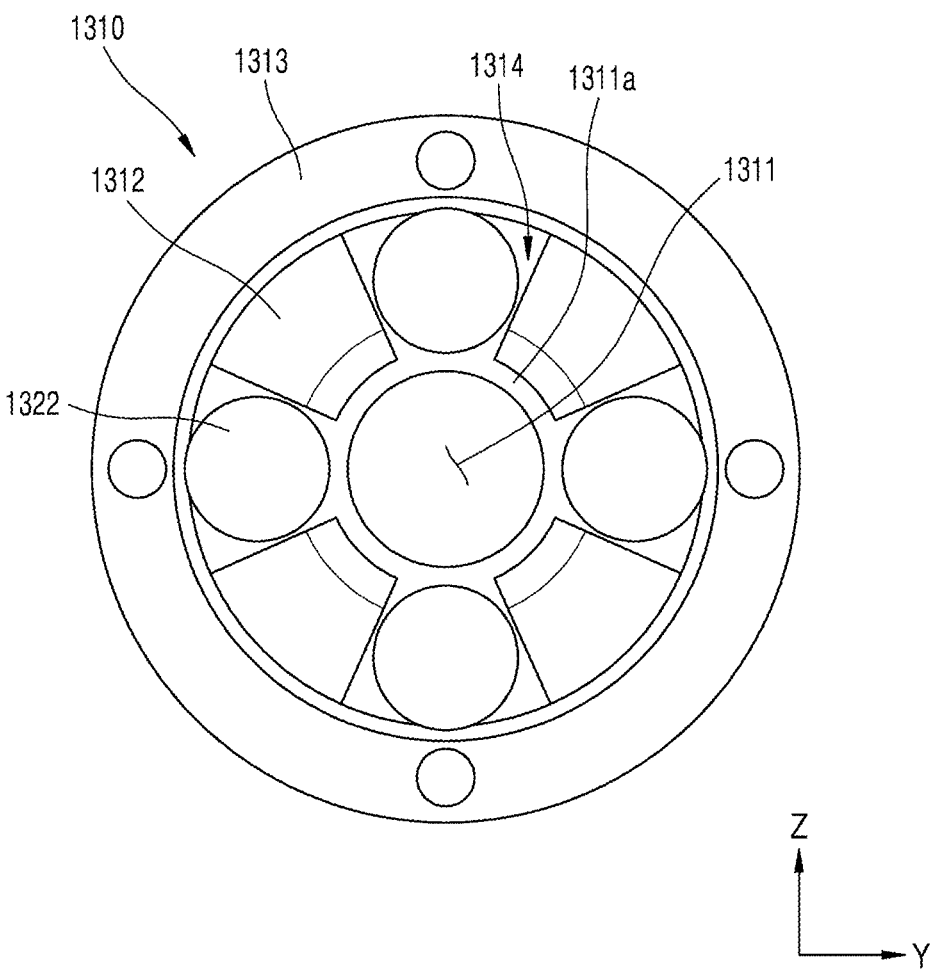
FIG. 18 is a plan view illustrating a connector base of FIG. 15.

FIG. 15 is a perspective view illustrating the shaft attachment and detachment apparatus according to the second embodiment of the present disclosure and a device to which the shaft attachment and detachment apparatus is applied, and FIG. 16 is an enlarged perspective view illustrating the shaft attachment and detachment apparatus of FIG. 15. FIG. 17 is a side cross-sectional view illustrating the shaft attachment and detachment apparatus of FIG. 15, and FIG. 18 is a plan view illustrating a connector base of FIG. 15.

Referring to FIGS. 15 to 18, the shaft attachment and detachment apparatus according to the second embodiment of the present disclosure may include a shaft 1100, a connector base 1310, a cover 1410, a reaction force member 1320, and a pusher member 1420.

The connector base 1310 is a connection part that is fixedly coupled to the device body 1020 to which the shaft 1100 is attached for use, enabling the shaft 1100 to be coupled to the device body 1020, and may include the reaction force member 1320, which will be described later and is disposed thereon. Here, a component encompassing the connector base 1310 and the reaction force member 1320 may be referred to as a connector 1300.

In describing the present disclosure, a device may be a medical device. Specifically, the medical device may include a connection member including a shaft-shaped coupling part.

The connection member may have one end portion at which the coupling part is formed and the other end portion to which an end tool is coupled. Alternatively, the connection member itself may be formed as a shaft-shaped coupling part. The connection member may be fixedly coupled to the device body through the coupling part. Specifically, the connector base to be described later may be provided in the device body, and the coupling part may be inserted and fixed to the connector base to attach the connection member to the device body.

Here, the case in which the device is a medical device, specifically, a handle-type surgical device is described by way of example, but the concept of the present disclosure is not necessarily limited thereto, and it is of course possible that the present disclosure is applicable to any part of a device for attaching or detaching an instrument including a shaft-shaped structure to or from the device by simple linear movement.

The connector base 1310 includes a support 1313 fixedly coupled to the device body 1020, and the support 1313 may internally form a through hole 1311 communicating with an inside of the device body 1020. In addition, in a state in which the shaft 1100 is attached to the connector 1300, a hollow in the shaft 1100 may communicate with the through hole 1311 of the support 1313.

Meanwhile, when the shaft 1100 is inserted into the connector 1300, the shaft 1100 may be in contact with the support 1313 of the connector base 1310. Specifically, one end portion of the shaft 1100 may be in contact with a boundary surface 1311a of the support 1313 which is a plane perpendicular to the shaft 1100. Specifically, it may be said that one end portion of the shaft 1100 is in surface contact with the boundary surface 1311a around the through hole 1311. Here, the size of the through hole 1311 may be equal to or less than an outer diameter of the shaft 1100.

The connector base 1310 may include a guide part 1312 formed on the support 1313. The guide part 1312 may be formed to protrude from the boundary surface 1311a of the support 1313 in a direction away from the device body 1020. A plurality of guide parts 1312 may be formed, and the plurality of guide parts 1312 may be disposed to surround the through hole 1311 and formed to protrude from the support 1313. That is, the plurality of guide parts 1312 may be shaped to surround an outer surface of the shaft 1100 while the shaft 1100 is inserted into the connector 1300. Here, the guide parts 1312 may serve to guide the shaft 1100 inserted into the connector 1300. In addition, the plurality of guide parts 1312 may be spaced apart from each other to serve as separation walls. In other words, it may be said that a separation space may be formed between the guide parts 1312. In addition, the reaction force member 1320 to be described later may be disposed in a separation space 1314 between the guide parts 1312. In addition, the guide parts 1312 may guide the movement of the reaction force member 1320.

Meanwhile, the shaft attachment and detachment apparatus 1010 according to the second embodiment of the present disclosure may include the cover 1410. The cover 1410 may be formed to be coupled to the connector base 1310 and may include an inner side surface therein. The cover 1410 may be formed to internally accommodate the connector base 1310 and the reaction force member 1320. In addition, the cover 1410 may internally form a hollow so that the shaft 1100 may be inserted therethrough. In addition, the pusher member 1420 to be described later may be accommodated in the cover 1410.

The cover 1410 may form an inner inclined surface 1411 such that a space inside the cover 1410 formed by the inner side surface becomes narrower in a direction away from the connector base 1310. In other words, it may be said that the inner side surface of the cover 1410 is formed such that the portion at a distal end side, which is far from the connector base 1310, is closer to the shaft 1100 than the portion at a proximal end side, which is closer to the connector base 1310.

Here, the inner inclined surface 1411 may guide at least a portion of the reaction force member 1320 to move toward a central axis of the shaft 1100. This will be described in detail later.

Meanwhile, a protrusion 1412 protruding toward the shaft 1100 may be formed in the cover 1410. In addition, a key groove 1102 may be formed in one end portion of the shaft 1100, which is inserted into the connector 1300.

The key groove 1102 may be formed in the shape of an elongated slit extending toward the distal end of the shaft 1100 from the end portion of the shaft 1100. When the shaft 1100 is inserted into the connector base 1310, the protrusion 1412 may be fitted into the key groove 1102. Accordingly, the shaft 1100 may be restricted from rotating around an axis while coupled to the connector 1300.

Meanwhile, the reaction force member 1320 is disposed between the connector base 1310 and the cover 1410, and may be formed to be in contact with the inner side surface of the cover 1410 at least once. Specifically, the reaction force member 1320 may be disposed in the separation space 1314 between the guide parts 1312 of the connector base 1310 described above. In addition, a plurality of reaction force members 1320 may be disposed, and the plurality of reaction force members 1320 may be disposed symmetrically with respect to the shaft 1100.

The reaction force member 1320 may include an elastic member 1321 and a friction member 1322. Here, one end portion of the elastic member 1321 may be fixedly coupled to the connector base 1310, and the other end portion of the elastic member 1321 may be coupled to the friction member 1322.

Here, the elastic member 1321 may be compressed by pressing the friction member 1322, and the elastic member 1321 may provide an elastic force in a direction of pushing the friction member 1322 toward the inner side surface of the cover 1410. That is, the elastic member 1321 may provide an elastic force in a direction of pushing the friction member 1322 away from the connector base 1310.

Meanwhile, the pusher member 1420 may be disposed to pass through the cover 1410 and may be able to press the reaction force member 1320. Specifically, the pusher member 1420 may include a pressing part 1421 protruding to the outside of the cover 1410, and a pressing protrusion 1422 contactable with the friction member 1322 may be formed inside the cover 1410. In other words, it may be said that the pusher member 1420 forms the pressing part 1421 on an end portion thereof, which is opposite to one end portion in contact with the reaction force member 1320.

As shown in FIG. 16 or the like, the pressing part 1421 may be formed in the shape of a circular plate with a through hole formed therein for the shaft 1100 to pass therethrough. In addition, the pressing protrusion 1422 may be coupled to and protrude from the pressing part 1421 toward the friction member 1322. That is, the pressing protrusion 1422 may be disposed in a direction parallel to the shaft 1100. Here, a plurality of pressing protrusions 1422 may be formed at positions respectively corresponding to the reaction force members 1320. In addition, it may be said that the plurality of pressing protrusions 1422 are connected to the pressing part 1421. However, the concept of the present disclosure is not limited thereto, and the pusher member 1420 may be disposed in various positions and orientations capable of pressing the friction member 1322 toward the connector base 1310.

Hereinafter, an operation mechanism of the shaft attachment and detachment apparatus 1010 according to the second embodiment of the present disclosure will be described.

When the shaft 1100 is inserted into the connector 1300, the shaft 1100 may come into contact with the reaction force member 1320, but the shaft 1100 may be inserted until being in contact with the boundary surface 1311a of the connector base 1310 without significant external force.

However, when the shaft 1100 is withdrawn from the connector 1300, the shaft 1100 may encounter resistance to being withdrawn due to friction with the reaction force member 1320. That is, it may be said that the shaft 1100 may be coupled to the connector 1300.

Specifically, the shaft 1100 inserted into the connector 1300 may be in a state of being in contact with the friction member 1322. In addition, the friction member 1322 may also be in a state of being in contact with the inner inclined surface 1411 of the cover 1410. When the shaft 1100 inserted into the connector base 1310 is to be withdrawn from connector base 1310, the friction member 1322 in contact with the shaft 1100 may attempt to move together with the shaft 1100 in the direction of withdrawal. At this time, since the friction member 1322 is in contact with the inner inclined surface 1411 of the cover 1410, the friction member 1322 may move along the inner inclined surface 1411. That is, the friction member 1322 may be guided by the inner inclined surface 1411 to move in a direction toward the shaft 1100. In other words, as the shaft 1100 is withdrawn, the friction member 1322 presses a side surface of the shaft 1100.

As a result, when the shaft 1100 inserted into the connector base 1310 is to be withdrawn from the connector base 1310, the reaction force member 1320 presses the side surface of the shaft 1100 to fix the shaft 1100 by friction generated between the reaction force member 1320 and the shaft 1100.

Here, since an outer shape of the shaft 1100 may be deformed or damaged due to the frictional force generated between the cover 1410 and the friction member 1322, and the shaft 1100, in order to prevent this, as many reaction force members 1320 as space allows may be disposed to distribute the force.

Meanwhile, the shaft 1100 may be withdrawn from the connector 1300 by releasing the coupling of the shaft 1100 and the connector 1300. In order to release the coupling between the shaft 1100 and the connector, the pressing part 1421 may be pressed. Specifically, by pressing the pressing part 1421, the pressing protrusions 1422 of the pusher member 1420 press the reaction force members 1320, and the reaction force members 1320 may be compressed or moved backward toward the connector base 1310.

As described above, when the reaction force member 1320 is compressed or moved backward toward the connector base 1310, the reaction force member 1320 may not be in contact with the inner side surface of the cover 1410. Thus, the friction member 1322 does not move toward the shaft 1100 along the inclined surface of the cover 1410, resulting in the friction member 1322 not applying a pressure to the side surface of the shaft 1100. As a result, a user can release a coupling structure for fixing the shaft 1100 by pressing the pressing part 1421.

Modified Example of Second Embodiment

Hereinafter, a shaft of a shaft attachment and detachment apparatus according to a modified example of the second embodiment of the present disclosure will be described. Here, the shaft attachment and detachment apparatus according to the modified example of the second embodiment of the present disclosure is different from the shaft attachment and detachment apparatus 1010 according to the second embodiment of the present disclosure described above in that the shape of the shaft is different.

Figure 19:
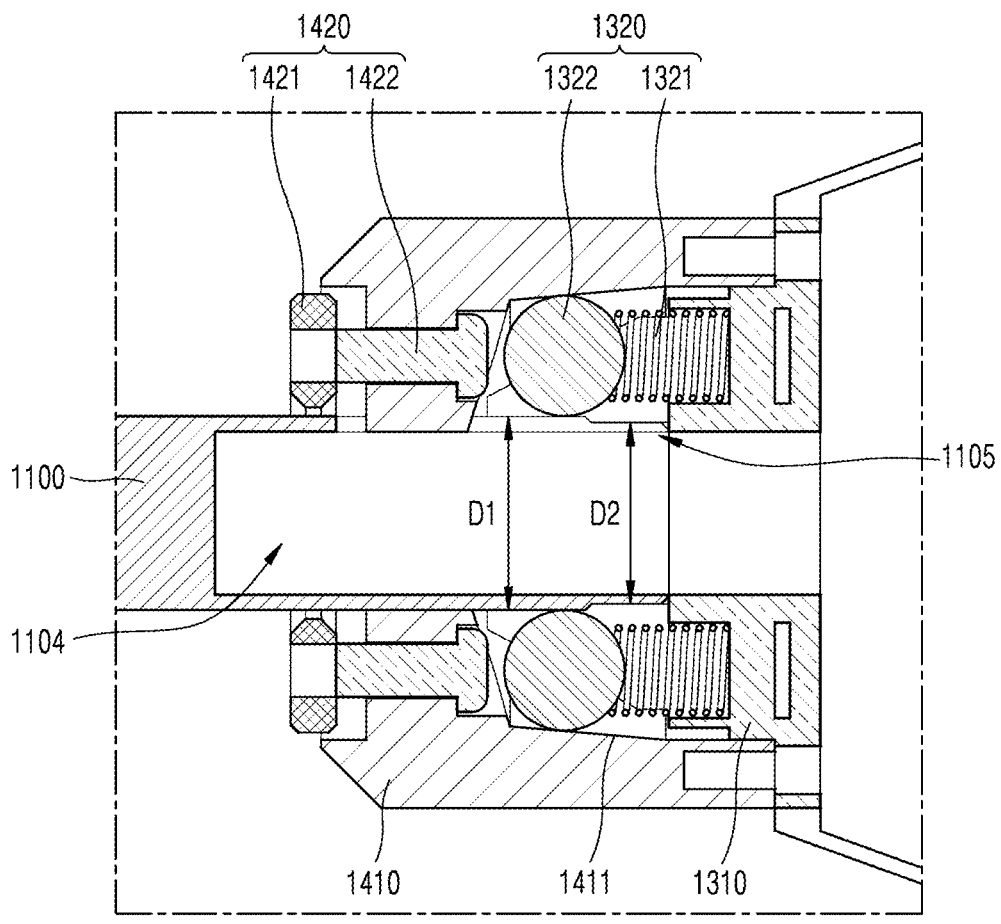
FIGS. 19 and 20 are side cross-sectional views illustrating a shaft attachment and detachment apparatus according to a modified example of the second embodiment of the present disclosure.
Figure 19:
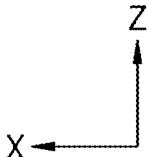
Figure 20:
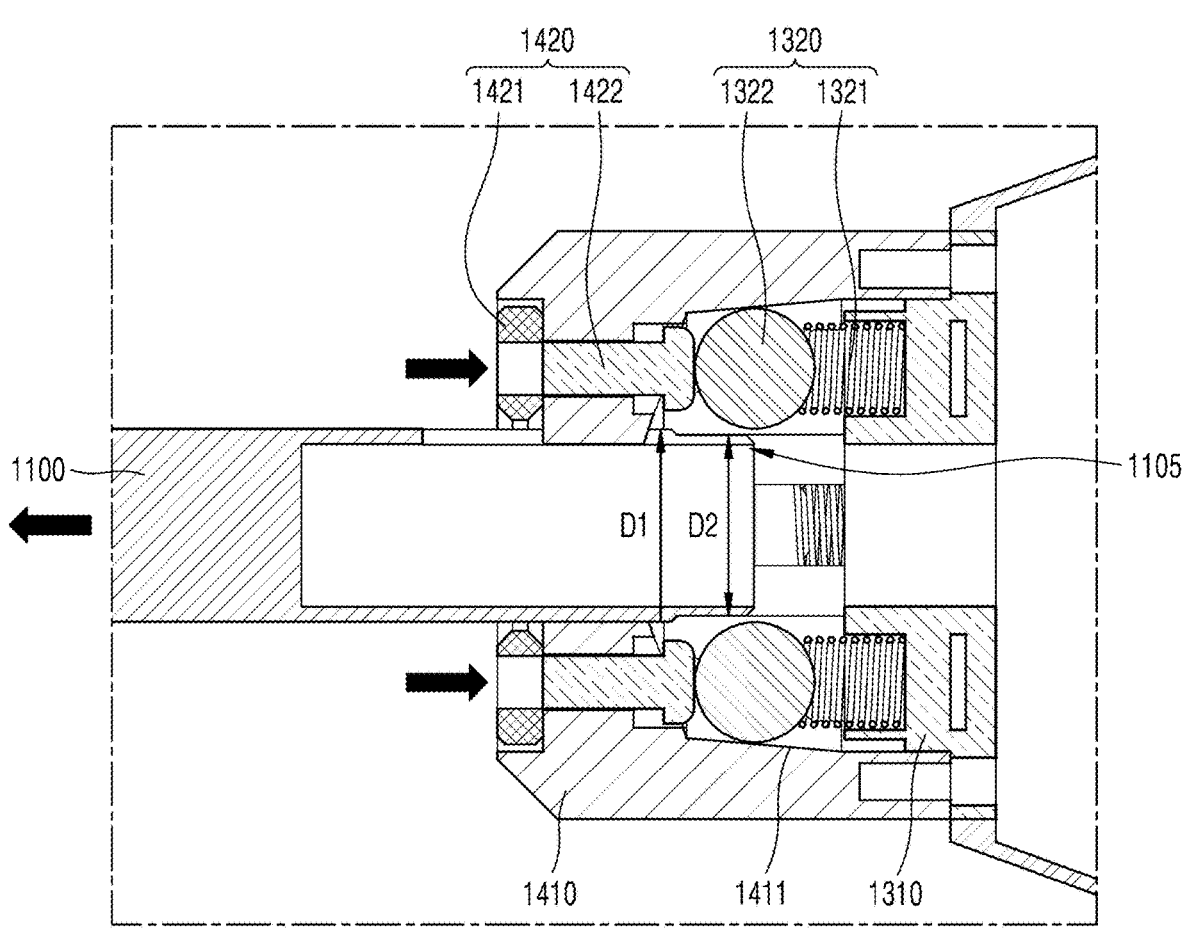
Figure 20:
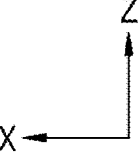

FIGS. 19 and 20 are side cross-sectional views illustrating the shaft attachment and detachment apparatus according to the modified example of the second embodiment of the present disclosure.

The shaft 1100 of the shaft attachment and detachment apparatus according to the modified example of the second embodiment of the present disclosure may include a main region 1104 and an end portion region 1105 adjacent to the connector base 1310 than the main region 1104, and the end portion region 1105 may include a region whose width is less than that of the main region 1104. Specifically, a portion of the end portion region 1105 in contact with the reaction force member 1320 may have a width less than that of the main region 1104. Alternatively, it may be said that an outer diameter D2 of the end portion region 1105 is less than an outer diameter D1 of the main region 1104.

The end portion region 1105 may be formed to extend from the main region 1104. The main region 1104 may be formed to a position in which the shaft 1100 is contactable with at least the reaction force member 1320 when the shaft 1100 is completely inserted into the connector 1300. In other words, in a state in which the shaft 1100 is inserted into and coupled to the connector base 1310, the reaction force member 1320 may be partially in contact with the main region 1104. However, the end portion region 1105 may not be in contact with the reaction force member 1320.

Accordingly, in a state in which the shaft 1100 is partially withdrawn from the connector base 1310, the reaction force member 1320 and the end portion region 1105 of the shaft 1100 may be spaced apart from each other. At this time, the friction member 1322 may attempt to move toward the shaft 1100 along the inner inclined surface 1411 of the cover 1410 by the elastic member 1321, but the guide part 1312 of the connector base 1310 may restrict the movement of the friction member 1322. Thus, the friction member 1322 may not be in contact with the end portion region 1105, or even when the friction member 1322 is in contact with the end portion region 1105, the friction member 1322 may not press the end portion region 1105.

Accordingly, in the shaft attachment and detachment apparatus according to the modified example of the second embodiment of the present disclosure, it may not be necessary to continue applying a pressure to the pressing part 1421 until the shaft 1100 is completely withdrawn from the connector 1300. Accordingly, when the shaft 1100 is detached from the device body (not shown), the shaft 1100 may be easily uncoupled.

In addition, when the shaft 1100 is inserted into the connector 1300, the end portion region 1105 having a small outer diameter comes into contact with the friction member 1322 first, and thus the shaft 1100 may be smoothly inserted by pushing the friction member 1322 outward instead of colliding with the friction member 1322.

Figure 21:
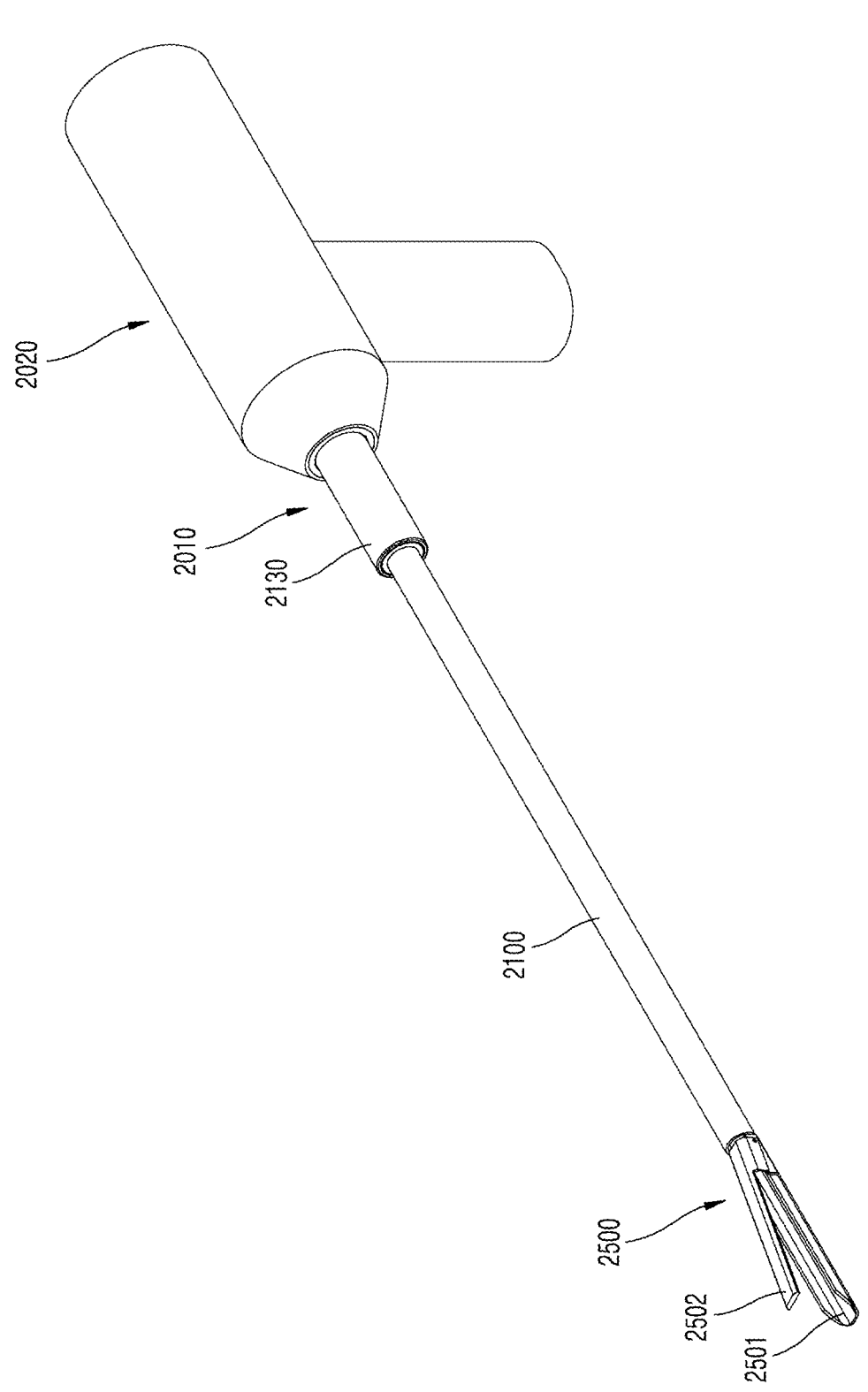
FIG. 21 is a perspective view schematically illustrating a surgical instrument to which the shaft attachment and detachment apparatus according to an embodiment of the present disclosure is applied.

FIG. 21 is a perspective view schematically illustrating a surgical instrument to which the shaft attachment and detachment apparatus according to an embodiment of the present disclosure is applied.

Referring to FIG. 21, the surgical instrument according to an embodiment of the present disclosure may include an end tool 2500, a manipulation part 2020, a shaft 2100, and a shaft attachment and detachment apparatus 2010.

Since the shaft attachment and detachment apparatus 2010 is substantially the same as the shaft attachment and detachment apparatus according to the first embodiment of the present disclosure, a detailed description thereof will be omitted.

In addition, although not shown in the drawings, in an optional embodiment, it is of course possible that one of the shaft attachment and detachment apparatuses described above may be selectively applied to the surgical instrument.

The end tool 2500 may be coupled to one end portion of the shaft 2100 of the shaft attachment and detachment apparatus 2010. Here, the end tool 2500 performs necessary motions for surgery by being inserted into a surgical site. In an example of the end tool 2500 described above, as illustrated in FIG. 21, a pair of jaws for performing a grip motion may be used. However, the concept of the present disclosure is not limited thereto, and various devices for performing surgery may be used as the end tool 2500. The end tool 2500 is connected to the manipulation part 2020, and receives a driving force of the manipulation part 2020 through the shaft 2100 to perform a motion necessary for surgery, such as gripping, cutting, suturing, or the like.

Here, the end tool 2500 may include a pair of jaws, that is, a first jaw 2501 and a second jaw 2502, and the end tool 2500 may be formed to be rotatable in one or more directions. In addition, the end tool 2500 may also include a staple and a blade. Specifically, any one of the jaws may include the staple and the blade. In addition, the manipulation part 2020 may control stapling and cutting motions of the end tool 2500.

Here, the end tool 2500 may simultaneously perform the stapling and cutting motions. That is, it may be said that, when the body tissue is interposed between the first jaw 2501 and the second jaw 2502, the suturing and cutting of the body tissue are simultaneously performed.

Here, the end tool 2500 is described as including a pair of jaws for performing a grip motion, that is, the first jaw 2501 and the second jaw 2502, but, the concept of the present disclosure is not limited thereto, and an end tool capable of performing various operations may be applied.

The shaft 2100 may serve to connect the manipulation part 2020 to the end tool 2500. That is, one end portion of the shaft 2100 may be connected to the end tool 2500, and the other end portion thereof may be connected to the manipulation part 2020.

The manipulation part 2020 is coupled to another end portion of the shaft 2100 and provided as an interface to be directly controlled by a medical doctor, and may have, for example, a handle, a tongs shape, a stick shape, a lever shape, or the like, and when the medical doctor controls the manipulation part 2020, the end tool, which is connected to the corresponding interface and inserted into the body of a surgical patient, performs a certain motion, thereby performing surgery. Here, the manipulation part 2020 is illustrated as being formed of a handle and a body that are gripped with one hand, but the concept of the present disclosure is not limited thereto, and various types of manipulation parts that can be connected to the end tool 2500 and manipulate the end tool 2500 may be possible.

Surgical Instrument

Hereinafter, a surgical instrument to which the shaft attachment and detachment apparatus according to an embodiment of the present disclosure is applicable and an end tool of the surgical instrument will be described in detail.

Figure 22:
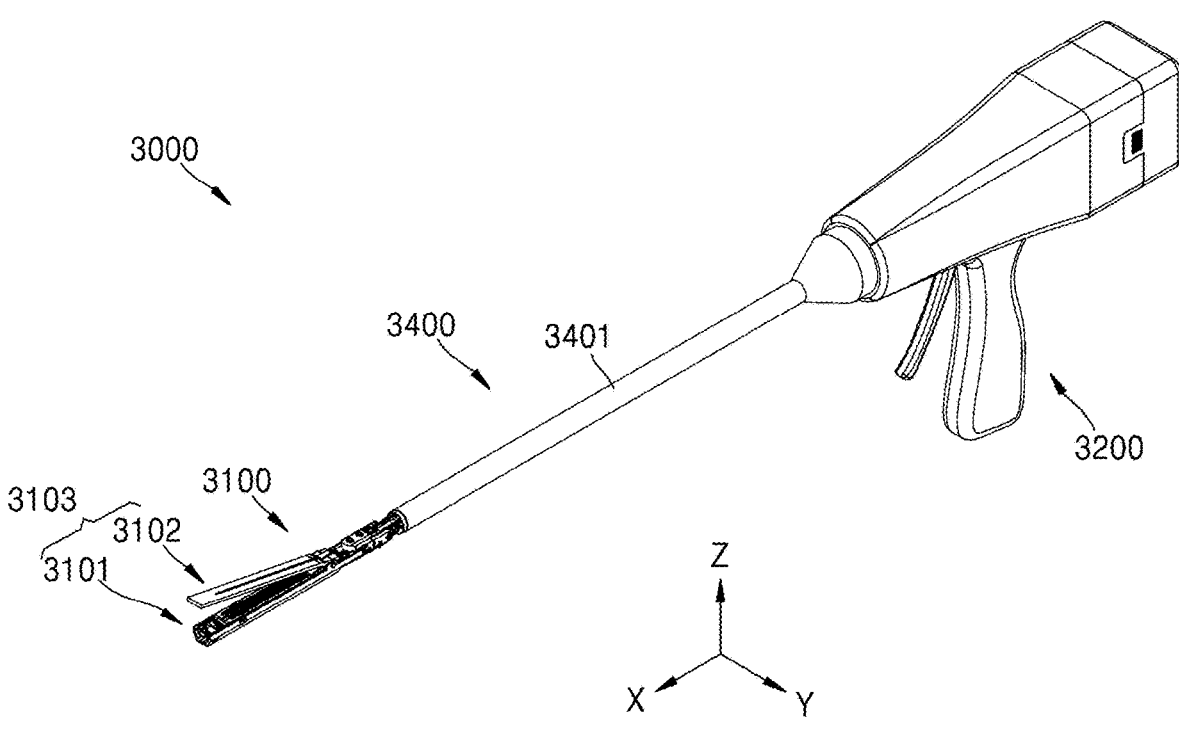
FIG. 22 is a schematic perspective view of a surgical instrument to which the shaft attachment and detachment apparatus according to an embodiment of the present disclosure is applicable.
Figure 23:
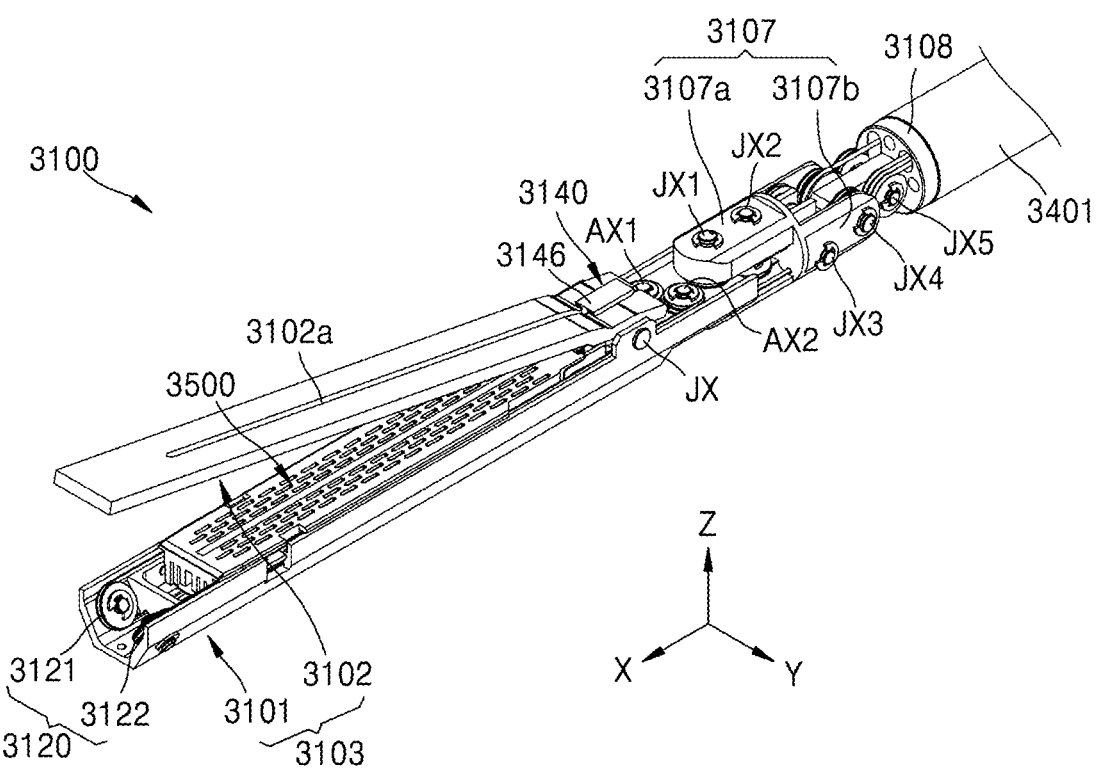
FIG. 23 is a schematic perspective view for describing an end tool of FIG. 22.
Figure 24:
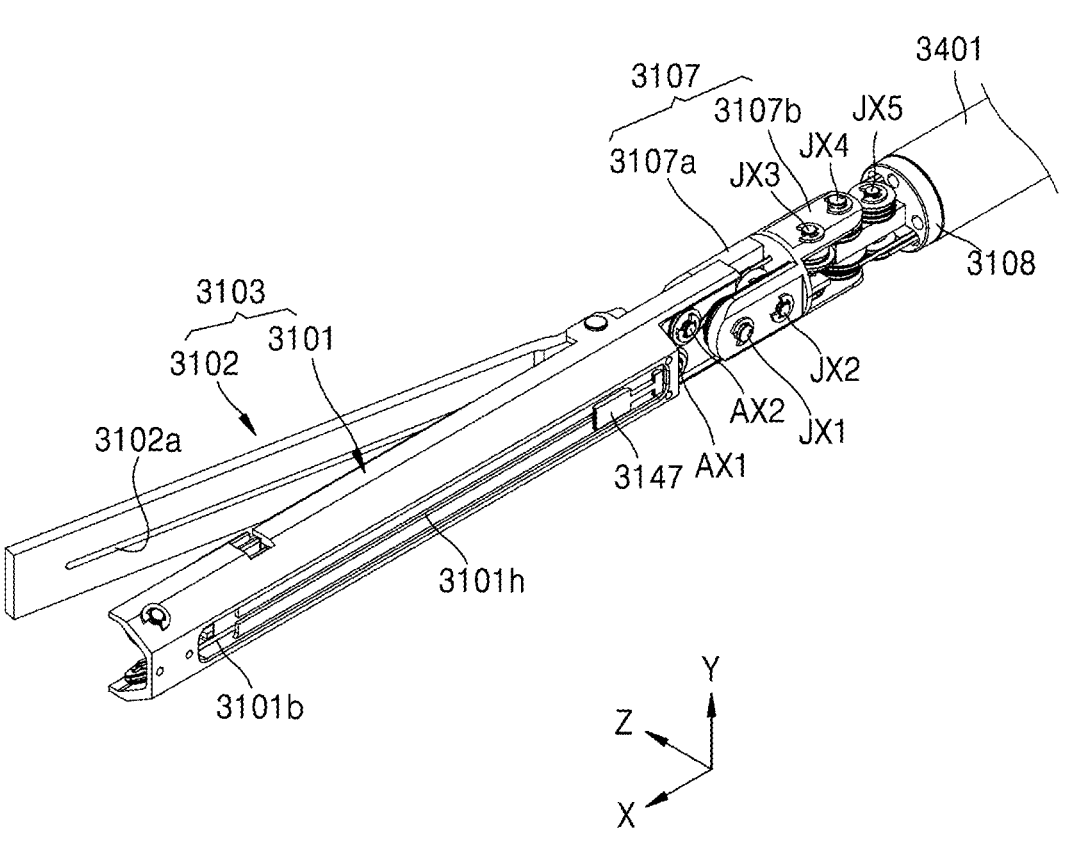
FIG. 24 is a perspective view of the end tool of FIG. 23 viewed from another direction.
Figure 25:
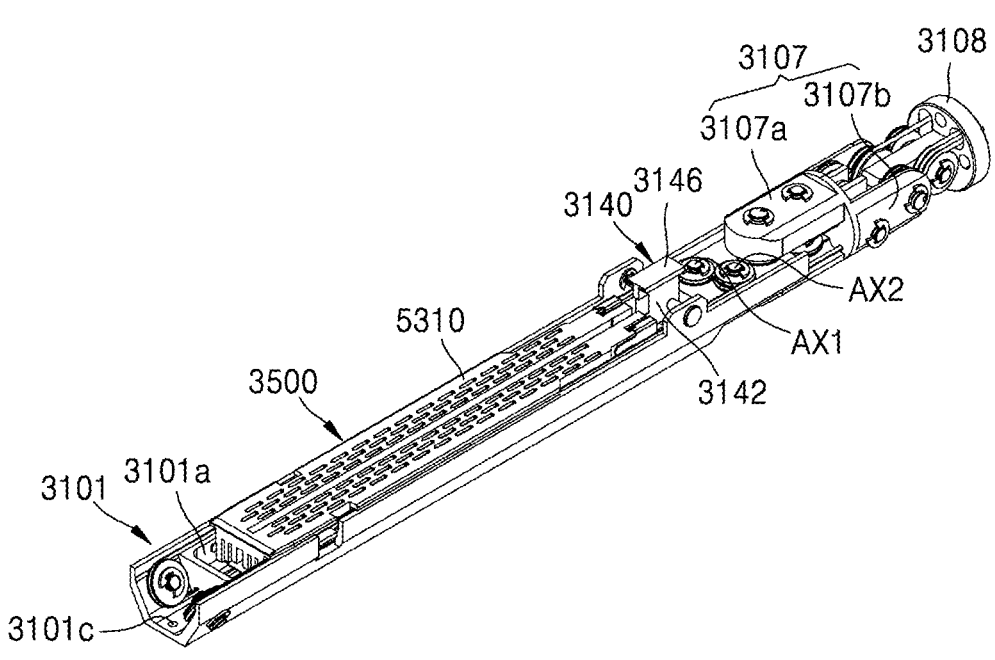
FIG. 25 is a schematic perspective view of the end tool of FIG. 23 with a second jaw removed.
Figure 26:
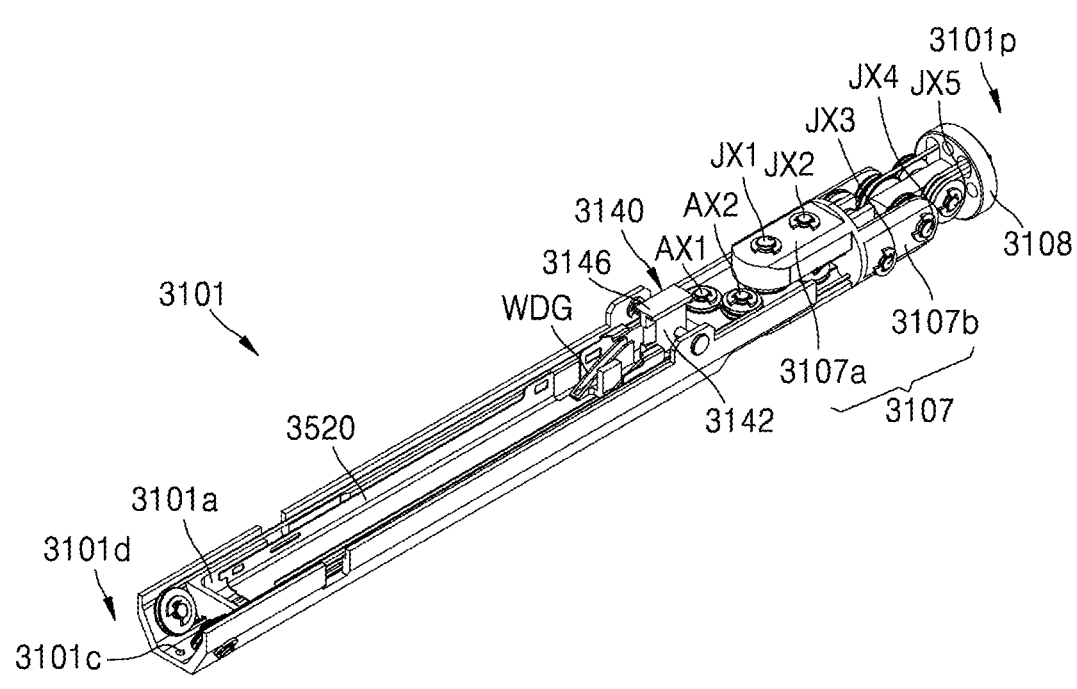
FIG. 26 is a schematic perspective view of the end tool of FIG. 25 with a cartridge removed.
Figure 27:
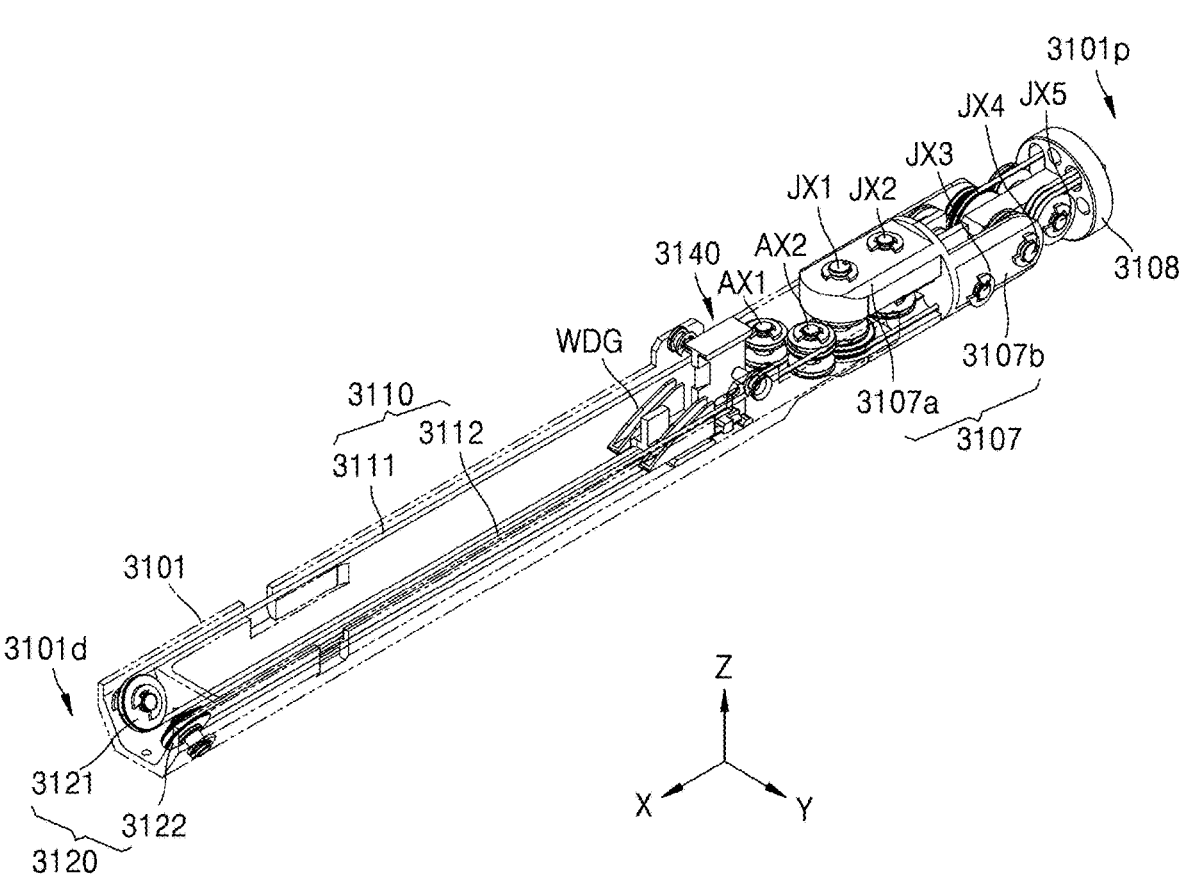
FIG. 27 is a transparent perspective view of FIG. 26.
Figure 28:
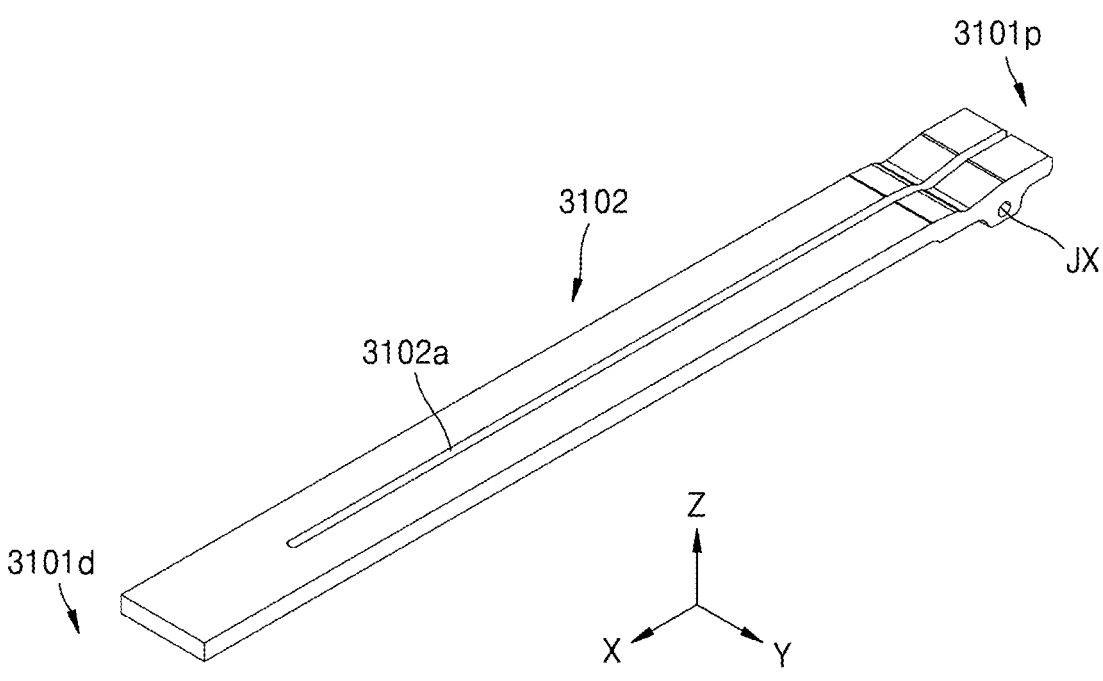
FIG. 28 is a perspective view schematically illustrating the second jaw of the end tool of FIG. 23.
Figure 29:
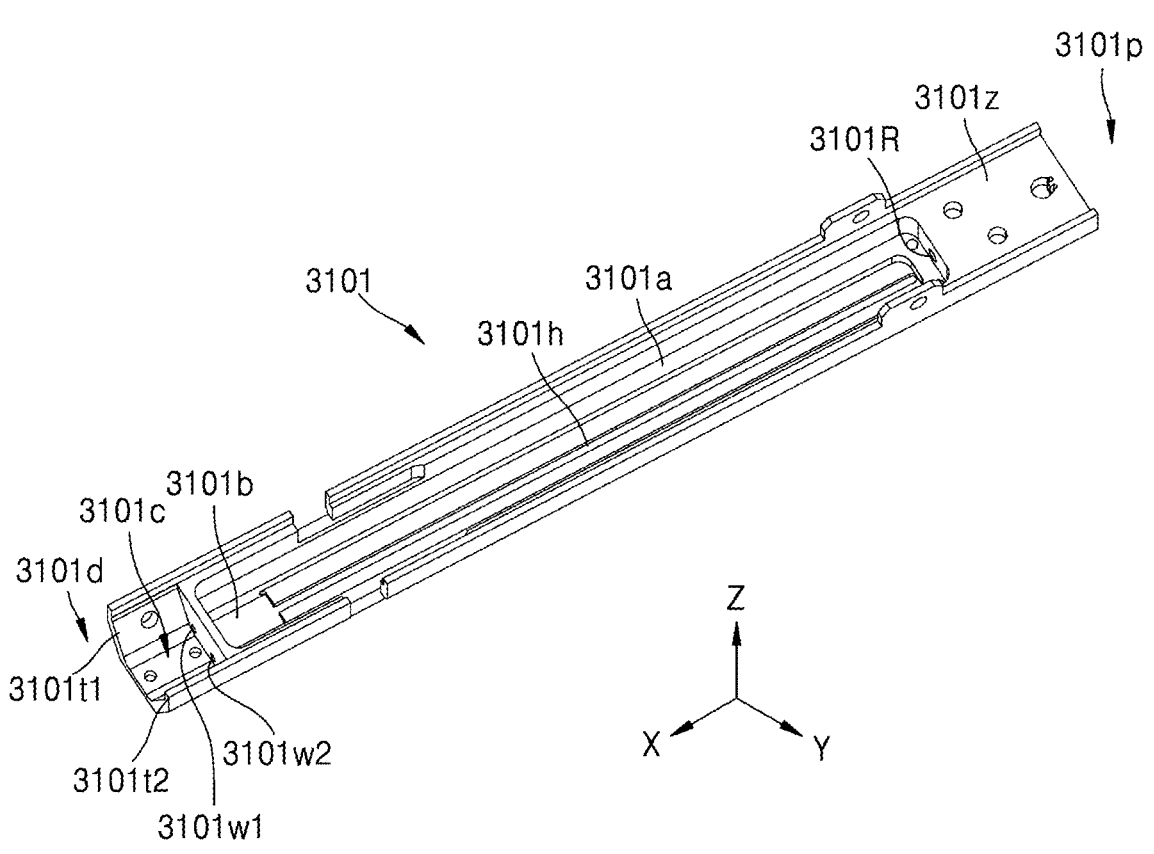
FIG. 29 is a perspective view schematically illustrating a first jaw of the end tool of FIG. 23.
Figure 30:
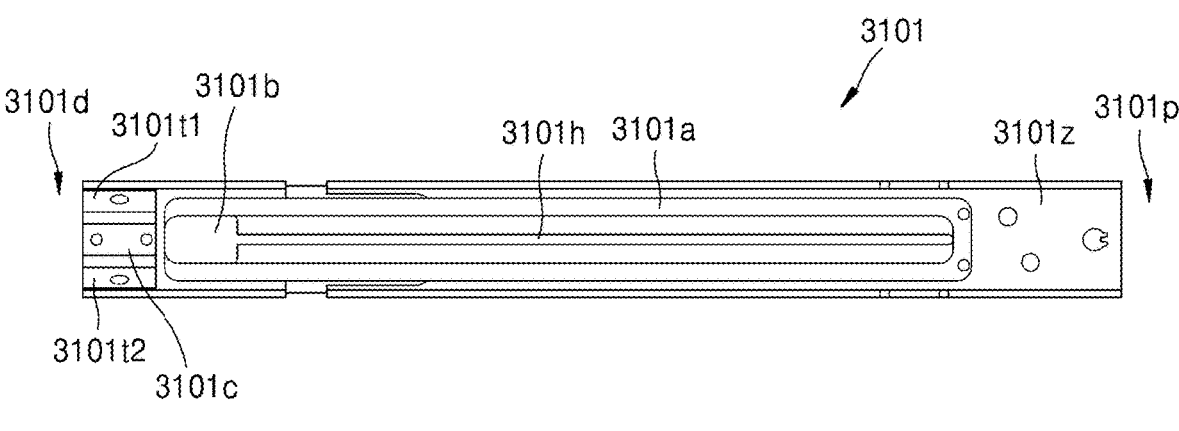
FIG. 30 is a plan view schematically illustrating the first jaw of the end tool of FIG. 23.
Figure 30:
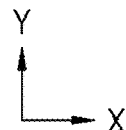
Figure 31:
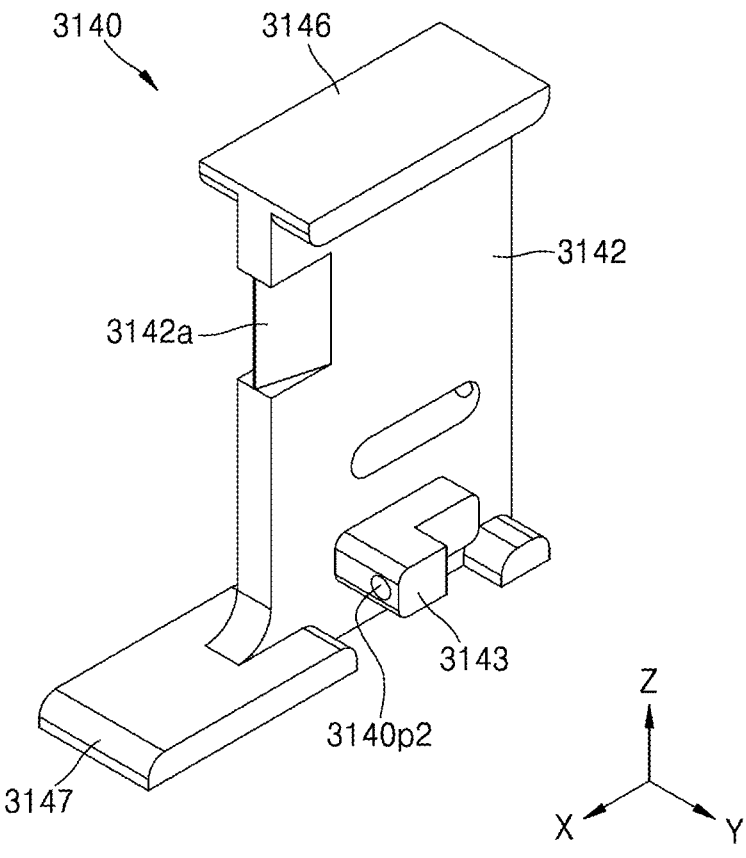
FIG. 31 is a perspective view illustrating an operation member of the end tool of FIG. 23.
Figure 32:
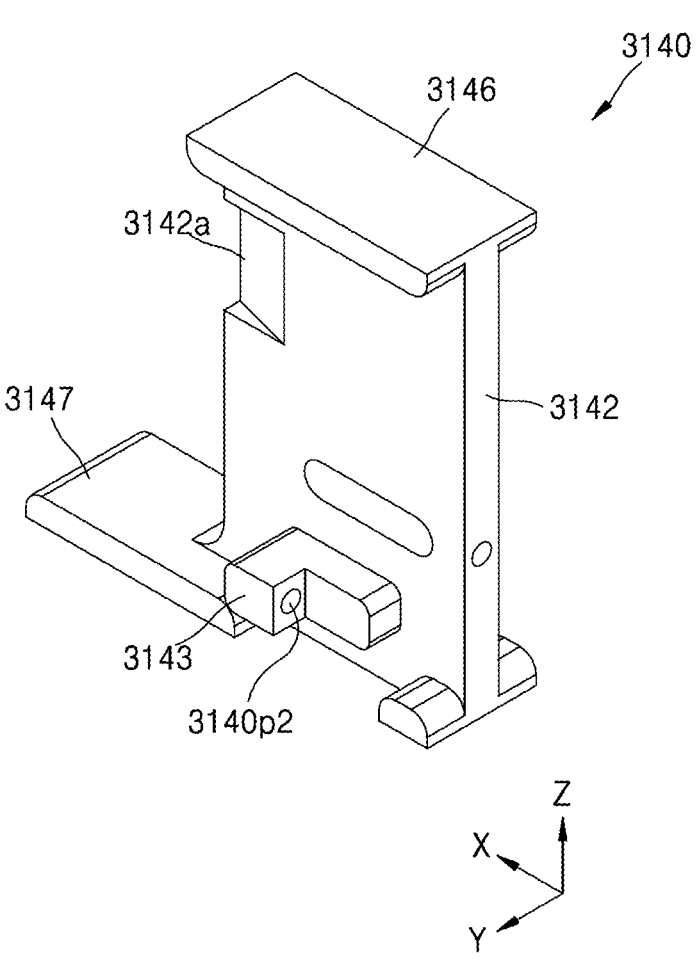
FIG. 32 is a perspective view of the operation member of FIG. 31 viewed from another direction.
Figure 33:
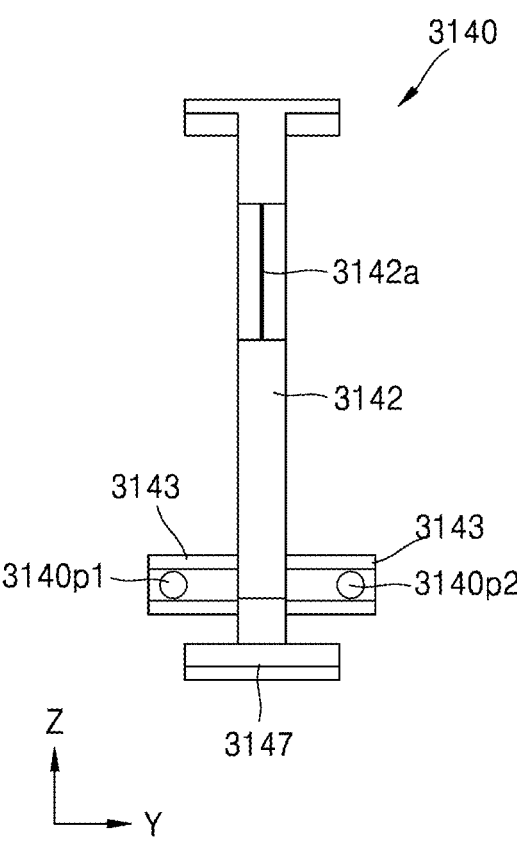
FIG. 33 is a front view of the operation member of FIG. 31 viewed in one direction.
Figure 34:
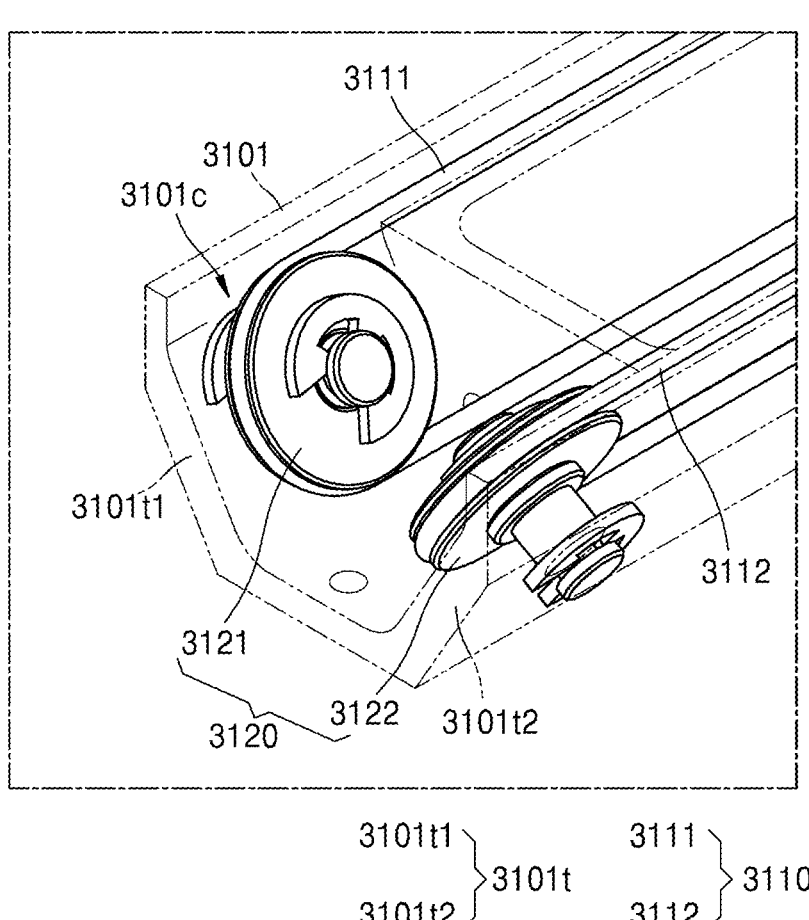
FIG. 34 is a schematic perspective view illustrating a portion of the end tool of FIG. 23.
Figure 35:
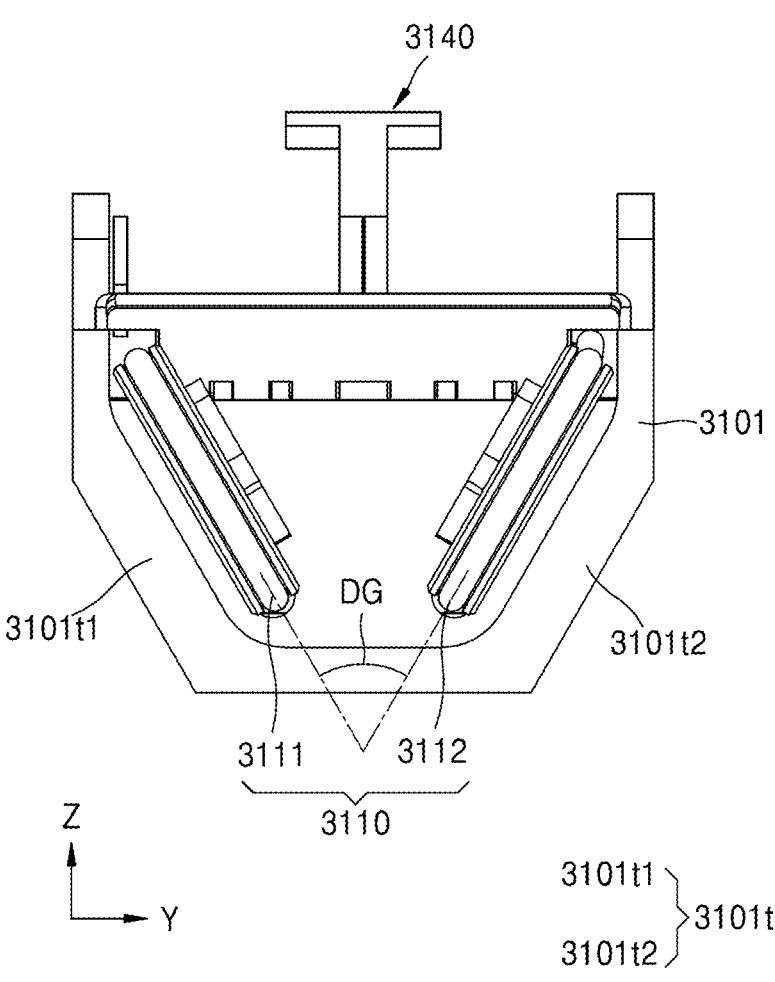
FIG. 35 is a front view of FIG. 34 viewed in one direction.
Figure 36:
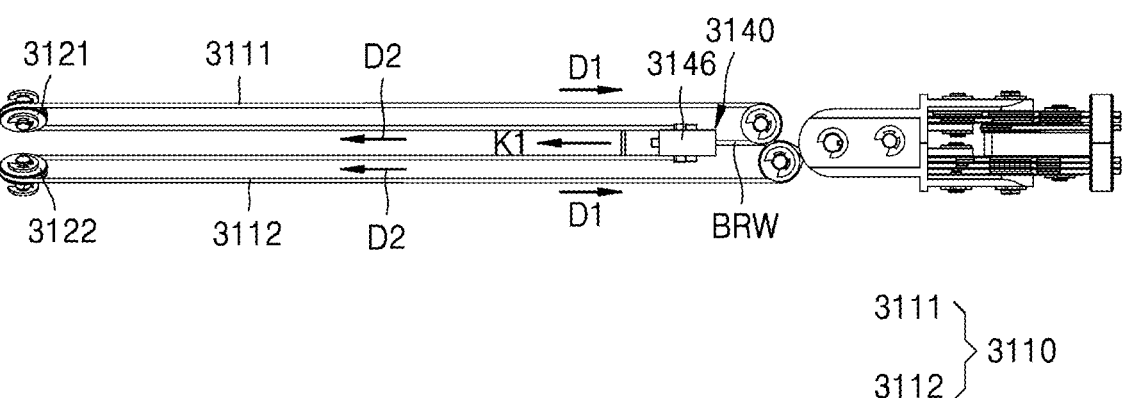
FIG. 36 is a schematic plan view for describing the operation member, a fixed pulley, and a forward-moving wire of the end tool of FIG. 23.
Figure 37:
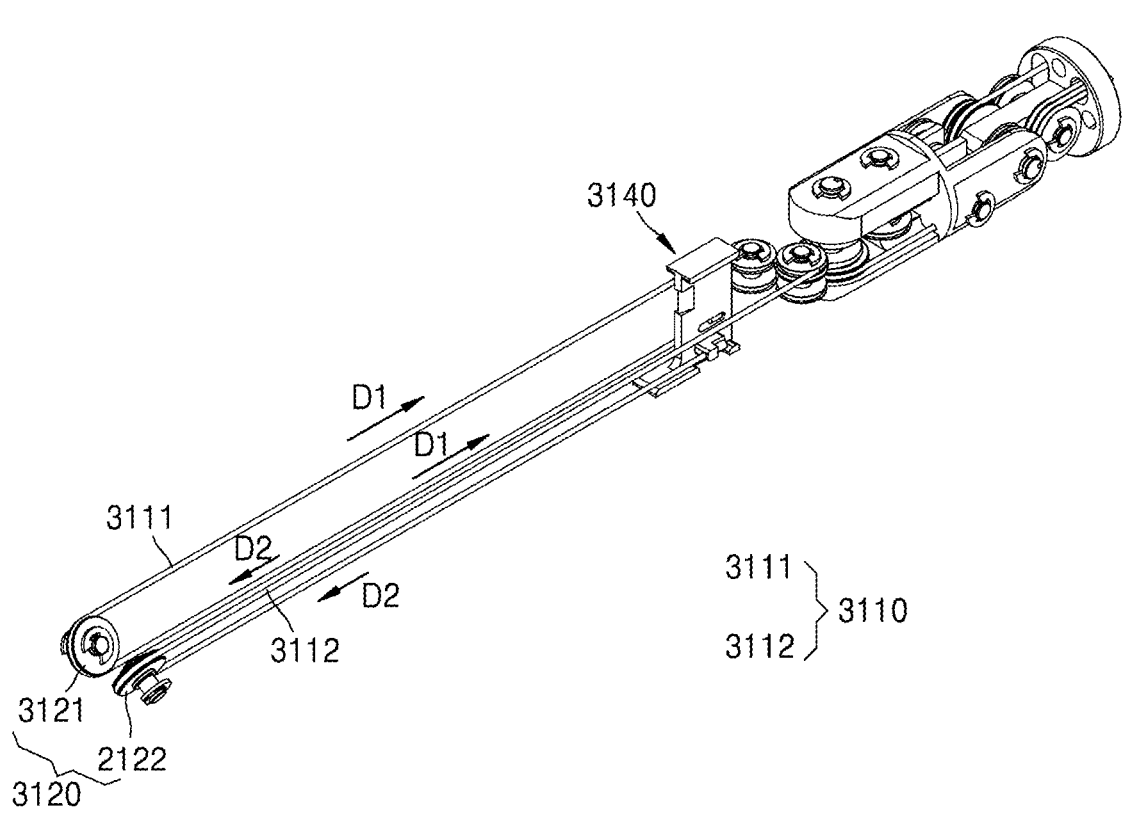
FIG. 37 is a schematic perspective view for describing the operation member, the fixed pulley, and the forward-moving wire of the end tool of FIG. 23.
Figure 42:
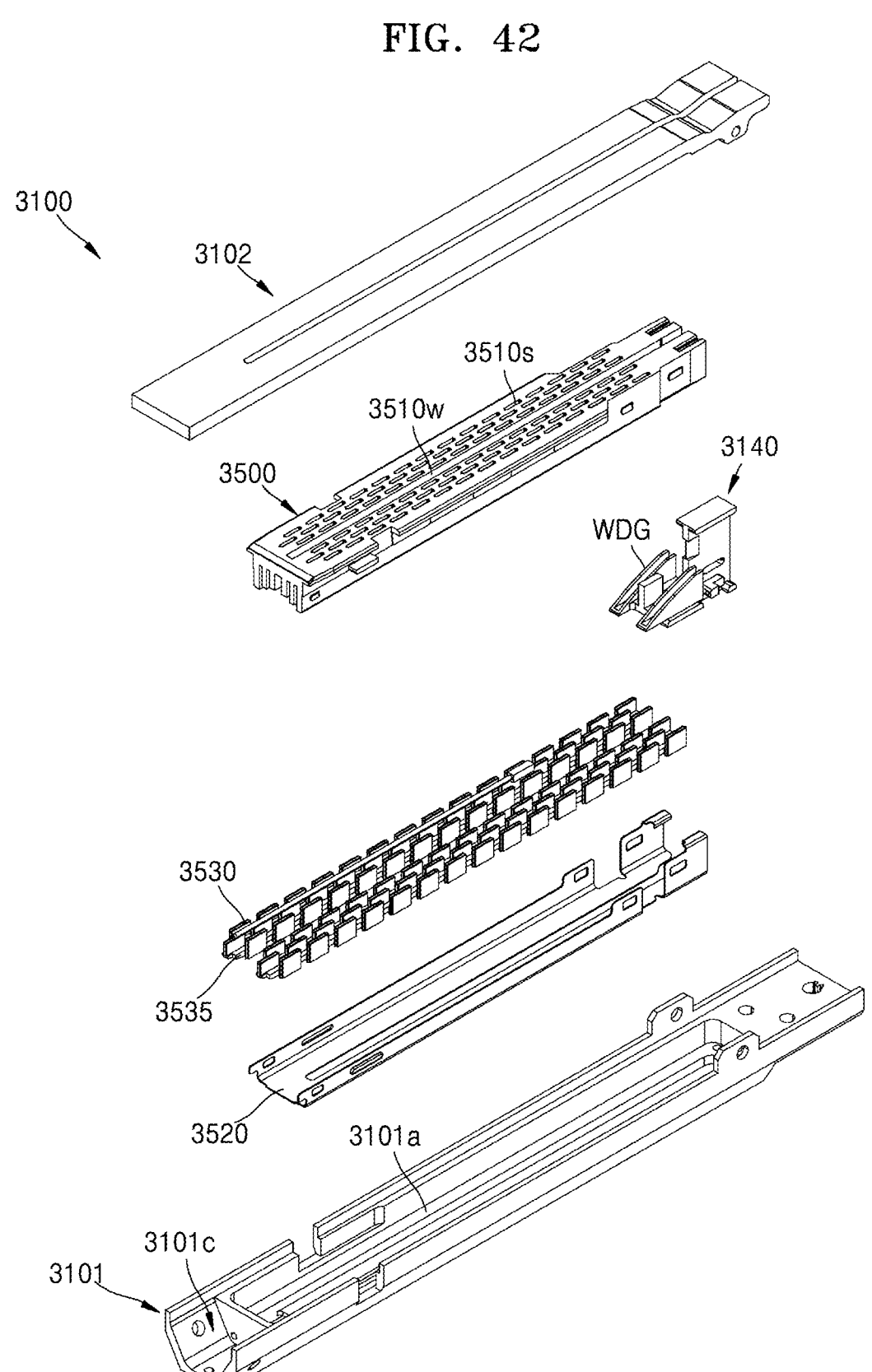
FIG. 42 is a perspective view illustrating the first jaw and the cartridge of the surgical instrument of FIG. 22.
Figure 43:
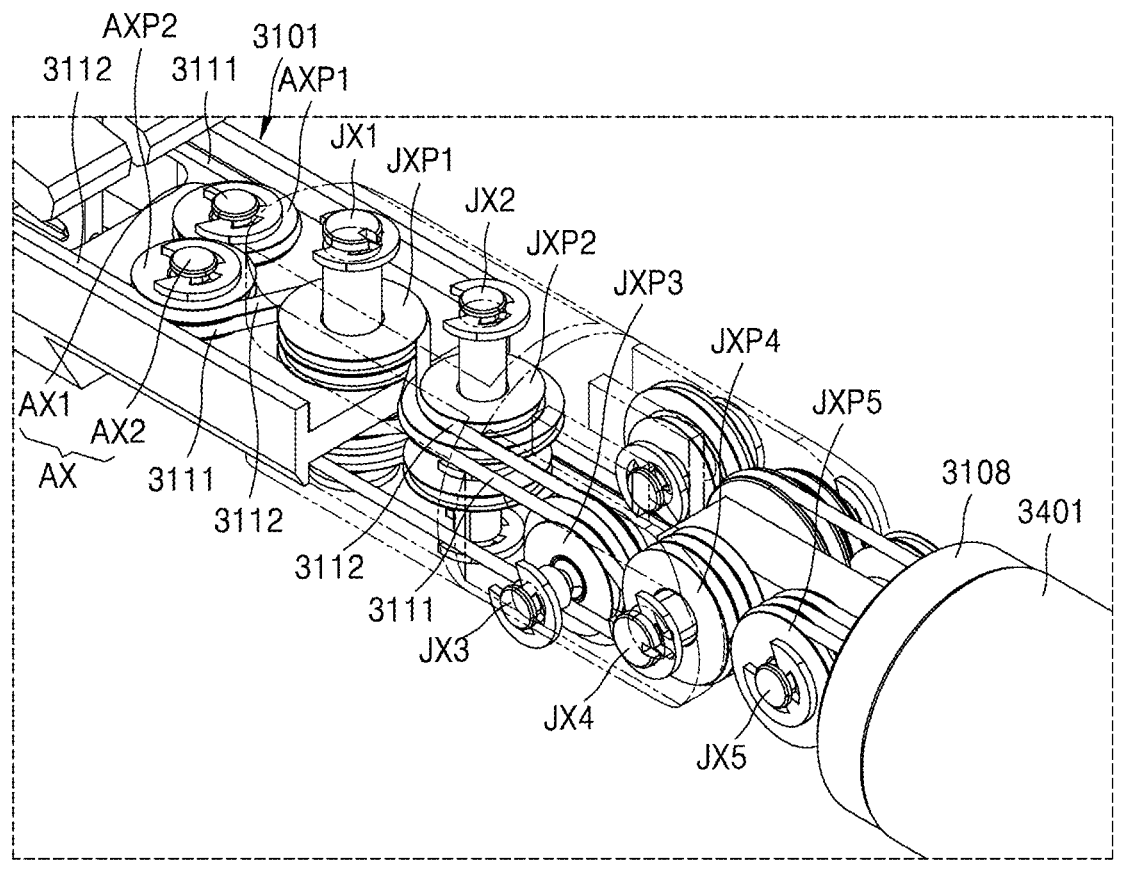
FIGS. 43 and 44 are views for describing a switching pulley, a yaw pulley, and a pitch pulley of the end tool of the surgical instrument of FIG. 22.
Figure 44:
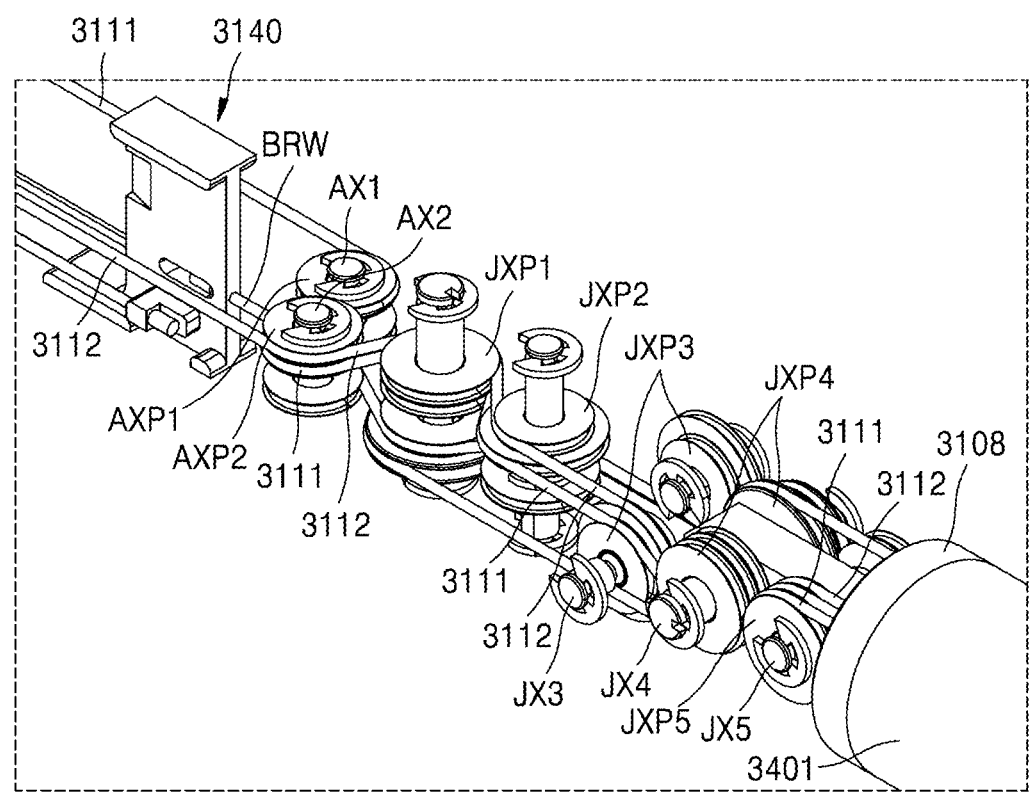

FIG. 22 is a schematic perspective view of a surgical instrument according to another embodiment of the present disclosure. FIG. 23 is a schematic perspective view for describing an end tool of FIG. 22. FIG. 24 is a perspective view of the end tool of FIG. 23 viewed from another direction. FIG. 25 is a schematic perspective view of the end tool of FIG. 23 with a second jaw removed. FIG. 26 is a schematic perspective view of the end tool of FIG. 25 with a cartridge removed. FIG. 27 is a transparent perspective view of FIG. 26. FIG. 28 is a perspective view schematically illustrating the second jaw of the end tool of FIG. 23. FIG. 29 is a perspective view schematically illustrating a first jaw of the end tool of FIG. 23. FIG. 30 is a plan view schematically illustrating the first jaw of the end tool of FIG. 23. FIG. 31 is a perspective view illustrating an operation member of the end tool of FIG. 23. FIG. 32 is a perspective view of the operation member of FIG. 31 viewed from another direction. FIG. 33 is a front view of the operation member of FIG. 31 viewed in one direction. FIG. 34 is a schematic perspective view illustrating a portion of the end tool of FIG. 23. FIG. 35 is a front view of FIG. 34 viewed in one direction. FIG. 36 is a schematic plan view for describing the operation member, a fixed pulley, and a forward-moving wire of the end tool of FIG. 23. FIG. 37 is a schematic perspective view for describing the operation member, the fixed pulley, and the forward-moving wire of the end tool of FIG. 23. FIGS. 38 and 39A, 39B, and 39C are schematic views for describing an operation of the operation member of the end tool of FIG. 23. FIGS. 40 and 41A, 41B, and 41C are views for describing an optional embodiment in which a backward-moving wire is added to the end tool of FIG. 23. FIG. 42 is a perspective view illustrating the first jaw and a cartridge of the surgical instrument of FIG. 22. FIGS. 43 and 44 are views for describing a switching pulley, a yaw pulley, and a pitch pulley of the end tool of the surgical instrument of FIG. 22.

A surgical instrument 3000 according to the present embodiment may include an end tool 3100, an operator 3200, and a connector 3400.

Here, the connector 3400 is formed in the shape of a hollow shaft, and one or more wires and electric wires may be accommodated therein. The operator 3200 is coupled to one end portion of the connector 3400, the end tool 3100 is coupled to another end portion thereof, and the connector 3400 may serve to connect the operator 3200 to the end tool 3100. As an example, the connector 3400 may include a straight part 3401, and although not shown in the drawings, the connector 3400 may include one or more curved parts to increase ease of use and control the arrangement of components for manipulation.

The operator 3200 is formed at the one end portion of the connector 3400 and provided as an interface to be directly controlled by a medical doctor, for example, a tongs shape, a stick shape, a lever shape, or the like, and when the medical doctor controls the operator 3200, the end tool 3100, which is connected to the interface and inserted into the body of a surgical patient, performs a certain motion, thereby performing surgery. Here, the operator 3200 is illustrated in FIG. 22 as being formed in a handle shape allowing user's fingers to come into close contact therewith and perform one or more motions, such as pulling or pushing, but the concept of the present disclosure is not limited thereto, and various types of manipulation parts that can be connected to the end tool 3100 and manipulate the end tool 3100 may be possible.

The end tool 3100 is formed on another end portion of connector 3400, and performs necessary motions for surgery by being inserted into a surgical site. As an example of the end tool 3100, a pair of jaws 3103 for performing a grip motion may be used. However, the concept of the present disclosure is not limited thereto, and various devices for performing surgery may be used as the end tool 3100. For example, a configuration of a cantilever cautery may also be used as the end tool. The end tool 3100 is connected to the operator 3200 by an operating force transmitter (not shown, e.g., a wire or the like), and receives a driving force of the operator 3200 through the operating force transmitter to perform a motion necessary for surgery, such as gripping, cutting, suturing, or the like.

Hereinafter, the end tool 3100 of the surgical instrument 3000 of FIG. 22 will be described in more detail.

FIG. 23 is a schematic perspective view for describing the end tool of FIG. 22. FIG. 24 is a perspective view of the end tool of FIG. 23 viewed from another direction. FIG. 25 is a schematic perspective view of the end tool of FIG. 23 with the second jaw removed. FIG. 26 is a schematic perspective view of the end tool of FIG. 25 with the cartridge removed. FIG. 27 is a transparent perspective view of FIG. 26.

The end tool 3100 may include the jaw 3103, a plurality of fixed pulleys 3120, and a plurality of forward-moving wires 3110. The plurality of fixed pulleys 3120 may include two or more pulleys, for example, a first fixed pulley 3121 and a second fixed pulley 3122. The plurality of forward-moving wires 3110 include two or more wires, and may include, for example, a first forward-moving wire 3111 and a second forward-moving wire 3112.

The jaw 3103 may perform various functions, for example, a grip motion, and may include a pair of jaws, e.g., a first jaw 3101 and a second jaw 3102 as a specific example.

Here, each of the first jaw 3101 and the second jaw 3102, or a component encompassing the first jaw 3101 and the second jaw 3102 may be referred to as the jaw 3103.

The first jaw 3101 and the second jaw 3102 may be disposed to face each other, may move closer to or move away from each other, and may be formed to rotationally move around, for example, one shaft JX.

A cartridge 3500 may be disposed to be accommodated in the first jaw 3101, and a plurality of staples are disposed inside the cartridge 3500. When an operation member 3140 receives a force through the forward-moving wire 3110 while the first jaw 3101 and the second jaw 3102 are close to each other, such as when the first jaw 3101 and the second jaw 3102 are closed with the body tissue interposed therebetween, the operation member 3140 may push and raise the staples while moving toward a distal end 3101*d* of the first jaw 3101, so that stapling may be performed. At this point, one or more clamps 3146 and 3147 of the operation member 3140 may protrude to the outside of the first jaw 3101 and the second jaw 3102, allowing the operation member 3140 to move forward while applying pressure to an outer surface of the first jaw 3101 and the second jaw 3102, which facilitates the smooth progression of a stapling process. In an optional embodiment, the cartridge 3500 may include a case 3520 corresponding to the bottom, and the case 3520 is disposed in the first jaw 3101.

Meanwhile, the operation member 3140 may be used together with a wedge WDG. For example, the wedge WDG may be prepared separately from the operation member 3140 and then disposed adjacent to the operation member 3140 in the first jaw 3101. In addition, as another example, the operation member 3140 and the wedge WDG may be integrally formed. The wedge WDG may be disposed on at least one side of a body 3142 and may be formed to have a predetermined inclined surface. That is, the wedge WDG may be formed to be inclined by a certain degree with respect to the extension direction of the end tool 3100. In other words, the wedge WDG may be formed to have a greater height at a proximal end 3101*p* side of the first jaw 3101 than a distal end 3101*d* side of the first jaw 3101.

The wedge WDG may be formed to be sequentially in contact with withdrawal members 3535 (refer to FIG. 42) or a plurality of staples 3530 (refer to FIG. 42) disposed in the cartridge 3500, and may serve to sequentially push and raise the staples 3530.

The plurality of fixed pulleys 3120 may be disposed in the first jaw 3101 to be closer to the front of the cartridge 3500, i.e., to the distal end 3101*d* of the first jaw 3101, than the cartridge 3500. For example, a plurality of fixed pulleys 3120 may be disposed in a front space 3101*c* of the first jaw 3101, and details thereof will be described below.

In addition, the end tool 3100 of the surgical instrument of the present embodiment may include one or more members, such as joint members, that connect the jaw 3103 to the connector 3400. Further, in an optional embodiment, the end tool 3100 may include an end tool hub 3108 and a pitch hub 3107.

The end tool hub 3108 may be disposed to connect the end tool 3100 to the straight part 3401 of the connector 3400.

As an example, the end tool hub 3108 may have a pulley shaft JX4 corresponding thereto, and the pulley shaft JX4 may be a pitch rotation shaft. As a specific example, the end tool 3100 may perform a vertical rotational motion around the pulley shaft JX4 based on the drawing. In addition, one or more pulleys may be disposed to be adjacent to the pulley shaft JX4.

The end tool hub 3108 may be in the form of a bar extending from the center of a surface thereof that corresponds to the connector 3400, i.e., a bar extending from the center of a disk-shaped main region. The pulley shaft JX4 and a pulley shaft JX5 different from the pulley shaft JX4 may further correspond to a region of the bar.

The pitch hub 3107 is connected to the end tool hub 3108 and the jaw 3103. The pitch hub 3107 may be axially coupled to the end tool hub 3108 with respect to one pulley shaft, i.e., the pulley shaft JX4. The pitch hub 3107 may rotationally move around one pulley shaft, i.e., the pulley shaft JX4 while connected to the end tool hub 3108. That is, the end tool 3100 may perform a pitch motion as the pitch hub 3107 rotates around one pulley shaft, i.e., the pulley shaft JX4 with respect to the end tool hub 3108.

Further, the jaw 3103 of the end tool 3100 may be axially coupled to the pitch hub 3107 with respect to one pulley shaft, i.e., a pulley shaft JX1. The jaw 3103 may rotate around one pulley shaft, i.e., the pulley shaft JX1 while connected to the pitch hub 3107. That is, the jaw 3103 of the end tool 3100 may rotate around one pulley shaft, i.e., the pulley shaft JX1 with respect to the pitch hub 3107, thereby performing a yaw motion.

As a result, the yaw motion of the end tool 3100 includes a rotational motion of the jaw 3103 around one pulley shaft, i.e., the pulley shaft JX1 with respect to the pitch hub 3107, and the pitch motion of the end tool 3100 includes a rotational motion of the jaw 3103 coupled to the pitch hub 3107, which occurs as the pitch hub 3107 rotates around one pulley shaft, i.e., the pulley shaft JX4 together with the end tool hub 3108.

The pitch hub 3107 may include a first hub 3107a and a second hub 3107b.

The first hub 3107a of the pitch hub 3107 may be connected to the jaw 3103. As an example, the first hub 3107a may be elongated to connect to one region of the first jaw 3101, and specifically, may have two bars that are formed side by side to face each other and coupled to each other by placing one region of the first jaw 3101 therebetween.

The second hub 3107b of the pitch hub 3107 may be connected to the end tool hub 3108, for example, may have two bars that are formed side by side to face each other, and may be coupled to each other by placing one region of the end tool hub 3108 therebetween.

As described above, the pulley shaft JX5 is different from one pulley shaft, i.e., the pulley shaft JX4 may be disposed in the end tool hub 3108 to be spaced apart from the pulley shaft JX4 and closer to the connector 3400 (refer to FIG. 22) than the pulley shaft JX4. The pulley shaft JX4 and the pulley shaft JX5 may have axes in directions parallel to each other.

A pulley shaft JX2, which is different from the pulley shaft JX1, is disposed in the pitch hub 3107 in a direction adjacent to and parallel to the pulley shaft JX1. In addition, a pulley shaft JX3 and the pulley shaft JX4 may be formed in a direction different from (for example, intersecting or orthogonal to) the direction in which the pulley shaft JX1 and the pulley shaft JX2 are disposed, and may be sequentially disposed in a direction toward (or away from the operation member) the connector 1400.

The pulley shaft JX4 may be a pitch motion shaft of the end tool 3100, and the pulley shaft JX1 may be a yaw motion shaft.

The pulley shaft JX3 and the pulley shaft JX5 may be pitch auxiliary pulley shafts, and the pulley shaft JX2 may be a yaw auxiliary pulley shaft. One or more driving wires, such as a wire configured to transmit a driving force for a pitch motion or a yaw motion may have at least one region in contact with or wound around the pulley shafts JX1, JX2, JX3, JX4, and JX5.

The pulley shafts JX2, JX3, JX5 adjacent to the pulley shaft JX4, which is a pitch motion shaft, and the pulley shaft JX1, which is a yaw motion shaft, may control paths along which the driving wires are wound around the pulley shaft JX4 and the pulley shaft JX1 to secure the efficiency of the arrangement of the driving wires and stabilize the paths for transmitting forces through the driving wires.

In addition, at least one region of the forward-moving wire 3110 may be in contact with or wound around the pulley shafts JX1, JX2, JX3, JX4, and JX5.

A more detailed description of the arrangement of the pulley shafts JX1, JX2, JX3, JX4, and JX5 will be provided below.

One or more switching pulley shafts AX1 and AX2 may be disposed in the end tool 3100, and one or more pulleys corresponding to the switching pulley shafts AX1 and AX2 may be disposed.

For example, the switching pulley shafts AX1 and AX2 may be disposed in the jaw 3103, specifically, in the proximal end 3101p side of the first jaw 3101, and may be disposed closer to the distal end 3101d of the first jaw 3101 than at least the above-described pulley shafts JX1, JX2, JX3, JX4, and JX5.

The switching pulley shafts AX1 and AX2 may be shafts formed in parallel to each other, and may be disposed to have different backward and forward positions with respect to each other such that the switching pulley shaft AX1 and the switching pulley shaft AX2 are sequentially disposed with respect to the distal end 3101d of the first jaw 3101 and some regions of the switching pulley shaft AX1 and the switching pulley shaft AX2 are overlap each other.

The switching pulley shafts AX1 and AX2 may be regions where at least one region of the forward-moving wires 3110 is wound or comes into contact to organize and guide the path of the forward-moving wire 3110 before entering the pulley shafts JX1, JX2, JX3, JX4, and JX5. A more detailed description of the arrangement of the switching pulley shafts AX1 and AX2 will be provided below.

As shown in FIG. 27, the first forward-moving wire 3111 and the second forward-moving wire 3112 may be correspondingly wound around the first fixed pulley 3121 and the second fixed pulley 3122 in the first jaw 3101 to be redirected, and connected to the rear of the end tool 3100 via at least one region of each of the switching pulley shafts AX1 and AX2 and the pulley shafts JX1, JX2, JX3, JX4, and JX5. Furthermore, the first forward-moving wire 3111 and the second forward-moving wire 3112 may further extend to the operator 3200 (refer to FIG. 22) via the connector 3400 to be precisely controlled. Accordingly, precise motion control of the operation member 3140 may be easily implemented, and details thereof will be described below.

The jaw 3103 of the end tool 3100 will be described in more detail.

FIG. 28 is a perspective view schematically illustrating the second jaw of the end tool of FIG. 23.

The second jaw 3102 may be formed in an elongated bar shape as a whole, and for example, the second jaw 3102 may be formed in a rod shape to correspond to the first jaw 3101 in at least one region.

A proximal end 3102p of the second jaw 3102 may include a region that is coupled to the first jaw 3101. As an example, the proximal end 3102$p$ is formed to be rotatable around the one shaft JX of the proximal end 3102$p$ with respect to the first jaw 3101.

The second jaw 3102 may have various forms, and as a specific example, a plurality of anvil grooves may be formed in at least one region of a surface of the second jaw 3102 facing the first jaw 3101, and the anvil groove may have a shape corresponding to the shape of the staple 3530.

The anvil groove of the second jaw 3102 may serve as a support for allowing the staple 3530 to be bent when the operation member 3140 push and raise the staple 3530 during a staple motion.

The second jaw 3102 includes a guide groove 3102$a$. The guide groove 3102$a$ may have a shape elongated in a longitudinal direction of the second jaw 3102.

The guide groove 3102$a$ may be formed to guide the operation member 3140, and may be a groove passing through a region facing the operation member 3140. Through this, one region of the operation member 3140, such as at least one region of the body 3142 of the operation member 3140, or a first clamp 3146 connected thereto may pass through the guide groove 3102$a$ to exit to the outside of the second jaw 3102. When the operation member 3140 moves forward, the first clamp 3146 may pass through the guide groove 3102$a$ of the second jaw 3102 to be exposed to the outside of the second jaw 3102, and may come into contact with an upper surface of the second jaw 3102 or apply pressure thereto. As the operation member 3140 moves, the first clamp 3146 applies pressure on the upper surface of the second jaw 3102 and a second clamp 3147 to be described below applies pressure on a lower surface of the first jaw 3101 such that a gap between the second jaw 3102 and the first jaw 3101 decreases, allowing the second jaw 3102 to naturally remain in a closed state with respect to the first jaw 3101.

FIG. 29 is a perspective view schematically illustrating the first jaw of the end tool of FIG. 23. FIG. 30 is a plan view schematically illustrating the first jaw of the end tool of FIG. 23.

Referring to FIGS. 29 and 30 and the like, the first jaw 3101 is formed in an elongated bar shape as a whole, and a rotation shaft may be disposed in the proximal end such that the first jaw 3101 is rotationally movable, and such a rotation shaft may correspond to the rotation shaft JX formed in the second jaw 3102 described above. In addition, the cartridge 3500 (refer to FIG. 25) may be accommodated closer to the distal end 3101$d$ side than the rotation shaft.

For example, the first jaw 3101 may be formed entirely in the form of a hollow box with one surface (upper surface) thereof is removed, such that a cartridge accommodation part 3101$a$ capable of accommodating the cartridge 3500 may be formed inside the first jaw 3101. That is, the first jaw 3101 may be formed in a substantially "U" shape in cross section.

A guide groove 3101$h$ may be formed in a bottom surface of the first jaw 3101, the bottom surface opposite to an upper open region formed by removing one surface. Specifically, the guide groove 3101$h$ may be formed to guide a linear motion of the operation member 3140.

The guide groove 3101$h$ may be formed to guide the operation member 3140, and may be a groove formed to pass through a region facing the operation member 3140. Through this, one region of the operation member 3140, such as at least one region of the body 3142 of the operation member 3140, or the second clamp 3147 connected thereto may pass through the guide groove 3101$h$ to exit to the outside of the first jaw 3101. When the operation member 3140 moves forward, the second clamp 3147 may pass through the guide groove 3101$h$ of the first jaw 3101 to be exposed to the outside of the first jaw 3101, and may come into contact with the lower surface of the first jaw 3101 or apply pressure thereto. As the operation member 3140 moves, the second clamp 3147 applies pressure on the lower surface of the first jaw 3101 and the first clamp 3146 applies pressure on the upper surface of the second jaw 3102 such that a gap between the second jaw 3102 and the first jaw 3101 decreases, allowing the second jaw 3102 to naturally remain in a closed state with respect to the first jaw 3101 (refer to FIGS. 20A, 20B, and 20C).

In an optional embodiment, the first jaw 3101 may include a window 3101$b$. After operating the operation member 3140 or using the end tool 3100, the second clamp 3147 of the operation member 3140 may be located corresponding to the window 3101$b$, and the coupled state of the first jaw 3101 and the operation member 3140 may be released.

The first jaw 3101 may include the front space 3101$c$ located ahead of the cartridge accommodation part 3101$a$.

For example, the front space 3101$c$ may be disposed closer to the distal end 3101$d$ of the first jaw 3101 than the cartridge accommodation part 3101$a$. The plurality of fixed pulleys 3120 may be disposed in the front space 3101$c$, for example, the first fixed pulley 3121 and the second fixed pulley 3122 may be disposed in the front space 3101$c$ (refer to, for example, FIGS. 23 to 27).

Two outer side surfaces of the front space 3101$c$ include a first side surface 3101$t$1 and a second side surface 3101$t$2, and the first fixed pulley 3121 and the second fixed pulley 3122 may be disposed to correspond to the first side surface 3101$t$1 and the second side surface 3101$t$2, respectively.

Each of the first side surface 3101$t$1 and the second side surface 3101$t$2 may be formed to have an inclined shape. For example, the first side surface 3101$t$1 and the second side surface 3101$t$2 may be shaped such that a gap therebetween decreases as it moves downward, instead of being parallel to each other with the same gap. As a specific example, the gap between the first side surface 3101T1 and the second side surface 3101$t$2 may be formed to be smaller in a direction away from the second jaw 3102.

Since the first fixed pulley 3121 and the second fixed pulley 3122 are disposed to correspond to the first side surface 3101$t$1 and the second side surface 3101$t$2, respectively, the first fixed pulley 3121 and the second fixed pulley 3122 may be disposed to have an inclined shape such that a gap therebetween decreases in a direction away from the second jaw 3102 (refer to FIG. 23). The first fixed pulley 3121 and the second fixed pulley 3122 may be symmetrically shaped and may have the same size as each other.

In addition, a first path 3101$w$1 and a second path 3101$w$2 may be formed adjacent to the front space 3101$c$. For example, the first path 3101$w$1 and the second path 3101$w$2 may have the form of through holes formed in a barrier wall, and may be regions through which the first forward-moving wire 3111 and the second forward-moving wire 3112 pass, respectively.

In an optional embodiment, when a backward-moving wire (refer to, for example, FIG. 40) is disposed, the first jaw 3101 may include a rear side path 3101R corresponding to the backward-moving wire.

In addition, the first jaw 3101 may include a coupling region 3101$z$ in a region adjacent to the proximal end 3101$p$. The coupling region 3101$z$ is a region coupled to the pitch hub 3107 and may be in the form of a plate elongated to correspond to, for example, the first hub 3107$a$ of the pitch hub 3107. The coupling region 3101$z$ may be disposed and coupled between two bars formed on the first hub 3107$a$ of the pitch hub 3107.

The operation member 3140 will now be described in detail.

FIG. 31 is a perspective view illustrating the operation member of the end tool of FIG. 23. FIG. 32 is a perspective view of the operation member of FIG. 31 viewed from another direction. FIG. 33 is a front view of the operation member of FIG. 31 viewed in one direction.

The operation member 3140 may include the body 3142, the first clamp 3146, and the second clamp 3147. Meanwhile, the operation member 3140 may be used together with the wedge WDG (refer to FIGS. 26 and 27). For example, the wedge WDG may be prepared separately from the operation member 3140 and then disposed adjacent to the operation member 3140 in the first jaw 3101. In addition, as another example, the operation member 3140 and the wedge WDG may be integrally formed. In the present specification, for convenience of description, the operation member 3140 and the wedge WDG will be described and illustrated in the drawings with the assumption that the operation member 3140 and the wedge WDG are prepared separately.

The wedge WDG may be disposed on at least one side of the body 3142 and may be formed to have a predetermined inclined surface. That is, the wedge WDG may be formed to be inclined by a certain degree with respect to the extension direction of the end tool 3100. In other words, the wedge WDG may be formed to have a greater height at a proximal end 3101$p$ side of the first jaw 3101 than a distal end 3101$d$ side of the first jaw 3101.

The wedge WDG may be formed to be sequentially in contact with the withdrawal members 3535 (refer to FIG. 42) or the plurality of staples 3530 (refer to FIG. 42) and may serve to sequentially push and raise the staples 3530.

The body 3142 may be in the form of an elongated column, such as a plate-shaped column. In addition, a blade region 3142$a$ may be formed in one region of the body 3142, and an edge sharply formed to cut tissue may be formed in the blade region 3142$a$. The tissue disposed between the first jaw 3101 and the second jaw 3102 may be cut as at least a portion of the edge formed in the blade region 3142$a$ of the body 3142 is withdrawn to the outside of the first jaw 3101 and the cartridge 3500.

The first clamp 3146 may be formed in one region of the body 3142, and the second clamp 3147 may be formed in another region different from the one region. For example, the body 3142 may be disposed between the first clamp 3146 and the second clamp 3147.

The first clamp 3146 and the second clamp 3147 may be formed to have a region with a width at least greater than that of the body 3142. Accordingly, the first clamp 3146 may be inserted into and pass through the guide groove 3102$a$ formed in the second jaw 3102 in the longitudinal direction to be deposed or brought into contact with the upper surface of the second jaw 3102 and, at the same time, the second clamp 3147 may be inserted into and pass through the guide groove 3101$h$ formed in the first jaw 3101 in the longitudinal direction to be deposed or brought into contact with the lower surface of the first jaw 3101, so that the first clamp 3146 and the second clamp 3147 may move. Thus, when the operation member 3140 moves, the first clamp 3146 and the second clamp 3147 may apply forces in directions that bring the second jaw 3102 and the first jaw 3101 closer to each other.

As a result, when the operation member 3140 moves from the proximal end 3101$p$ of the first jaw 3101 toward the distal end 3101$d$ of the first jaw 3101, a motion of decreasing a distance between the second jaw 3102 and the first jaw 3101, i.e., a closing motion of the jaw 3103, may be naturally implemented through the first clamp 3146 and the second clamp 3147.

The first clamp 3146 and the second clamp 3147 may be placed at different positions with respect to a forward-facing direction of the body 3142. For example, the second clamp 3147 may be located further forward than the first clamp 3146, for example, the second clamp 3147 may be located closer to the distal end 3101$d$ of the first jaw 3101 than the first clamp 3146 when the operation member 3140 is disposed in the first jaw 3101. Accordingly, the operation member 3140 may move forward while the first jaw 3101 and second jaw 3102 are in the closed state, so that the first jaw 3101 and second jaw 3102 can be maintained with greater efficiency and stability while performing stapling.

A first connection region 3140$p1$ and a second connection region 3140$p2$ may be formed in one region of the body 3142, such as one region in a front side of the body 3142, specifically, a region of the body 3142 facing the distal end 3101$d$ of the first jaw 3101.

The first connection region 3140$p1$ and the second connection region 3140$p2$ may be regions to which the first forward-moving wire 3111 and the second forward-moving wire 3112 are connected, respectively, and may each be in the form of a fixing groove such that respective one end portion region of the first forward-moving wire 3111 and the second forward-moving wire 3112 is accommodated or fixed thereto. When the first forward-moving wire 3111 and the second forward-moving wire 3112 are connected to the first connection region 3140$p1$ and the second connection region 3140$p2$ to pull the first forward-moving wire 3111 and the second forward-moving wire 3112, respectively, forces pulling the first forward-moving wire 3111 and the second forward-moving wire 3112 are transmitted to the operation member 3140 through the first connection region 3140$p1$ and the second connection region 3140$p2$ so that the operation member 3140 may move, i.e., move forward.

In an optional embodiment, the first connection region 3140$p1$ and the second connection region 3140$p2$ may be formed on side portions 3143 of the operation member 3140, respectively.

The side portions 3143 may be formed to protrude outward from both side surfaces of the body 3142, respectively. By forming the first connection region 3140$p1$ and the second connection region 3140$p2$ on the side portions 3143 formed to protrude from both sides of the body 3142, spaces for respectively connecting the first forward-moving wire 3111 and the second forward-moving wire 3112 to the first connection region 3140$p1$ and the second connection region 3140$p2$ can be easily secured.

Further, by forming the first connection region 3140$p1$ and the second connection region 3140$p2$ on the side portions 3143 formed on both sides of the body 3142, and connecting the first forward-moving wire 3111 and the second forward-moving wire 3112 to the first connection region 3140$p1$ and the second connection region 3140$p2$, the first forward-moving wire 3111 and the second forward-moving wire 3112 can be pulled from both sides of the body 3142, and also from symmetrical positions, so that the forward movement of the operation member 3140 can be precisely controlled.

In an optional embodiment, a connection region for the backward-moving wire may be formed in a rear side region of the body 3142.

FIG. 34 is a schematic perspective view illustrating a portion of the end tool of FIG. 23. FIG. 35 is a front view of FIG. 34 viewed in one direction.

Referring to FIGS. 34 and 35, the first fixed pulley 3121 and the second fixed pulley 3122 may be disposed to have an inclined shape without being disposed in parallel to each other. For example, as a specific example, based on the drawings, the first fixed pulley 3121 and the second fixed pulley 3122 may be disposed such that a gap therebetween decreases in a direction away from the second jaw 3102 (refer to FIG. 23).

Specifically, the first fixed pulley 3121 and the second fixed pulley 3122 may be disposed to face each other in the front space 3101c located further forward than the cartridge accommodation part 3101a of the first jaw 3101, and may be disposed symmetrically to each other as a specific example. In addition, the first fixed pulley 3121 and the second fixed pulley 3122 may be formed to have the same size.

Two outer side surfaces of the front space 3101c include the first side surface 3101t1 and the second side surface 3101t2, and the first fixed pulley 3121 and the second fixed pulley 3122 may be disposed to correspond to the first side surface 3101t1 and the second side surface 3101t2, respectively.

Each of the first side surface 3101t1 and the second side surface 3101t2 may be formed to have an inclined shape. For example, the first side surface 3101t1 and the second side surface 3101t2 may be shaped such that a gap therebetween decreases as it moves downward, instead of being parallel to each other with the same gap. As a specific example, the gap between the first side surface 3101t1 and the second side surface 3101t2 may be formed to be gradually smaller in a direction away from the second jaw 3102 (refer to FIG. 23). In addition, the first side surface 3101t1 and the second side surface 3101t2 may have shapes symmetrical to each other.

The first forward-moving wire 3111 and the second forward-moving wire 3112 may be correspondingly wound around the first fixed pulley 3121 and the second fixed pulley 3122, and the regions of the first forward-moving wire 3111 and the second forward-moving wire 3112 emerging from being wound around the lower sides of the first fixed pulley 3121 and the second fixed pulley 3122 may be directed to the first connection region 3140p1 and the second connection region 3140p2 of the operation member 3140 described above, respectively.

With such a shape, the characteristic of balanced arrangement of the first fixed pulley and the second fixed pulley 3121 and 3122 and the first forward-moving wire and the second forward-moving wire 3111 and 3112 with respect to the moving direction of the operation member 3140 may be improved, and for example, the symmetrical shape may be easily implemented. In addition, shaking or rotational moment generated when pulling the first forward-moving wire 3111 and the second forward-moving wire 3112 may be reduced, so that the end tool 3100 may be reduced or prevented from shaking.

In addition, the end tool 3100 may be shaped such that a width of, for example, one side of the first jaw 3101, which is one side of the jaw 3103, specifically, a width of a main region of the lower side is reduced, so that the end tool 3100 can be implemented in a compact structure as a whole.

Further, the first fixed pulley 3121 and the second fixed pulley 3122 may be disposed to have an inclined shape without being disposed in parallel to each other, which allows the two forward-moving wires 3111 and 3112 to emerge from being wound around the lower sides of the first fixed pulley 3121 and the second fixed pulley 3122 and be connected to the operation member 3140, i.e., disposed in a lower side region of the cartridge 3500 after passing through the first path 3101w1 and the second path 3101w2. Another regions of the two forward-moving wires 3111 and 3112 may emerge from being wound around the upper sides of the first fixed pulley 3121 and the second fixed pulley 3122 and may be respectively disposed on both sides of the cartridge 3500, i.e., in spaces between the cartridge 3500 and both side surfaces of the first jaw 3101.

By arranging the two forward-moving wires 3111 and 3112 in this manner, the forward-moving wires 3111 and 3112 are avoided from being fixed to the center line of the operation member 3140, so that the operation member 3140 can be implemented in a compact form while maintaining durability.

In addition, by arranging the two forward-moving wires 3111 and 3112 correspondingly to the first fixed pulley 3121 and the second fixed pulley 3122 formed in an inclined shape, such as a symmetrical shape, maximum tensions applied to the two forward-moving wires 3111 and 3112 can be equalized or made almost similar to each other, this may enhance the fatigue life of each wire.

In addition, one regions of the two forward-moving wires 3111 and 3112 can be controlled to symmetrically pass through the lower side of the cartridge 3500, and another regions thereof can be controlled to symmetrically pass through both sides of the cartridge 3500, and accordingly, unwanted moment or rotational forces generated when pulling the two forward-moving wires 3111 and 3112 may be reduced or prevented from causing unintended movement or shaking of the end tool 3100 or the surgical instrument 3000 including the same.

Meanwhile, referring to FIG. 35, the first fixed pulley 3121 and the second fixed pulley 3122 may be disposed in a slanted shape, i.e., an inclined shape, without being disposed in parallel to each other.

For example, each of the first fixed pulley 3121 and the second fixed pulley 3122 may be disposed to be inclined at an angle of 35 degrees (deg) to 51 degrees (deg) relative to a vertical line (a line parallel to a z-axis) based on FIG. 35.

Further, in other words, a central axis of the first fixed pulley 3121 and a central axis of the second fixed pulley 3122 may be inclined at an angle without being parallel to each other, and for example, the central axis of the first fixed pulley 3121 and the central axis of the second fixed pulley 3122 may be disposed to be inclined at an angle of 78 degrees to 110 degrees.

Further, in other words, as shown in FIG. 35, the first fixed pulley 3121 and the second fixed pulley 3122 may be shaped to be inclined, forming an adjacent angle DG.

The adjacent angle DG may range from 70 degrees (deg) to 102 degrees (deg).

When the adjacent angle DG is less than 70 degrees or more than 102 degrees, a diameter of each of the first fixed pulley 3121 and the second fixed pulley 3122 accommodated in a predetermined space of the first jaw 3101 becomes smaller, which causes the stress applied on the forward-moving wires 3111 and 3112 to be increased, and the maximum allowable tension and durability of the forward-moving wires 3111 and 3112 to be reduced, and thus, the adjacent angle DG may range from 70 degrees (deg) to 102 degrees (deg), in a specific example, the adjacent angle DG may be 86 degrees (deg). Meanwhile, the adjacent angle DG is applicable to embodiments to be described below without change.

The arrangement relationship of the operation member 3140, the plurality of forward-moving wires 3110, and the plurality of fixed pulleys 3120 will now be further described.

FIG. 36 is a schematic plan view for describing the operation member, the fixed pulley, and the forward-moving wire of the end tool of FIG. 23. FIG. 37 is a schematic perspective view for describing the operation member, the fixed pulley, and the forward-moving wire of the end tool of FIG. 23.

As described above, the first fixed pulley 3121 and the second fixed pulley 3122 are disposed in the front space 3101c of the first jaw 3101, and each of the first fixed pulley 3121 and the second fixed pulley 3122 may be fixed to the first jaw 3101 and immobile, or fixed so as to be rotatable about one shaft.

The first forward-moving wire 3111 and the second forward-moving wire 3112 may be wound around outer circumferential surfaces of the first fixed pulley 3121 and the second fixed pulley 3122, respectively, and a groove may be formed in each of the outer circumferential surfaces of the first fixed pulley 3121 and the second fixed pulley 3122.

The first fixed pulley 3121 and the second fixed pulley 3122 may be disposed closer to the distal end 3101d of the first jaw 3101 at least than the operation member 3140.

The first forward-moving wire 3111 may extend to have a length in the longitudinal direction of the first jaw 3101, and one end portion region thereof may extend to the proximal end 3101p of the first jaw 3101, and pass through the switching pulley shafts AX1 and AX2 or switching pulleys coupled thereto and the pulley shafts JX1, JX2, JX3, JX4, and JX5 or pulleys coupled thereto to be connected to the inside of the driving part, such as the operator 3200 (refer to FIG. 23), so that the first forward-moving wire 3111 can be pulled through manipulation of the operator 3200.

Another end portion of the first forward-moving wire 3111 may extend in a direction toward the distal end 3101d of the first jaw 3101 along the longitudinal direction of the first jaw 3101, emerge from the lower side of the first fixed pulley 3121 after being wound around the upper side of the first fixed pulley 3121 while coming into contact therewith, and extend in a direction toward proximal end 3101p of the first jaw 3101 to be connected and fixed to the first connection region 3140p1 of the operation member 3140.

In an optional embodiment, among the regions of the first forward-moving wire 3111, the region extending to the distal end 3101d of the first jaw 3101 and being directed to the upper side of the first fixed pulley 3121 may be parallel to the region emerging from the lower side of the first fixed pulley 3121, extending toward the proximal end 3101p of the first jaw 3101, and being directed toward the first connection region 3140p1 of the operation member 3140.

Accordingly, a pulling force can be effectively transmitted to the operation member 3140 when pulling the first forward-moving wire 3111 toward the proximal end 3101p. In addition, as an example, when pulling the first forward-moving wire 3111 toward the proximal end 3101p, a ratio of the pulling force to the corresponding forward-moving distance of the operation member 3140 may be precisely controlled at a predetermined ratio. As a specific example, when pulling the first forward-moving wire 3111 toward the proximal end 3101p, the ratio of the pulling force to the forward-moving distance of the operation member 3140 may be easily controlled to a value equal to, or substantially equal or similar to 1:1.

The second forward-moving wire 3112 may extend to have a length in the longitudinal direction of the first jaw 3101, and one end portion region thereof may extend to the proximal end 3101p of the first jaw 3101, and pass through the switching pulley shafts AX1 and AX2 or switching pulleys coupled thereto and the pulley shafts JX1, JX2, JX3, JX4, and JX5 or pulleys coupled thereto to be connected to the inside of the driving part, such as the operator 3200 (refer to FIG. 23), so that the second forward-moving wire 3112 can be pulled through manipulation of the operator 3200.

Another end portion of the second forward-moving wire 3112 may extend in a direction toward the distal end 3101d of the first jaw 3101 along the longitudinal direction of the first jaw 3101, emerge from the lower side of the second fixed pulley 3122 after being wound around the upper side of the second fixed pulley 3122 while coming into contact therewith, and extend in a direction toward proximal end 3101p of the first jaw 3101 to be connected and fixed to the second connection region 3140p2 of the operation member 3140.

In an optional embodiment, among the regions of the second forward-moving wire 3112, the region extending to the distal end 3101d of the first jaw 3101 and being directed to the upper side of the second fixed pulley 3122 may be parallel to the region emerging from the lower side of the second fixed pulley 3122, extending toward the proximal end 3101p of the first jaw 3101, and being directed toward the second connection region 3140p2 of the operation member 3140.

Accordingly, a pulling force can be effectively transmitted to the operation member 3140 when pulling the second forward-moving wire 3112 toward the proximal end 3101p.

As shown in FIGS. 36 and 37, when the first forward-moving wire 3111 and the second forward-moving wire 3112 are pulled in a first direction D1, one region of each of the first forward-moving wire 3111 and the second forward-moving wire 3112 may move in the first direction D1, and accordingly, the region of the forward-moving wire 3110 emerging from the lower sides of the first fixed pulley 3121 and the second fixed pulley 3122 after being wound around the upper sides thereof may move in a second direction D2, which is the opposite direction of the first direction D1. Accordingly, forces of the first forward-moving wire 3111 and the second forward-moving wire 3112 may be transmitted to the first connection region 3140p1 and the second connection region 3140p2 connected to the first forward-moving wire 3111 and the second forward-moving wire 3112, and the forces cause the operation member 3140 also move in a direction K1, which is the same direction as the second direction D2, i.e., move forward.

FIGS. 38 and 39A, 39B, and 39C are schematic views for describing an operation of the operation member of the end tool of FIG. 23.

Referring to FIGS. 38 and 39A, 39B, and 39C, for convenience of description, the first jaw 3101 is excluded, and the first forward-moving wire 3111, the second forward-moving wire 3112, the first fixed pulley 3121, the second fixed pulley 3122, and the operation member 3140 are illustrated.

Figure 38:
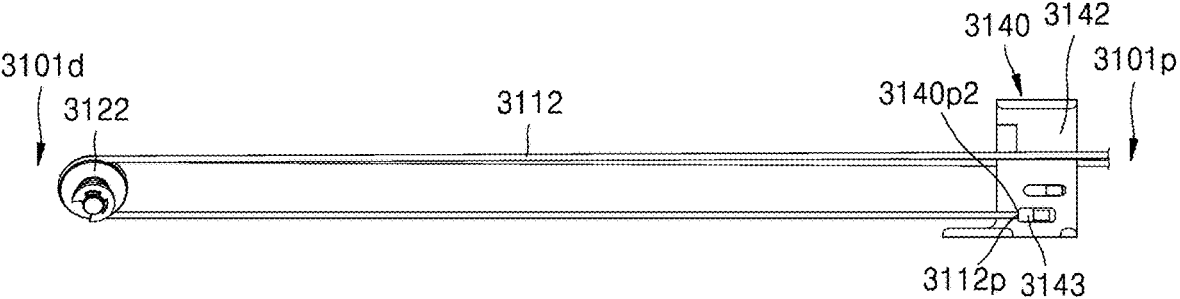
FIGS. 38, 39A, 39B and 39C are schematic views for describing an operation of the operation member of the end tool of FIG. 23.
Figure 39A:
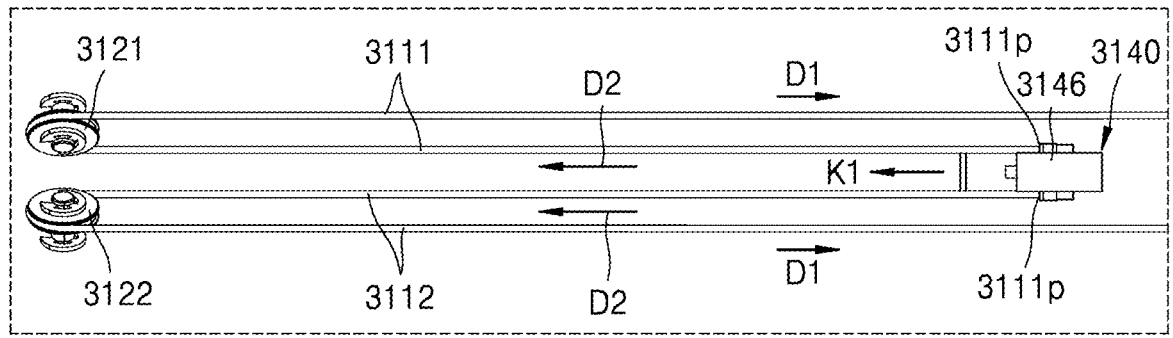
Figure 39B:
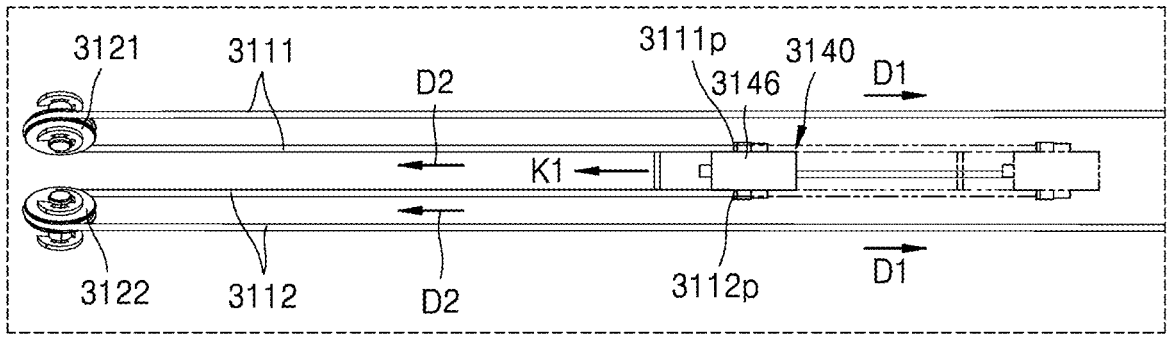
Figure 39C:
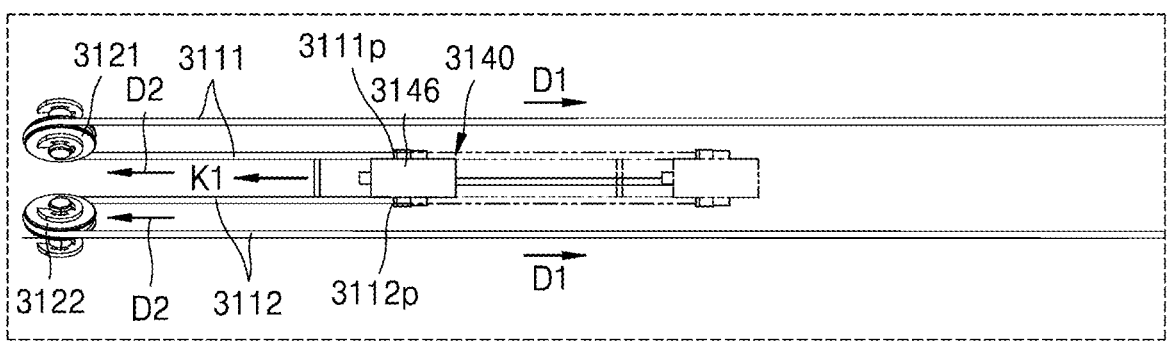

Based on FIG. 38, the operation member 3140 may move in a leftward direction, i.e., move forward toward the distal end 3101d, and this forward movement is illustrated sequentially in FIGS. 39A, 39B, and 39C.

As shown in FIG. 39A, when the first forward-moving wire 3111 and the second forward-moving wire 3112 are pulled in the first direction D1, one region of each of the first forward-moving wire 3111 and the second forward-moving wire 3112 is pulled in the first direction D1, and thus the regions of the first forward-moving wire 3111 and the second forward-moving wire 3112 emerging from the lower sides of the first fixed pulley 3121 and the second fixed pulley 3122 after being wound around the upper sides thereof move in the second direction D2, which is the opposite direction of the first direction D1. Accordingly, forces of the first forward-moving wire 3111 and the second forward-moving wire 3112 are transmitted respectively to the first connection region 3140*p*1 and the second connection region 3140*p*2 respectively connected to the first forward-moving wire 3111 and the second forward-moving wire 3112, and the forces cause the operation member 3140 to move in the direction K1, which is the same direction as the second direction D2, i.e., move forward, thereby positioning the operation member 3140 in an advanced position shown in FIG. 39B.

Thereafter, as shown in FIG. 39B, when the first forward-moving wire 3111 and the second forward-moving wire 3112 are pulled further in the first direction D1, one region of the first forward-moving wire 3111 and the second forward-moving wire 3112 is pulled further in the first direction D1, and thus the regions of the first forward-moving wire 3111 and the second forward-moving wire 3112 emerging from the lower sides of the first fixed pulley 3121 and the second fixed pulley 3122 after being wound around the upper sides thereof move further in the second direction D2, which is the opposite direction of the first direction D1. Accordingly, forces of the first forward-moving wire 3111 and the second forward-moving wire 3112 are transmitted respectively to the first connection region 3140*p*1 and the second connection region 3140*p*2 connected to the first forward-moving wire 3111 and the second forward-moving wire 3112, and the forces cause the operation member 3140 to move further in the direction K1, which is the same direction as the second direction D2, i.e., move forward to a further advanced position than in FIG. 39B, thereby positioning the operation member 3140 in the further advanced position shown in FIG. 39C.

Although not shown in the drawings, it will be appreciated of course that the form corresponding to the side view illustrating the operation of the operation member of FIGS. 20A, 20B, and 20C may be applied to the end tool 3100 of the present embodiment either as is or with appropriate modifications.

FIGS. 40 and 41A, 41B, and 41C are views for describing an optional embodiment in which a backward-moving wire is added to the end tool of FIG. 23.

Referring to FIGS. 40 and 41A, 41B, and 41C, the end tool of the present embodiment may further include a backward-moving wire BRW.

Figure 40:
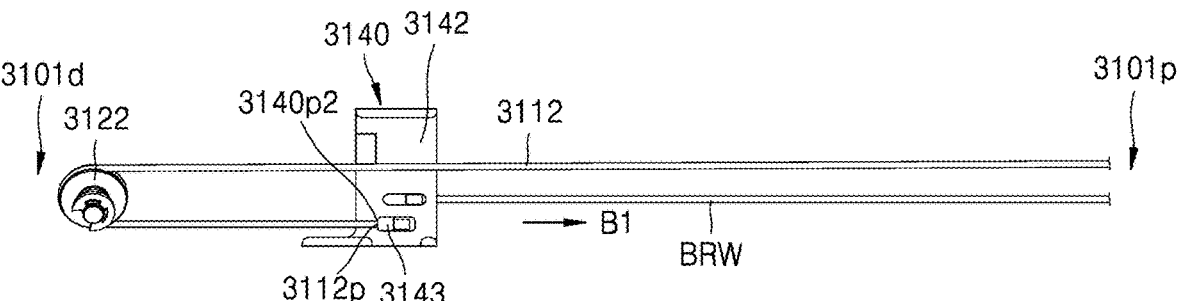
FIGS. 40, 41A, 41B and 41C are views for describing an optional embodiment in which a backward-moving wire is added to the end tool of FIG. 23.

For example, the structure of FIG. 40 may be the structure of FIG. 38 with the addition of the backward-moving wire BRW.

Referring to FIGS. 40 and 41A, 41B, and 41C, for convenience of description, the first jaw 3101 is excluded, and the first forward-moving wire 3111, the second forward-moving wire 3112, the first fixed pulley 3121, the second fixed pulley 3122, the operation member 3140, and the backward-moving wire BRW are illustrated.

Figure 41A:
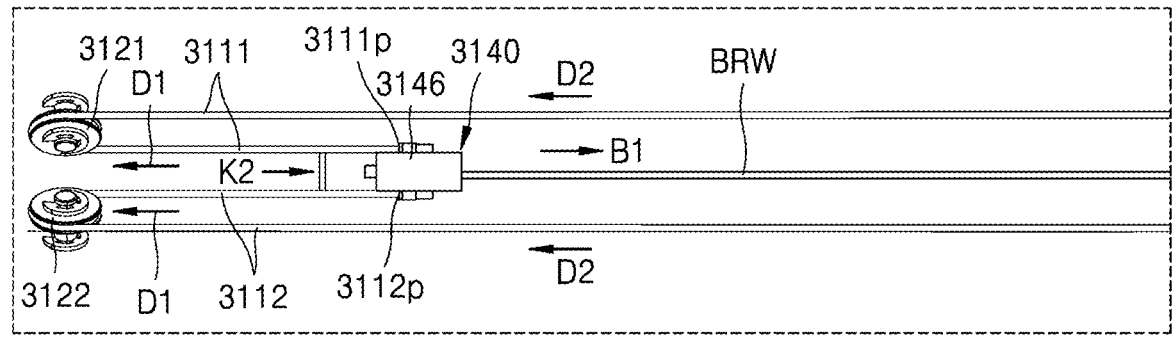
Figure 41B:
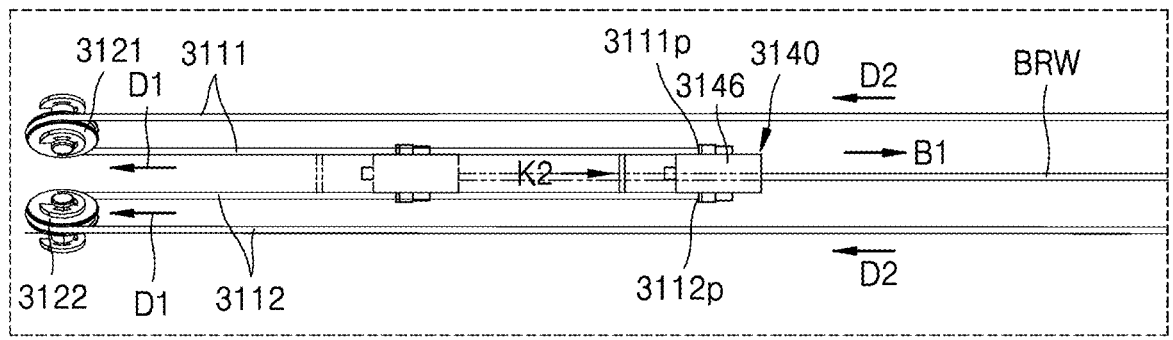
Figure 41C:
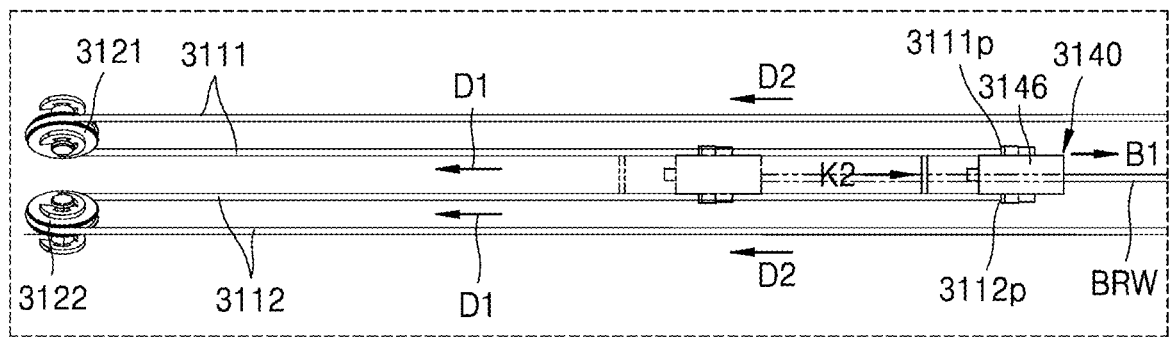

Based on FIG. 40, the operation member 3140 may move in a rightward direction, i.e., move backward toward the proximal end 3101*p*, and this backward movement is illustrated sequentially in FIGS. 41A, 41B, and 41C.

The backward-moving wire BRW may be connected to one region of the operation member 3140 and may be connected, for example, to a rear side of the operation member, specifically, to a region of the blade region 3142*a*, which is opposite to the region in which the edge of the blade region 3142*a* is formed, among regions of the body 3142.

A driving part or driving transmission part (e.g., a wire, a pulley, or the like) capable of pulling the backward-moving wire BRW may be connected to the backward-moving wire BRW, and the backward-moving wire BRW may be operated according to manual or automatic manipulation. For example, the backward-moving wire BRW may be pulled by the operator 3200 (refer to FIG. 22).

By pulling the backward-moving wire BRW. The operation member 3140 may move backward.

For example, as shown in FIG. 41A, the backward-moving wire BRW is pulled in a reverse direction B1 in a state in which the operation member 3140 is located adjacent to the distal end 3101*d* of the first jaw 3101, the operation member 3140 connected to the backward-moving wire BRW moves backward in a direction K2, which is the same direction as the reverse direction B1.

At this point, the first forward-moving wire 3111 and the second forward-moving wire 3112 may be in a state in which a pulling force is not applied.

When the operation member 3140 moves backward (in the direction K2), the region of the first forward-moving wire 3111 and the second forward-moving wire 3112 connected to the first connection region 3140*p*1 and the second connection region 3140*p*2 of the operation member 3140 may move in the first direction D1, which is the same direction as the direction K2, and the regions of the first forward-moving wire 3111 and the second forward-moving wire 3112, which are wound around the lower sides of the first fixed pulley 3121 and the second fixed pulley 3122 and disposed on the upper sides thereof, may move in the second direction D2, which is the opposite direction of the direction K2. Accordingly, the operation member 3140 is in a position as shown in FIG. 41B, having moved backward to be closer to the proximal end 3101*p* compared to its position in FIG. 41A.

Thereafter, as shown in FIG. 41B, when the backward-moving wire BRW is pulled further in the reverse direction B1, the operation member 3140 connected to the backward-moving wire BRW moves backward in the direction K2, which is the same direction as the reverse direction B1. At this point, the first forward-moving wire 3111 and the second forward-moving wire 3112 may be in a state in which a pulling force is not applied. The regions of the first forward-moving wire 3111 and the second forward-moving wire 3112 connected to the first connection region 3140*p*1 and the second connection region 3140*p*2 of the operation member 3140 move in the first direction D1, which is the same direction as the direction K2, and the regions of the first forward-moving wire 3111 and the second forward-moving wire 3112, which are wound around the lower sides of the first fixed pulley 3121 and the second fixed pulley 3122 and disposed on the upper sides thereof, may move in the second direction D2, which is the opposite direction of the direction K2. Accordingly, the operation member 3140 is in a position as shown in FIG. 41C, having moved backward to be closer to the proximal end 3101*p* compared to its position in FIG. 41B.

Further, although not shown in the drawings, it is of course possible that the configuration of FIG. 27 described above may be optionally applied to the end tool 3100 of the present embodiment.

The cartridge 3500 accommodated in the end tool 3100 of FIG. 23 and a stapling motion will now be described in more detail.

FIG. 42 is a perspective view illustrating the first jaw and the cartridge of the surgical instrument of FIG. 22.

Referring to FIGS. 22, 23, 24, 25, and 42 and the like, the cartridge 3500 may be disposed in the first jaw 3101, and for example, the cartridge 3500 may be disposed by being coupled to the cartridge accommodation part 3101*a* of the first jaw 3101. For example, the cartridge 3500 may be integrally formed with the first jaw 3101 while the operation member 3140 is disposed in the first jaw 3101. In addition, in an optional embodiment, the cartridge 3500 may be formed to be mountable to and dismountable from the first jaw 3101.

The cartridge 3500 includes a plurality of staples 3530 therein to perform suturing of tissue, and performs cutting through the operation member 3140. Here, the cartridge 3500 may include a cover 3510, the staples 3530, and the withdrawal members 3535.

The cover 3510 may be formed to cover an upper portion of the cartridge accommodation part 3101*a* of the first jaw 3101. Staple holes 3510*s* through which the plurality of staples 3530 may be ejected to the outside may be formed in the cover 3510. As the staples 3530, which are accommodated inside the cartridge accommodation part 3101*a* before a stapling operation, are pushed and raised upward by the operation member 3140 during a stapling motion, and pass through the staple holes 3510*s* of the cover 3510 to be withdrawn to the outside of the cartridge 3500, stapling may be performed.

Meanwhile, a slit 3510*w* may be formed in the cover 3510 along a longitudinal direction of the cover 3510. The blade region 3142*a* of the body 3142 of the operation member 3140 may protrude out of the cartridge 3500 through the slit 3510*w*. As the blade of the body 3142 of the operation member 3140 passes along the slit 3510*w*, staple-completed tissue may be cut.

In an optional embodiment, the cartridge 3500 may include a case 3520, and the cartridge 3500 may be disposed in the case 3520 after the case 3520 is disposed in the cartridge accommodation part 3101*a* of the first jaw 3101.

The plurality of staples 3530 may be disposed inside the cartridge accommodation part 3101*a* of the first jaw 3101. As the operation member 3140 linearly moves in one direction, the plurality of staples 3530 are sequentially pushed and raised from the inside of the cartridge accommodation part 3101*a* of the first jaw 3101 to the outside, thereby performing suturing, that is, stapling. Here, the staples 3530 may include a material that is durable and does not have an abnormal effect on the human body, such as titanium, stainless steel, or the like.

Meanwhile, the withdrawal members 3535 may be further disposed between the cartridge accommodation part 3101*a* of the first jaw 3101 and the staples 3530. In other words, it may be said that the staple 3530 is disposed above the withdrawal member 3535. In this case, the operation member 3140 linearly moves in one direction to push and raise the withdrawal member 3535, and the withdrawal member 3535 may push and raise the staple 3530.

As such, the operation member 3140 may be described as pushing and raising the staples 3530 in both the case in which the operation member 3140 directly pushes and raises the staples 3530 and the case in which the operation member 3140 pushes and raises the withdrawal members 3535 and the withdrawal members 3535 pushes and raises the staples 3530 (i.e., the operation member 3140 indirectly pushes and raises the staples 3530).

As described above, the operation member 3140 may be disposed inside the cartridge accommodation part 3101*a* of the first jaw 3101. In addition, the operation member 3140 may include the wedge WDG or may be used in conjunction with wedge WDG, and when the operation member 3140 moves, the wedge WDG may move together therewith so that the wedge WDG may directly push and raise the staple 3530, or the wedge WDG may push and raise the withdrawal member 3535 to push and raise the staple 3530.

As described above, the movement of the first forward-moving wire 3111 and the second forward-moving wire 3112, i.e., the pulling of the first forward-moving wire 3111 and the second forward-moving wire 3112 allows the operation member 3140 connected thereto to move forward toward the distal end 3101*d* of the first jaw 3101.

The forward movement of the operation member 3140 may cause the wedge WDG to push and raise the withdrawal member 3535, which may also cause the staple 3530 to rise, and at the same time, cutting using the blade region 3142*a* of the operation member 3140 may be performed. In addition, in an optional embodiment, in the case of the end tool in which the backward-moving wire BRW is connected to the operation member 3140, the backward-moving wire BRW may be pulled to cause the operation member 3140 to move toward the proximal end 3101*p* of the first jaw 3101.

FIGS. 43 and 44 are views for describing a switching pulley, a yaw pulley, and a pitch pulley of the end tool of the surgical instrument of FIG. 22.

As described above, the end tool 3100 may be connected to the connector 3400, and the end tool 3100 may rotationally move around one shaft and also rotationally move around another shaft with respect to the connector 3400.

For example, the end tool 3100 may perform a pitch motion, i.e., a vertical rotational motion based on FIGS. 23 and 42, and the end tool 3100 may perform a yaw motion, i.e., a horizontal rotational motion based on FIGS. 23 and 42. A rotation shaft of the pitch motion and a rotation shaft of the yaw motion may be located in directions that may intersect or be perpendicular to each other.

As an example, the end tool 3100 may include one or more members, such as joint members, that connect the jaw 3103 to the connector 3400, and may include the end tool hub 3108 and the pitch hub 3107.

The end tool hub 3108 may be disposed to connect the end tool 3100 to the straight part 3401 of the connector 3400. As an example, the end tool hub 3108 may have the pulley shaft JX4 corresponding thereto, and the pulley shaft JX4 may be a rotation shaft of the pitch motion. As a specific example, the end tool 3100 may rotationally move around the pulley shaft JX4, the pitch hub 3107 may rotationally move around the pulley shaft JX4, and the jaw 3103 may be connected to the pitch hub 3107 to perform a rotational motion, i.e., a pitch motion, around the pulley shaft JX4 integrally with the pitch hub 3107.

The pitch hub 3107 is connected to the end tool hub 3108 and the jaw 3103, and may rotationally move around the pulley shaft JX4 by being axially coupled to the end tool hub 3108 by the pulley shaft JX4. Further, the jaw 3103 may be axially coupled to the pitch hub 3107 with respect to one pulley shaft, i.e., the pulley shaft JX1. The jaw 3103 may perform a rotational motion, i.e., a yaw motion, around one pulley shaft, i.e., the pulley shaft JX1 while connected to the pitch hub 3107.

An auxiliary pulley shaft may be additionally disposed together with these rotation shafts, i.e., the pulley shafts for joint motion of the end tool 3100, such as the pulley shaft JX4 for pitch motion and the pulley shaft JX1 for yaw motion.

For example, the pulley shaft JX2 which is different from the pulley shaft JX1 is disposed in the pitch hub 3107 to be adjacent to and parallel to the pulley shaft JX1. The pulley shaft JX2 may have an axis oriented parallel to the pulley shaft JX1, and may be disposed further away from the operation member 3140 than the pulley shaft JX1, i.e., closer to the connector 3400.

In addition, the pulley shaft JX3 may be disposed adjacent to the pulley shaft JX4. In addition, the pulley shaft JX5 may be further disposed.

For example, the pulley shaft JX3 and the pulley shaft JX5 may be disposed on both sides of the pulley shaft JX4 interposed therebetween, and the pulley shaft JX3 and the pulley shaft JX5 may have axes oriented parallel to the pulley shaft JX4.

As a specific example, the pulley shaft JX3 may be disposed between the pulley shaft JX2 and the pulley shaft JX4, and may have an axis intersecting or orthogonal to the pulley shaft JX2 and the pulley shaft JX1. The pulley shaft JX5 may be disposed further away from the operation member 3140 than the pulley shaft JX4, i.e., closer to connector 3400.

One or more switching pulley shafts AX1 and AX2, i.e., a first switching pulley shaft AX1 and a second switching pulley shaft AX2, may be disposed closer to the operation member 3140 than the pulley shafts JX1, JX2, JX3, JX4, and JX5.

The first switching pulley shaft AX1 and the second switching pulley shaft AX2 may be shafts formed parallel to each other. The first switching pulley shaft AX1 and the second switching pulley shaft AX2 may be sequentially disposed in a direction toward the distal end 3101d of the first jaw 3101 so as to be offset from each other based on a width direction of the first jaw 3101, and may be disposed with some regions overlapping.

One or more pulleys may be disposed on the pulley shafts JX1, JX2, JX3, JX4, and JX5 and the switching pulley shafts AX1 and AX2.

When description is given in the order from the proximal end of the first jaw 3101 towards the connector 3400, one or more switching pulleys AXP1 corresponding to the first switching pulley shaft AX1 and one or more switching pulleys AXP2 corresponding to the second switching pulley shaft AX2 are disposed.

The one or more switching pulleys AXP1 corresponding to the first switching pulley shaft AX1, and the one or more switching pulleys AXP2 corresponding to the second switching pulley shaft AX2 may all be disposed in a place overlapping the first jaw 3101, for example, may be disposed in one region of the coupling region 3101z of the first jaw 3101 so as not to overlap the pitch hub 3107.

The first forward-moving wire 3111 and the second forward-moving wire 3112 may come into contact with the switching pulleys AXP1 and the switching pulley AXP2, respectively, in at least one region, and thus may be guided in path.

For example, the first forward-moving wire 3111 may enter the switching pulleys AXP1 from the outside, wind inward, continue winding into one region of the switching pulleys AXP2 adjacent to the switching pulleys AXP1, and then exit from the switching pulleys AXP2.

The second forward-moving wire 3112 may come into contact with the switching pulleys AXP2 in at least one region, and may be guided in path. The first forward-moving wire 3111 and the second forward-moving wire 3112, which are collected in the switching pulley AXP2, may be wound together around one or more pulleys JXP1 corresponding to the pulley shaft JX1, which will be described below, in the same direction.

Accordingly, the first forward-moving wire 3111 and the second forward-moving wire 3112 can be moved in one direction, and can be organized on one side of the shaft and pulley for each joint motion, such as the pulley shaft and pulleys for pitch motion and the pulley shaft and pulleys for yaw motion, rather than on both sides of the shaft and pulley for each joint motion, thus facilitating precise implementation of simultaneous and straightforward control over the first forward-moving wire 3111 and the second forward-moving wire 3112.

For example, when the end tool 3100 performs yaw and pitch motions, the wires wound around the yaw pulley (for yaw motion) or the pitch pulley (for pitch motion) may be wound or unwound further to one side, whereas the first forward-moving wire 3111 and the second forward-moving wire 3112 of the present embodiment can be gathered and organized on one side, i.e., wound in the same direction on the yaw pulley and the pitch pulley, and thus may be wound or unwound the same distance. Accordingly, the two wires can be easily controlled together by a single driving unit (e.g., an actuator) since the first forward-moving wire 3111 and the second forward-moving wire 3112 need only be wound or unwound by the same distance in order to make yaw and/or pitch manipulation to prevent the operation member 3140 from moving.

In an optional embodiment, the first forward-moving wire 3111 and the second forward-moving wire 3112 may be wound in different directions around the yaw pulley and the pitch pulley, respectively. When the first forward-moving wire 3111 or the second forward-moving wire 3112 is pulled, an undesired rotational force may be generated in the end tool 3100, which may occur because each of the first forward-moving wire 3111 and the second forward-moving wire 3112 is offset by a radius of the yaw pulley or the pitch pulley, causing asymmetrical forces to be applied to the end tool 3100. At this point, when the first forward-moving wire 3111 and the second forward-moving wire 3112 are wound in opposite directions around the yaw pulley and the pitch pulley, respectively, the rotational forces in the end tool 3100 may be canceled through application of symmetrical forces, thereby reducing a change in position/posture of the end tool 3100 during a stapling process. In this case, the first forward-moving wire 3111 and the second forward-moving wire 3112 may be wound around one side and unwound around another side, and thus a compensating member may be further disposed to compensate for this. As an example, the first forward-moving wire 3111 and the second forward-moving wire 3112 may be formed into a single loop by placing a common pulley in one region of the end tool 3100, or the connector 3400 or the operator 3200 adjacent thereto. As another example, the first forward-moving wire 3111 and the second forward-moving wire 3112 may each be manipulated by a separate driving unit (e.g., an actuator).

In order to facilitate the path guidance for the first forward-moving wire 3111 and the second forward-moving wire 3112, the switching pulley AXP1 and the switching pulley AXP2 may have structures symmetrical to each other with respect to an extension line of the operation member 3140, that is, may have structures offset by the same distance with respect to the extension line of the operation member 3140. This allows the size of each of the switching pulley AXP1 and the switching pulley AXP2 to be increased, thereby improving the efficiency and stability of the path guidance for the first forward-moving wire 3111 and the second forward-moving wire 3112.

One or more pulleys JXP1 are disposed to correspond to the pulley shaft JX1, and one or more pulleys JXP2 corresponding to the pulley shaft JX2 are disposed adjacent to the one or more pulleys JXP1. The pulley JXP1 and the pulley JXP2 may have axes parallel to each other.

For example, the pulley JXP1 and the pulley JXP2 are disposed in the first hub 3107a (refer to FIG. 26) of the pitch hub 3107. One or more pulleys JXP2 guide the paths along which the wires, which are disposed to correspond to one or more pulleys JXP1, are driven, ensuring that the wires have a clear path to the pulley shaft JX4, or more closely, to the pulley shaft JX3 and a pulley JXP3 corresponding thereto.

Further, one or more pulleys JXP3 are disposed to correspond to the pulley shaft JX3, and one or more pulleys JXP4 corresponding to the pulley shaft JX4 are disposed adjacent to the one or more pulleys JXP4. For example, the pulley JXP3 and the pulley JXP4 are disposed in the second hub 3107b (refer to FIG. 26) of the pitch hub 3107. In addition, one or more pulleys JXP5 may be disposed to correspond to the pulley shaft JX5. The pulley JXP3, the pulley JXP4, and the pulley JXP5 may have axes that are parallel to each other and intersecting or orthogonal to the axes of the pulley JXP1 and the pulley JXP2.

Meanwhile, by precisely controlling the paths of the first forward-moving wire 3111 and the second forward-moving wire 3112 as shown in FIGS. 43 and 44, the drive efficiency and control characteristics of the operation member 3140 can be maximized through the first forward-moving wire 3111 and the second forward-moving wire 3112.

As described above, the first switching pulley AXP1 and the second switching pulleys AXP2 are disposed further forward than the pulley shaft JX4 and the pulley shaft JX1, which are respectively for two joint motions such as a pitch motion and a yaw motion of the end tool 3100, i.e., disposed closer to the operation member 3140 than the above pulleys.

As a specific example, the first switching pulley AXP1 and the second switching pulleys AXP2 are disposed further forward than the pulley JXP4 corresponding to the pulley shaft JX4 for a pitch motion, the pulley JXP1 corresponding to the pulley shaft JX1 for a yaw motion, the pulley JXP3 and the pulley JXP5 corresponding to pitch auxiliary pulleys, and the pulley JXP2 that is a yaw auxiliary pulley, i.e., disposed closer to the operation member 3140 than the above pulleys.

As a result, the first switching pulley AXP1 and the second switching pulleys AXP2 are disposed further forward than the pulley JXP1, the pulley JXP2, the pulley JXP3, the pulley JXP4, and the pulley JXP5, i.e., disposed closer to the operation member 3140 than the above pulleys.

Accordingly, the first forward-moving wire 3111 may enter the switching pulleys AXP1 from the outside, wind inward, continue winding into one region of the switching pulleys AXP2 adjacent to the switching pulleys AXP1, and then exit from the switching pulleys AXP2. In addition, the first forward-moving wire 3111 and the second forward-moving wire 3112 may be gathered together on one side (e.g., an outer side) of the switching pulley AXP2.

In addition, the first forward-moving wire 3111 and the second forward-moving wire 3112, which are gathered together on the outer side of the switching pulley AXP2, may be directed to the connector 3400 after being simultaneously rerouted at an outer side of the pulley JXP1 corresponding to the pulley shaft JX1, which is a yaw pulley shaft, being wound around the pulley JXP2 corresponding to the pulley shaft JX2, which is a yaw auxiliary pulley shaft, to be rerouted, being controlled in path height by the pulley JXP3 corresponding to the pulley shaft JX3, being stably placed on a lower side of the pulley JXP4 corresponding to the pulley shaft JX4, which is a pitch shaft, and passing through the pulley JXP5.

That is, by first gathering the first forward-moving wire 3111 and the second forward-moving wire 3112 together through the switching pulley AXP1 and the switching pulley AXP2, the paths of the first forward-moving wire 3111 and the second forward-moving wire 3112 can be easily guided by simultaneously corresponding to the rotation shafts and the pulleys and their auxiliary pulleys for the joint motion of the end tool 3100, so that the accuracy and stability of the forward movement of the operation member 3140 can be improved.

In addition, by controlling heights of the paths of the first forward-moving wire 3111 and the second forward-moving wire 3112, which are gathered together, using the pulley JXP3 prior to directing to the pulley JXP4 corresponding to the pulley shaft JX4, which is a pitch shaft, the first forward-moving wire 3111 and the second forward-moving wire 3112 can be stably wound around the pulley JXP4 corresponding to the pulley shaft JX4, which is a pitch shaft, and the freedom of size, design and arrangement of the pulley JXP4 can be improved.

In an optional embodiment, the backward-moving wire BRW may be further disposed as described above, in which case the backward-moving wire BRW may pass between the switching pulley AXP1 and the switching pulley AXP2, or pass in contact with a common region of the switching pulley AXP1 and the switching pulley AXP2, and then pass while corresponding to the other pulleys JXP1, JXP2, JXP3, JXP4, and JXP5.

For example, the backward-moving wire BRW may correspond to the switching pulley disposed on the shaft parallel to or the same shaft as at least one of the switching pulley shafts AX1 and AX2, and specifically, may pass to correspond to the one or more pulleys disposed on the switching pulley shafts AX1 and AX2 and opposite to the switching pulley AXP1 or the switching pulley AXP2.

Meanwhile, the backward-moving wire BRW may be wound around the pulleys JXP1 and JXP2 in a direction opposite to the direction in which the first forward-moving wire 3111 and the second forward-moving wire 3112 are wound. For example, when the first forward-moving wire 3111 and the second forward-moving wire 3112 are wound around a rear side of the pulley JXP1 and wound around a front side of the pulley JXP2, the backward-moving wire BRW may be wound around a front side of the pulley JXP1 and wound around a rear side of the pulley JXP2. This allows the first forward-moving wire 3111 and the second forward-moving wire 3112 to be wound around one side of one or more pulley shafts, and the backward-moving wire BRW to be wound around another side thereof, and when at least one of the first forward-moving wire 3111 and the second forward-moving wire 3112 and the backward-moving wire BRW form a close loop, tension of the entire wire can be easily maintained.

For example, when the end tool is manipulated for a yaw motion or a pitch motion, the wire wound around the shaft corresponding to the motion may be further wound or unwound depending on the direction in which the wire is wound, in this case, when the forward-moving wires 3111 and 3112 and the backward-moving wire BRW are wound in opposite directions, the backward-moving wire BRW may be unwound as much as the forward-moving wires 3111 and 3112 is wound, or the forward-moving wires 3111 and 3112 may be unwound as much as the backward-moving wire BRW is wound, and consequently the overall length of the close loop of the forward-moving wires 3111 and 3112 and the backward-moving wire BRW may be maintained, thereby facilitating the maintenance of tension. At this point, a driving unit (e.g., an actuator) may be used to pull the forward-moving wires 3111 and 3112 or the backward-moving wire BRW to further limit unnecessary movement of the operation member 3140.

As a further example, the close loop of the forward-moving wires 3111 and 3112 and the backward-moving wire BRW may be formed by winding the forward-moving wires 3111 and 3112 and the backward-moving wire BRW around a common pulley fixing the common pulley to a rotation shaft of the rotating driving unit (e.g., an actuator).

Meanwhile, pulling the first forward-moving wire 3111 and the second forward-moving wire 3112 of the present embodiment may cause some rotational force on the end tool 3100 due to the tension thereof, which may cause the jaw 3103 biting the body tissue to lose balance, or cause unnecessary external forces to be applied to the body tissue. In this case, the pulleys and the corresponding pulley shafts of the end tool 3100 may tilt or move slightly, as a result, inner diameter edges of the pulleys may dig into the pulley shafts, thereby increasing friction and tightening the coupling of the pulley and the pulley shaft. Accordingly, friction forces are generated to resist abnormal rotational forces on the end tool 3100, which can improve the reliability and usability of the end tool 3100. In addition, this is applicable even when the backward-moving wire BRW is used, and is applicable to the embodiments described below and the embodiments described above without change.

Meanwhile, when the tension applied to the first forward-moving wire 3111 and the second forward-moving wire 3112 or the backward-moving wire BRW is released, the frictional force may be eliminated together.

The present disclosure has been described above in relation to its preferred embodiments. It will be understood by those skilled in the art that various changes in form and details may be made therein without departing from the essential features of the present disclosure. Therefore, the disclosed embodiments should be considered in descriptive sense only and not for purposes of limitation. The scope of the present disclosure is defined not by the detailed description of the disclosure but by the appended claims, and all differences within the scope will be construed as being included in the present disclosure.

According to the present disclosure described above, in a shaft attachment and detachment apparatus to be used in various surgical devices, a shaft can be easily attached to or detached by one hand operation, thereby improving operability.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

The invention claimed is:
1. A shaft attachment and detachment apparatus for attaching and detaching a shaft having grooves formed on one end portion to and from a device body, the shaft attachment and detachment apparatus comprising:
a sleeve surrounding at least a portion of an outer surface of the shaft and movable in an axial direction of the shaft;
a connector base into which one end portion of the shaft is inserted and which is coupled to the device body; and
a latch member coupled to the connector base and including one or more latches,
wherein the one or more latches are coupled to the grooves, which are formed in the shaft, to couple the shaft to the connector base, and
the coupled state of the one or more latches and the grooves is changeable depending on a position of the sleeve disposed on the shaft.
2. The shaft attachment and detachment apparatus of claim 1, wherein
the coupling of the one or more latches and the grooves is maintained while the sleeve covers the one or more latches coupled to the grooves, and
the coupling of the one or more latches and the grooves is releasable while the sleeve does not cover the one or more latches coupled to the grooves.
3. The shaft attachment and detachment apparatus of claim 1, further comprising an elastic member housing disposed between the sleeve and an outer circumferential surface of the shaft and fixedly coupled to the shaft, wherein
the elastic member housing includes an elastic member disposed between the sleeve and the elastic member housing,
the elastic member provides an elastic force in a direction of pushing the sleeve toward the grooves of the shaft, and
by disposing the one or more latches in a separation space formed between the sleeve and the shaft, the sleeve covers the one or more latches.
4. The shaft attachment and detachment apparatus of claim 1, wherein by moving the sleeve toward a distal end, which is in a direction away from the connector base, the one or more latches are exposed to the outside of the sleeve, and the coupling of the one or more latches and the grooves is releasable.
5. The shaft attachment and detachment apparatus of claim 4, wherein in a state in which the sleeve covers the one or more latches, uncoupling of the one or more latches from the grooves is limited even when an external force is applied to the shaft.
6. The shaft attachment and detachment apparatus of claim 1, wherein the latch member includes:
a body fixedly coupled to the connector base;
legs each formed to extend from the body; and
a latch formed on an end portion of each of the legs,
wherein the latch includes an inner side protrusion with at least one region inserted into a corresponding one of the grooves of the shaft.
7. The shaft attachment and detachment apparatus of claim 6, wherein
the body of the latch member includes a through hole through which the shaft is inserted, and
the legs are formed to extend from the body toward the grooves along an outer circumferential surface of the shaft.
8. The shaft attachment and detachment apparatus of claim 6, wherein
each of the one or more latches includes an outer side protrusion formed on an opposite side of the inner side protrusion, and when the shaft is inserted into the connector base, the one or more latches are spread in a direction away from a central axis of the shaft while interfering with the outer circumferential surface of the shaft, and the outer side protrusion comes in contact with the sleeve.

9. The shaft attachment and detachment apparatus of claim 8, wherein the sleeve interferes with the outer side protrusion and thus is slidably moved in a direction opposite to an insertion direction of the shaft.

10. The shaft attachment and detachment apparatus of claim 8, wherein, when the shaft is further inserted toward the connector base, at least one region of the inner side protrusion is inserted into the grooves to couple the one or more latches to the grooves.

11. The shaft attachment and detachment apparatus of claim 8, wherein the inner side protrusion includes a first inclined surface formed to have a greater height on a distal end side, which is in a direction away from the connector base, than on a proximal end side, which is in a direction close to the connector base.

12. The shaft attachment and detachment apparatus of claim 8, wherein the grooves of the shaft each include a groove-inclined surface formed such that a width of the groove becomes smaller toward an inner surface from an outer surface of the shaft.

13. The shaft attachment and detachment apparatus of claim 6, wherein each of the one or more latches includes an outer side protrusion formed on an opposite side of the inner side protrusion, wherein the outer side protrusion includes a third inclined surface formed to have a higher height on a proximal end side, which is in a direction close to the connector base, than on a distal end side, which is in a direction away from the connector base, and the sleeve includes a fourth inclined surface, which corresponds to the third inclined surface, on one end portion thereof facing the latch.

14. The shaft attachment and detachment apparatus of claim 13, wherein the third inclined surface and the fourth inclined surface are in contact with each other, and the fourth inclined surface presses the third inclined surface toward the center of the shaft.

15. The shaft attachment and detachment apparatus of claim 13, wherein the sleeve includes a locking protrusion extending from the fourth inclined surface and formed to be parallel to the shaft.

16. The shaft attachment and detachment apparatus of claim 1, wherein the shaft has a key groove extending in a longitudinal direction at an end portion thereof, the connector base has at least one protrusion formed on an inner surface thereof, protruding toward a central axis of the shaft, and as the protrusion is fitted into the key groove, an axial rotation of the shaft is prevented.

17. A device attachment and detachment module provided in a device body to attach and detach a shaft to and from the device body, the device attachment and detachment module comprising:

a connector base into which one end portion of the shaft is inserted and which is coupled to the device body; and a latch member coupled to the connector base and including one or more latches, wherein the one or more latches are coupled to the shaft to couple the shaft to the connector base, and the coupled state of the one or more latches and the shaft is changeable by a sleeve disposed on the shaft.

18. The device attachment and detachment module of claim 17, wherein the latch member includes:

a body fixedly coupled to the connector base;

legs each formed to extend from the body; and a latch formed on an end portion of each of the legs, wherein each of the one or more latches includes an inner side protrusion having at least one region inserted into a groove formed on one end portion of the shaft.

19. The device attachment and detachment module of claim 18, wherein each of the one or more latches includes an outer side protrusion formed on an opposite side of the inner side protrusion, and when the shaft is inserted into the connector base, the one or more latches are spread in a direction away from a central axis of the shaft while interfering with the outer circumferential surface of the shaft, and the outer side protrusion comes in contact with the sleeve.

20. The device attachment and detachment module of claim 19, wherein the sleeve interferes with the outer side protrusion and thus is slidably moved in a direction opposite to an insertion direction of the shaft.

21. The device attachment and detachment module of claim 19, wherein, when the shaft is further inserted toward the connector base, at least one region of the inner side protrusion is inserted into the groove to couple a corresponding one of the one or more latches to the groove.

22. The device attachment and detachment module of claim 18, wherein each of the one or more latches includes an outer side protrusion formed on an opposite side of the inner side protrusion, wherein the outer side protrusion includes a third inclined surface formed to have a higher height on a proximal end side, which is in a direction close to the connector base, than on a distal end side, which is in a direction away from the connector base, and the sleeve includes a fourth inclined surface, which corresponds to the third inclined surface, on one end portion thereof facing the one or more latches.

23. The device attachment and detachment module of claim 22, wherein the third inclined surface and the fourth inclined surface are in contact with each other, and the fourth inclined surface presses the third inclined surface toward the center of the shaft.

24. A shaft attachment and detachment module provided on a shaft having grooves formed on one end portion to attach and detach the shaft to and from a device body, the shaft attachment and detachment module comprising:

a sleeve surrounding at least a portion of an outer surface of the shaft and movable in an axial direction of the shaft; and an elastic member housing disposed between the sleeve and an outer circumferential surface of the shaft and fixedly coupled to the shaft, wherein, the elastic member housing includes an elastic member disposed between the sleeve and the elastic member housing, the shaft is coupled to the device body by latches included in the device body, and the coupled state of the latches and the shaft is changeable depending on a position of the sleeve disposed on the shaft.

25. The shaft attachment and detachment module of claim 24, wherein the latches are respectively coupled to the grooves formed on one end portion of the shaft,

53 the coupling of the latches and the grooves is maintained while the sleeve covers the latches coupled to the grooves, and the coupling of the latches and the grooves is releasable while the sleeve does not cover the latches coupled to the grooves.

26. The shaft attachment and detachment module of claim 24, wherein the elastic member provides an elastic force in a direction of pushing the sleeve toward the groove of the shaft, and the sleeve covers the latches as the latches are disposed in a separation space formed between the sleeve and the shaft.

27. The shaft attachment and detachment module of claim 24, wherein, by moving the sleeve toward a distal end, which is in a direction away from the device body, the latches are exposed to the outside of the sleeve, and the coupling of the latches and the grooves is releasable.

28. The shaft attachment and detachment module of claim 27, wherein, in a state in which the sleeve covers the latches, uncoupling of the latches from the grooves is limited even when an external force is applied to the shaft.

29. A medical device including a shaft attachment and detachment apparatus, the medical device comprising:

a connection member including a shaft-shaped coupling part having grooves formed on one end portion thereof;

a sleeve surrounding at least a portion of an outer surface of the shaft-shaped coupling part and movable in an axial direction of the shaft-shaped coupling part;

a connector base into which one end portion of the shaft-shaped coupling part is inserted and which is coupled to the device body; and a latch member coupled to the connector base and including one or more latches, wherein the one or more latches are respectively coupled to the grooves, which are formed in the shaft-shaped coupling part, to couple the connection member to the connector base, the coupled state of the one or more latches and the grooves is changeable depending on a position of the sleeve disposed on the shaft-shaped coupling part.

30. The medical device of claim 29, wherein the coupling of the one or more latches and the grooves is maintained while the sleeve covers the one or more latches coupled to the grooves, and the coupling of the one or more latches and the grooves is releasable while the sleeve does not cover the one or more latches coupled to the grooves.

31. The medical device of claim 29, further comprising an elastic member housing disposed between the sleeve and an outer circumferential surface of the shaft-shaped coupling part and fixedly coupled to the shaft-shaped coupling part, wherein the elastic member housing includes an elastic member disposed between the sleeve and the elastic member housing, the elastic member provides an elastic force in a direction of pushing the sleeve toward the grooves of the shaft-shaped coupling part, and by disposing the one or more latches in a separation space formed between the sleeve and the shaft-shaped coupling part, the sleeve covers the one or more latches.

32. The medical device of claim 29, wherein the latch member includes:

a body fixedly coupled to the connector base;

legs each formed to extend from the body; and a latch formed on an end portion of each of the legs, wherein the latch includes an inner side protrusion having at least one region inserted into a corresponding one of the grooves of the shaft-shaped coupling part.

33. The medical device of claim 32, wherein each of the one or more latches includes an outer side protrusion formed on an opposite side of the inner side protrusion, wherein the outer side protrusion includes a third inclined surface formed to have a higher height on a proximal end side, which is in a direction close to the connector base, than on a distal end side, which is in a direction away from the connector base, and the sleeve includes a fourth inclined surface, which corresponds to the third inclined surface, on one end portion thereof facing the one or more latches.

34. The medical device of claim 29, wherein the connection member is a replaceable consumable component, and the device body is a multi-use component.

* * * * *